(12) United States Patent
Winnik et al.

(10) Patent No.: US 9,465,036 B2
(45) Date of Patent: Oct. 11, 2016

(54) PARTICLES CONTAINING DETECTABLE ELEMENTAL CODE

(75) Inventors: Mitchell A. Winnik, Toronto (CA); Cedric Vancaeyzeele, Vernouillet (FR); Vladimir I. Baranov, Richmond Hill (CA)

(73) Assignee: Fluidigm Canada Inc., Markham (CA)

( * ) Notice: Subject to any disclaimer, the term of this patent is extended or adjusted under 35 U.S.C. 154(b) by 1302 days.

(21) Appl. No.: 12/513,011

(22) PCT Filed: Nov. 2, 2007

(86) PCT No.: PCT/US2007/083465
§ 371 (c)(1),
(2), (4) Date: Feb. 24, 2010

(87) PCT Pub. No.: WO2008/058004
PCT Pub. Date: May 15, 2008

(65) Prior Publication Data
US 2010/0144056 A1 Jun. 10, 2010

Related U.S. Application Data

(60) Provisional application No. 60/864,001, filed on Nov. 2, 2006.

(51) Int. Cl.
*G01N 33/68* (2006.01)

(52) U.S. Cl.
CPC .......... *G01N 33/6848* (2013.01); *Y10T 436/24* (2015.01)

(58) Field of Classification Search
None
See application file for complete search history.

(56) References Cited

U.S. PATENT DOCUMENTS

| | | | | |
|---|---|---|---|---|
| 2,830,958 A | * | 4/1958 | Linn et al. | 502/181 |
| 3,853,987 A | * | 12/1974 | Dreyer | 424/1.37 |
| 4,022,876 A | | 5/1977 | Anbar | |
| 4,096,393 A | * | 6/1978 | Sher | G01J 5/34 |
| | | | | 136/254 |
| 4,205,952 A | | 6/1980 | Cais | |
| 4,421,896 A | * | 12/1983 | Dorman | C08G 81/02 |
| | | | | 435/181 |
| 4,448,908 A | * | 5/1984 | Pauly | C08F 291/00 |
| | | | | 523/201 |
| 4,454,233 A | | 6/1984 | Wang | |
| 4,499,052 A | | 2/1985 | Fulwyler | |
| 4,543,439 A | | 9/1985 | Frackelton, Jr. et al. | |
| 4,717,655 A | | 1/1988 | Fulwyler | |
| 5,073,498 A | | 12/1991 | Schwartz et al. | |
| 5,091,206 A | * | 2/1992 | Wang et al. | 427/2.18 |

(Continued)

FOREIGN PATENT DOCUMENTS

| | | | | |
|---|---|---|---|---|
| CA | WO 2005/093784 | * | 10/2005 | H01J 49/26 |
| WO | WO9714028 A2 | | 4/1997 | |

(Continued)

OTHER PUBLICATIONS

Quinn (2002) J Anal At Spect 17: 892-896.*

(Continued)

*Primary Examiner* — Chris L Chin
*Assistant Examiner* — Richard Moerschell
(74) *Attorney, Agent, or Firm* — Kilpatrick Townsend & Stockton LLP

(57) ABSTRACT

The invention relates to a new type of element encoded particles suitable for the attachment of bio molecules to enable massively multiplex bio-analytical methods, and to calibrate and tune the elemental flow cytometer mass spectrometer (FC-MS).

8 Claims, 27 Drawing Sheets endohedral fullerenes

(56) References Cited

U.S. PATENT DOCUMENTS

| | | | |
|---|---|---|---|
| 5,191,010 A * | 3/1993 | Inagaki et al. | 524/510 |
| 5,194,300 A | 3/1993 | Cheung | |
| 5,521,289 A | 5/1996 | Hainfeld et al. | |
| 5,585,241 A | 12/1996 | Lindmo | |
| 5,686,518 A * | 11/1997 | Fontenot et al. | 524/458 |
| 5,723,218 A | 3/1998 | Haughland | |
| 5,736,330 A | 4/1998 | Fulton | |
| 5,981,180 A | 11/1999 | Chandler et al. | |
| 6,057,107 A | 5/2000 | Fulton | |
| 6,242,735 B1 | 6/2001 | Li et al. | |
| 6,449,562 B1 | 9/2002 | Chandler et al. | |
| 6,514,295 B1 | 2/2003 | Chandler et al. | |
| 6,524,793 B1 | 2/2003 | Chandler et al. | |
| 6,599,331 B2 | 7/2003 | Chandler et al. | |
| 6,632,528 B1 | 10/2003 | Clough | |
| 6,929,859 B2 | 8/2005 | Chandler et al. | |
| 6,939,720 B2 | 9/2005 | Chandler et al. | |
| 7,135,296 B2 | 11/2006 | Baranov et al. | |
| 7,198,900 B2 | 4/2007 | Woudenberg et al. | |
| 7,410,763 B2 | 8/2008 | Su et al. | |
| 7,479,630 B2 | 1/2009 | Bandura et al. | |
| 7,494,776 B2 | 2/2009 | Wallace et al. | |
| 7,700,295 B2 | 4/2010 | Baranov et al. | |
| 7,767,407 B2 | 8/2010 | Baranov et al. | |
| 2002/0132992 A1 * | 9/2002 | Leif et al. | 534/615 |
| 2003/0028981 A1 | 2/2003 | Chandler et al. | |
| 2003/0148544 A1 * | 8/2003 | Nie et al. | 436/524 |
| 2003/0199633 A1 * | 10/2003 | Leon | C08F 2/24 524/800 |
| 2004/0002574 A1 * | 1/2004 | Ri et al. | 525/203 |
| 2004/0023040 A1 * | 2/2004 | Gellermann et al. | 428/446 |
| 2004/0053052 A1 | 3/2004 | Chandler et al. | |
| 2004/0072250 A1 | 4/2004 | Baranov et al. | |
| 2004/0126901 A1 | 7/2004 | Kauvar et al. | |
| 2005/0118574 A1 | 6/2005 | Chandler et al. | |
| 2005/0164261 A1 | 7/2005 | Chandler et al. | |
| 2005/0191665 A1 * | 9/2005 | Su | G01N 33/54346 435/6.11 |
| 2005/0202469 A1 | 9/2005 | Chandler et al. | |
| 2005/0218319 A1 | 10/2005 | Bandura et al. | |
| 2005/0260676 A1 | 11/2005 | Chandler et al. | |
| 2006/0003366 A1 | 1/2006 | DiCesare | |
| 2006/0177850 A1 | 8/2006 | Schermer et al. | |
| 2006/0240411 A1 | 10/2006 | Mehrpouyan et al. | |
| 2006/0240444 A1 | 10/2006 | Chu | |
| 2007/0037215 A1 | 2/2007 | Patton | |
| 2007/0105990 A1 | 5/2007 | Makino et al. | |
| 2007/0148196 A1 * | 6/2007 | Haas | A61K 9/1277 424/401 |
| 2007/0190560 A1 | 8/2007 | Ornatsky | |
| 2007/0190588 A1 | 8/2007 | Ornatsky | |
| 2008/0003616 A1 | 1/2008 | Winnick et al. | |
| 2008/0046194 A1 | 2/2008 | Antonov et al. | |
| 2008/0193930 A1 | 8/2008 | Ornatsky et al. | |
| 2009/0264548 A1 * | 10/2009 | Van der Wal | C08G 18/36 521/157 |
| 2011/0024615 A1 | 2/2011 | Tanner et al. | |

FOREIGN PATENT DOCUMENTS

| | | |
|---|---|---|
| WO | WO9919515 A1 | 4/1999 |
| WO | 02054075 A1 | 7/2002 |
| WO | 03/003015 A2 | 1/2003 |
| WO | 03/003015 A3 | 1/2003 |
| WO | 2005003767 A2 | 1/2005 |
| WO | 2005093784 A1 | 10/2005 |
| WO | 2007093049 A1 | 8/2007 |
| WO | 2007093050 A1 | 8/2007 |
| WO | 2007137418 A1 | 12/2007 |
| WO | 2008019492 A1 | 2/2008 |
| WO | 2008080224 A1 | 7/2008 |

OTHER PUBLICATIONS

Ramirez (2005) Macromol Chem Phys 207: 160-165.*
Quinn (2002) J. Anal At Spect 17: 892-896.*
Ramirez (2006) Moc Chem Phys 207: 160-165.*
Erdem (2000) J Poly Sci 38: 4441-4450.*
Thomas, R.N., et al., "Nanosphere-Antibody Conjugates with Releasable Fluorescent Probes," 2001, Fresenius J anal Chem, 369:477-482.
Bartel, et al., "Isolation of New Ribozymes From a Large Pool of Random Sequences," 1993, Science, 261:1411-1418.
Evans, R.D., et al., "A Method for Characterization of Humic and Fulvic Acids by Gel Electrophoresis Laser Ablation Inductively Coupled Plasma Mass Spectrometry," 2000, J Analy Atomic Spectrom, 15/2:157-161.
Huhtinen et al. "Synthesis, Characterization, and Application of Eu(III), Tb(III), Sm(III), and Dy(III) Lanthanide Chelate Nanoparticle Labels", Anal. Chem., 2005, v. 77, pp. 2643-2648.
LiU, et al., "Method for Quantative Proteomics Research by using Metal Element Chelated Tags coupled with Mass Spectrometry," 2006, Anal Chem, 78:6614-6621.
Ornatsky, O., et al., "Messenger RNA Detection in Leukemia Cell Lines by Novel Metal-Tagged in situ Hybridization Using Inductively Coupled Plasma Mass Spectrometry," 2006, Translational Oncogenomics, 1-9.
Soukka, et al., "Utilization of Kinetically Enhanced Monovalent Binding Affinity by Immunoassays Based on Multivalent Nanoparticle-Antibody Bioconjugates," 2001, Anal Chem, 73:2254-2260.
Tanner, S.D., et al., "Flow Cytometer with Mass Spectrometer Detection for Massively Multiplexed Single-Cell Biomarker Assay," 2008, Pure Appl Chem, 20/12:2627-2641.
J. Feng, M. A. Winnik, R. R. Shivers B. Clubb, Macromolecules, 28, 7671-7682, (1995).
W. B. Brown, J. P. Steinbach and W. P. Wagner, J. Inorg. Nucl. Chem., 13, 119-124, (1960).
Y. Meguro, Y. Kitatsuji, T. Kimura, Z. Yoshida, J. Alloys and Compounds, 271-273, 790-793, (1998).
T. Shigematsu, M. Matsui, R. Wake, Anal.Chim. Acta, 46, 101-106, (1969).
M. Morin, R. Bador, H. Dechaud, Anal.Chim. Acta, 219, 67-77, (1989).
M. Xiao, P. R. Selvin, J. Am. Chem., 123, 7067-7073, (2001).
A. P. Bassett, S. W. Magennis, P. B. Glover, D. J. Lewis, N. Spencer, S. Parsons, R. M. Williams, L. De Cola and Z. Pikramenou, J. Am. Chem., 126, 9413-9424, (2004).
L. R. Melby, N. J. Rose, E. Abramson and J. C. Caris, J.A.C.S., 86, 5117-25, (1964).
C. S. Chern, Y. C. Liou, T. J. Chen, Macromol. Chem. Phys. 199, 1315-1322 (1998).
C. S. Chern, Y. C. Liou, Polymer 40, 3763-3772, (1999).
C. S. Chern, H. T. Chang, European Polymer Journal 39, 1421-1429, (2003).
M. Antonietti, K. Landfester, Prog. Polym. Sci., 27, 689-757, (2002).
K. Landfester, N. Bechthold, S. Förster, M. Antonietti, Macromol. Rapid Commun., 20(2), 81-84, (1999).
K. Landfester, Macromol. Rapid Commun., 22(12), 896-936, (2001).
J. A. Alduncin, J. Forcada, J. M. Asua, Macromolecules, 27, 2256-2261, (1994).
J. A. Alduncin, J. M. Asua, Polymer, 35, 3758-3765, (1994).
S. Sarkar, M. S. Adhikari, M. Benjeree, R. S. Konar, J. Appl. Polym. Sci., 35, 1441, (1988).
I. A. Maxwell, B. R. Morrison, D. H. Napper, R. G. Gilbert, Macromolecules, 24, 1629-1640, (1991).
J. W. Goodwin, J. Hearn, C. C. Ho, R. H. Ottewill, Br Polym. J., 5, 347, (1973).
H-B. Kim, Y. Wang, M. A. Winnik, Polymer, 35, 1779-1786, (1994).

(56) References Cited

OTHER PUBLICATIONS

S. Kawaguchi, A. Yekta, M. A. Winnik, J. of Colloid and interface science, 176, 362-369, (1995).
T. Matsuya, S. Tashiro, N. Hoshino, N. Shibata, Y. Nagasaki, K. Kataoka, Analytical Chemistry, 75, 6124-6132, (2003).
K. Landfester, N. Bechthold, F. Tiarks, M. Antonietti, Macromolecules, 32, 5222-5228, (1999).
S. Lee, A. Rudin, J. Polym. Sci. Part A: Polymer Chemistry, 30, 865-871 (1992).
K. J. O'Callaghan, A. J. Paine, A. Rudin, J. of Appl. Polym. Sci., 58, 2047-2055 (1995).
Z. Wang, A. J. Paine, A. Rudin, J. of Colloid and interface Sci., 177, 602-612, (1996).
F. Lortie, S. Boileau, L. Bouteiller, C. Chassenieux, B. Demé, G. Ducouret, M. Jalabert, F. Lauprêtre, P. Terech, Langmuir, 18, 7218-7222, (2002).
V. I. Baranov, D. R. Bandura, S. D. Tanner, ICP-MS as an elemental . . . , European Winter Conference on Plasma Spectrochemistry, Hafjell, Norway 2001 Book of Abstracts, p. 85.
V. I. Baranov, Z. Quinn, D. R. Bandura, S. D. Tanner, A sensitive and quantitative element-tagged immunoassay with ICPMS detection, Anal. Chem. 74 (2002) 1629-1636.
V. I. Baranov, Z. A. Quinn, D. R. Bandura, S. D. Tanner, The potential for elemental analysis in biotechnology, J. Anal. Atom. Spectrom. 17 (2002) 1148-1152.
Z. A. Quinn, V. I. Baranov, S. D. Tanner, J. L. Wrana, Simultaneous determination of proteins . . . , J. Anal. Atom. Spectrom. 17 (2002) 892-896.
L. P. Ramirez, M. Antonietti, K. Landfester, Formation of novel layered nanostructures from lanthanide-complexes . . . , Macromolecular Chemistry and Physics 207 (2006) 160-165.
Hantzchel, N., et al., "Poly(N-vinylcaprolactam-co-glycidyl methacrylate) Aqueous Microgels Labeled with Fluorescent LaF3:Eu Nanoparticles," 2007, Langmuir, 23:10793-10800.
Kuang, M., et al., "Fabrication of Multicolor-Encoded Microspheres by Tagging Semiconductor Nanocrystals to Hydrogel Spheres," 2005, Adv Mater, 17/3:267-270.
Lou, X., et al., "Polymer-Based Elemental Tags for Sensitive Bioassays," 2007, Angew Chem Int Ed, 46:6111-6114.
Vancaeyseele, C., et al., "Lanthanide-Containing Polymer Nanoparticles for Biological Tagging Applications: Nonspecific Endocytosis and Cell Adhesion," 2007, J Am Chem Soc, 129:13653-13660.
Verpoorte, E., "Beads and Chips: New Recipes for Analysis," 2003, Lab Chip, 3:60N-68N.
Yang, Y. et al., "Incorporating CdTe Nanocrystals into Polystyrene Microspheres: Towards Robust Fluorescent Beads," 2006, Small, 2/7:898-901.
Extended Search Report issued in EP 07844843.8, dated Jan. 3, 2011, 8 pages.
International Search Report issued in PCT/US07/83465, dated Jul. 31, 2008, 5 pages.
Bechtold, N., et al., "Miniemulsion Polymerization: Applications and New Materials," 2000, Macromol Symp, 151:549-555.
Blythe, P.J., et al., "Miniemulsion Polymerization of Styrene using the Oil-Soluble Initiator AMBN," 2999, J Polym Sci Part A, 36:4449-4457.
Erdmen, B., et al., "Encapsulation of Inorganic Particles via Miniemulsion Polymerization. I. Dispersion of Titanium Dioxide Particles in Organic Media . . . ," 2000, J Polym Sci Part A, 38:4419-4430.
Erdmen, B., et al., "Encapsulation of Inorganic Particles via Miniemulsion Polymerization. II. Preparation and Chracterization of Styrene Miniemulsion . . . ," 2000, J Polym Sci Part A, 38:4431-4440.
Erdmen, B., et al., "Encapsulation of Inorganic Particles via Miniemulsion Polymerization. III. Characterization of Encapsulation," 2000, J Polym Sci Part A, 38:4441-4450.
Goodwin, J.W., et al., "Studies on the Preparation and Characterisation of Monodisperse Polystyrene Latices*) III. Preparation without Added Surface Active Agents," 1974, Colloid & Polymer Sci, 252:464.
Joumma, N., et al., "Synthesis of Quantum Dot-Tagged Submicrometer Polystyrene particles by Miniemulsion Polymerization," 2006, Langmuir, 22:1810-1816.
Schork, F.J., et al., "Miniemulsion Polymerization," 2005, Adv Polym Sci, 175:129-255.
Song, et al., "Monodisperse, Micrometer-sized Low Molar Mass Polystyrene Particles by Two-stage Dispersion Polymerization," 2006, Polymer, 47:4557-4563.
Yildiz, U., et al., "The Fabrication of Very Small Miniemulsion Latexes from N-Stearoylglutamate and Lauryl Methacrylate: Evidence for Droplet Budding," 2003, Macromol Chem Phys, 204:1966-1970.

\* cited by examiner

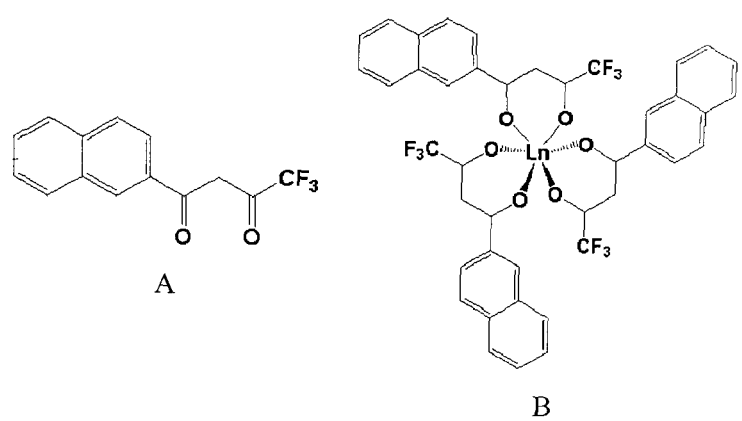
Figure 3 – a: Ligand, b: Lanthanide complex.

CV13  CV16  CV21

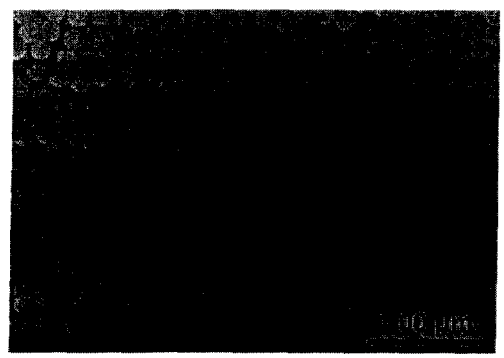 A -
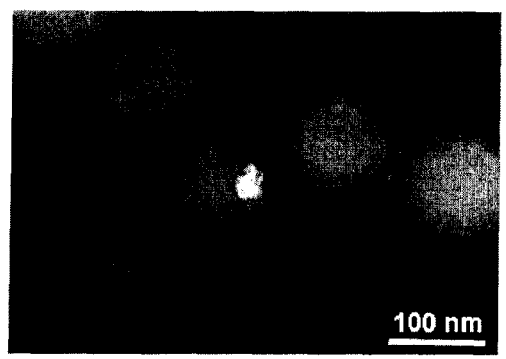 B -
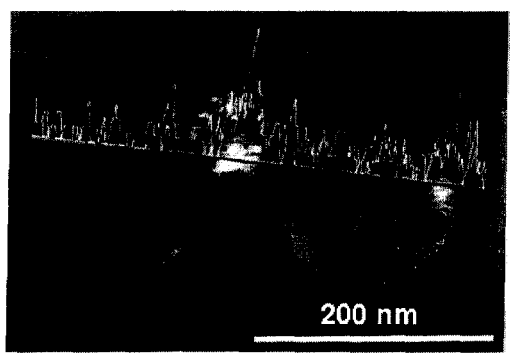 C -
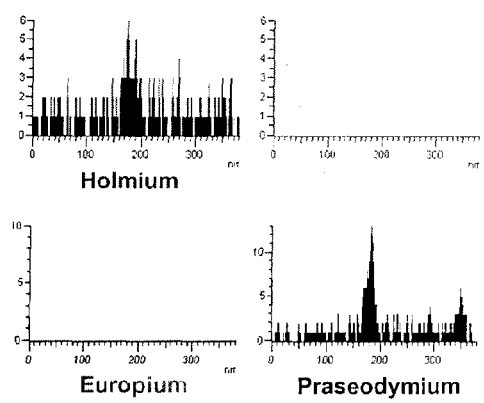 D -
Figure 14.

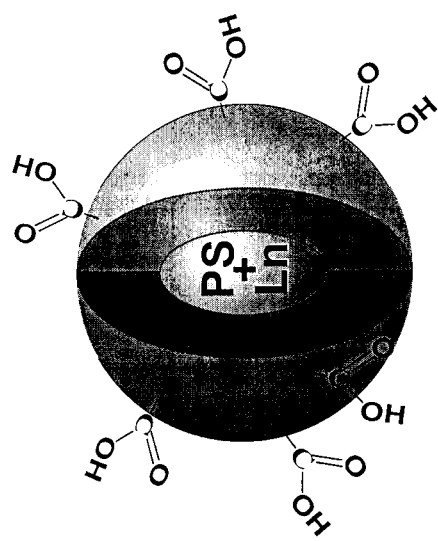
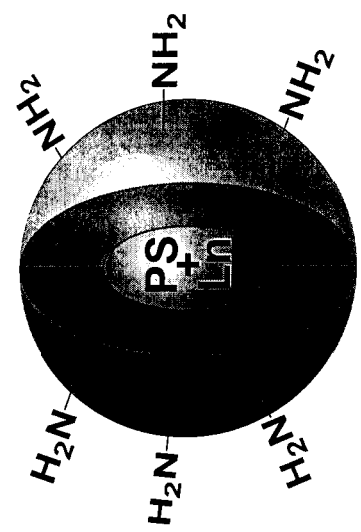
Figure 21.

PARTICLES CONTAINING DETECTABLE ELEMENTAL CODE

CROSS-REFERENCE TO RELATED APPLICATIONS

This application claims the benefit of U.S. Provisional Patent Application Ser. No. 60/864,001, entitled "Nanospheres containing detectable elemental code" and filed Nov. 2, 2006, the entire contents of which are hereby incorporated by this reference.

COPYRIGHT AND LEGAL NOTICES

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

FIELD OF THE INVENTION

The invention relates to a new type of element encoded particles suitable for the attachment of bio molecules to enable massively multiplex bio-analytical methods, and to calibrate and tune the elemental flow cytometer mass spectrometer (FC-MS).

BACKGROUND OF THE INVENTION

New technology that enables a single cell/particle analysis based on element tags[1] is emerging in the vigorous area of proteomics and drug discovery and could be equally useful in areas of clinical and diagnostic testing. The realization that elemental analysis offers significant advantages to the field of protein quantitation has directed the development of several new methods of protein quantitation via Inductively Coupled Plasma Mass Spectrometry (ICP-MS) linked immunoassays[2-6].

Fluorescent light emitting beads (particles) are well known in a number of practical applications especially in combination with flow cytometry based methods. It was long recognized that "two or more dyes of varying proportions could be used to increase the permutation number of unique combinations of dyes in a single particle [7]". The art is based on realization that the emission wavelengths and fluorescence intensities are useful for multi-parametric analysis of a plurality of analytes in the same sample.

Although it is feasible to have an optical emission detector capable of distinguishing a plurality of wavelengths and an excitation system with significantly broad range, it is still physically impossible to create a set of non-interfering fluorophores for a large number of unique combinations of dyes in a single particle. Typically dyes have overlapping excitation and emission spectra allowing energy transfer from the first excited dye to the next dye and through a series of dyes resulting in emission of light from the last dye in the series. Specifically for fluorescence based cytometry these limitations also include: limited dynamic range due to some spectral overlap and detector capabilities, and variability in fluorophore response (fluorophore integrity problem). In the multiplex configuration, distinguishable (meaning non-overlapping signal) fluorescent dyes are required. This results in mismatched overlap of the excitation and absorption wavelengths, with a corresponding loss in sensitivity for some of the fluorophores. More significantly, the emission spectra are not well baseline-resolved. That is, some overlap of the fluorescent signals is obtained, and this becomes important when a large signal in one channel overlaps strongly into the weaker signal channel.

On the contrary, the elemental analysis (ICP-MS, for example) has a number of unique properties that could be harnessed to create an ideal element stained particles and instrument combination for the purpose of the invention and to provide a multiplex alternative to fluorescence based methods [1].

A large number of heavy metals (as an example, the element stain, but not limited thereto) and their isotopes provide distinct signals that can be detected by MS simultaneously. Two or more elements of varying proportions could be used to increase the permutation number of unique combinations of elements in a single particle; the obtained intensity ratio vs. tag mass fingerprint could serve as a signature of the particle. Using more than two elements as staining elements yields a much larger number of detectable permutations than is feasible by fluorescently dyed particles. The method of analyzing the element-labeled particle takes advantage of the abundance sensitivity of ICP-MS, a measure of the overlap of signals of neighboring isotopes, is large ($>10^6$ for the quadrupole analyzer), and this ensures independence of the detection channels over a wide dynamic range. Further, MS is very sensitive, permitting the determination of signals at biologically significant levels. Finally, ICP-MS as a detector offers absolute quantification that is largely independent of the analyte molecular form or sample matrix. In this invention we teach, among other things, the formulation of the element stained beads and their use as a tuning standard for ICP-MS as well as functionalization of their surface to be useful as a support (for capture antibodies, for example) in bio-analytical applications.

FC-MS with element-encoded beads overcomes existing limitations of fluorescent-based suspension assays. Consider an element-encoding system for beads that employs five elements (e.g., La, Pr, Tb, Ho, Tm, all of which occur naturally as single isotopes) present at ten grades of concentration of the encoding elements, the variability will be $10^5-1=99,999$. Elemental mass spectrometry is able to quantify up to ca. $10^6$ grades of concentration (depending on the particular MS technique) for adjacent isotopes which translates into $10^{11}-1$ types of distinguishable "bar-coded" beads (theoretical limit). If practical isotope separation for samarium (Sm, with seven isotopes having >3% abundance) could be achieved with 99% purity, the corresponding bead-encoded system would have, assuming 10 grades of concentration, nearly ten million bead varieties (i.e., $10^7-1$). In principle, there is no physical limit (other than MS sensitivity) to distinguishing the very large (i.e., massive) variety of element-encoded beads if MS detection is used. The polymeric element-encoded beads should not be light sensitive, will not leach out Ln ions (they are firmly encapsulated inside the fullerene), and will not require special storage conditions. In addition, there will be no background interference from sample containers or biological molecules. In one instance, we teach design a bead-based assay using polystyrene beads with embedded elemental code. The assay consists of covalently attaching a specific antibody to one type of coded bead; incubating the beads with samples containing the antigen of interest and after washing beads by low speed centrifugation probing with a reporter antibody that binds to a different epitope of the antigen and is labeled with an elemental tag. Combining several uniquely encoded beads will permit to assay multiple antigens from a single biological sample. In one instance all reporter antibodies can be labeled with the same elemental tag. The FC-MS read-out will indicate the type and quantity of antigens present in the biological sample.

Synthesis of beads intended for general bio-analytical purpose was described in the following references and, in the case of making multicolored, fluorescent beads, methods have been disclosed including: i. covalent attachment of dyes onto the surface of the particle[8], ii. internal incorporation of dyes during particle polymerization [9,10], and iii. dyeing after the particle has been already polymerized [7,11]. However, these references disclose production of fluorescent particles. Instructions for incorporation of non-fluorescent elements were not provided.

U.S. Pat. No. 6,449,562 [12] provides a general description of a multiplexed analysis of biological molecules using beads, but does not provide instructions or disclosure for providing element tagged (encoded) beads as well as no MS linked assays are disclosed.

U.S. Pat. No. 4,454,233 [13] suggests that elements embedded in "individual mobile units" could be resolved by a mass spectrometer. However, the resultant mass spectra were not provided, and synthetic strategies for "individual mobile units" with embedded elements were not presented, effectively preventing one skilled in the art to make and use such beads in mass spectrometry. As a result, no usage of the element stained beads in combination with a mass spectrometer has been practiced to date.

U.S. Pat. No. 7,225,082 provides description and preparation of rod-shaped nanoparticles. Althoght the elemental composition of the nanoparticles is varied along the length of the rod to provide viasible nanobar codes, the invention does not provide instructions or disclosure for providing element tagged (encoded) beads as well as no elemental analysis linked assays are disclosed.

Ramirez et al [14] reported miniemulsion polym-erization of butyl acrylate (BA) in water in which the BA droplets contained various lanthanides (Dy, Er, Eu, Gd, Ho, La, Pr, Yb) chelated with 2,2,6,6-tetramethyl-3,5-heptanedione. (These particular lanthanide chelates are sold commercially as NMR shift reagents.) These complexes have a low solubility in water, and the authors report preparation of poly(butyl acrylate) (PBA) particles containing a mole ratio BA/Ln complex ranging from 8.9 to 55.2. These authors did not use their metal-polymer hybrid particles as seeds for the preparation of coreshell particles, did not teach the synthesis of mixed lanthanides particles, did not encapsulate lanthanide nanoparticles into polymer particles via miniemulsion polymerization, nor did they mention any potential applications of their particles; although one skilled in the art might expect that these kind of particles could be used as a fluorophores.

Clearly, it would be an important improvement to the art to have a means of precisely element staining a particle with two or more elements premixed in a series of predetermined ratios and to have a collection of such element stained particles for use in multiplex applications. This precision in element staining process can be achieved with significantly improved ratio of the standard deviation to the mean mass spectrometer intensity of particle population in comparison with fluorescent based techniques. This fundamental difference allows incomparably more subsets or populations of non-overlapping, distinctly element stained particles to be synthesized. To ensure dramatically higher multiplex capability, it would be a further advance in the art if the methods were reproducible to within a minimal variation, to allow repeatable tuning of the elemental flow cytometer [1] across a wide variation of absolute and relative concentrations of the element stain.

SUMMARY OF THE INVENTION

We teach a novel design of the element stained particles, which are clearly needed to enable massively multiplex bio-analytical methods. In one of the aspects of their utility, the element stained particles also can be used to calibrate and tune the elemental flow cytometer [1] as well as other elemental analyzers.

The invention relates to a new type of element encoded particles suitable for the attachment of bio molecules to enable massively multiplex bio-analytical methods, and to calibrate and tune the elemental flow cytometer mass spectrometer (FC-MS). In one approach, one synthesizes polymer particles containing metal ions or atoms embedded in the interior. The polymer matrix of the particles serves to encapsulate the metal ions, but at the same time provides colloidal stability in aqueous media. The polymer matrix of the particles minimizes the direct contact of the metal ions with the aqueous phase, and functional groups at the particle surface are available for attaching antibodies or other biomolecules to the particle. These functional groups can also be used to attach linker arms or spacer groups to which biomolecules can be attached. The polymer particles of interest have diameters ranging from about several nm to about 20 μm, with those of greatest interest having diameters of about 50 nm to about 500 nm.

In one embodiment of the invention, one can employ chelated lanthanide (or other metal) ions in miniemulsion polymerization to create polymer particles with the chelated lanthanide ions embedded in the polymer. The chelating groups are chosen, as is known to those skilled in the art, in such a way that the metal chelate will have negligible solubility in water but reasonable solubility in the monomer for miniemulsion polymerization. Typical monomers that one can employ are styrene, methylstyrene, various acrylates and methacrylates, among others as is known to those skilled in the art. For mechanical robustness, the metal-tagged particles have a glass transition temperature (Tg) above room temperature. In one aspect of the invention, we propose to synthesize core-shell particles in which the metal-containing particles prepared by miniemulsion polymerization are used as seed particles for a seeded emulsion polymerization to control the nature of the surface functionality. The surface functionality can be introduced through the choice of appropriate monomers for this second-stage polymerization. Additionally, acrylate (and possible methacrylate) polymers are advantageous over polystyrene particles because the ester groups can bind to or stabilize the unsatisfied ligand sites on the lanthanide complexes.

We teach examples of the synthesis of lanthanide complexes. We describe the synthesis of lanthanide-containing polystyrene particles by miniemulsion polymerization, examining certain important reaction parameters. In another aspect, the invention provides methods of synthesis of lanthanide-containing polymer particles by miniemulsion polymerization. Finally, we provide novel formulation of seeded emulsion polymerization to produce core-shell particles and to introduce surface functionality.

In one aspect, the invention features a plurality of element stained particles, usable by a Mass Spectrometer-based Flow Cytometer (FC-MS), each particle having a Mass Spectrometer (MS) readable elemental code, wherein each said particle comprises at least one staining element, said staining element being selected such that upon FC-MS interrogation of each individual particle, a distinct MS signal is obtained from said at least one staining element, wherein the intensity of said signal is proportional to the amount of said at least one staining element in said particle, whereby said signal represents the MS readable elemental code.

In one embodiment the particles are further characterized as having the capacity to bind an affinity reagent or antigen or bio-molecule.

In another embodiment the affinity reagent or antigen or bio-molecule is further characterized as having the capacity to bind a secondary affinity reagent.

In another embodiment the affinity reagent and secondary affinity reagent are an element-tagged.

In another embodiment the element-tagged affinity reagent is a reporter tag.

According to the invention the plurality of particles have large number of differing staining elements that characterize said particles. The number is between 1 and about 100. In another embodiment the particle is characterized by having differing ratios of at least two staining elements which is between about 1 and about 1 000 000.

According to the invention the particles can have a uniform distribution as well as a non-uniform distribution of said particle sizes. Also, the particles can have at least one staining element uniformly as well as not uniformly distributed throughout each particle of said plurality of particles. The amount of said at least one element stain is between 1 and about 10 000 000 (or more) atoms of the stain element per particle.

In one embodiment of the invention at least one staining element is a transition element or an isotope thereof, or a lanthanide or an isotope of a lanthanide.

In another aspect the invention features a method of producing polymeric particles incorporating in or on the particles one or more staining elements to facilitate determination of said particles by FC-MS, said method comprising: (a) combining at least one staining element-containing complex in a solvent mixture comprising at least one organic monomer (such as styrene and/or methyl methacrylate in one embodiment) in which the at least one element-containing complex is soluble and at least one different solvent in which said organic monomer and said at least one element-containing complex are less soluble, (b) emulsifying the mixture of step (a) for a period of time sufficient to provide a uniform emulsion; (c) initiating polymerization and continuing reaction until a substantial portion of monomer is converted to polymer; and (d) incubating the product of step (c) for a period of time sufficient to obtain a latex suspension of polymeric particles with the at least one staining element-containing complex incorporated in or on the particles therein, wherein said at least one staining element-containing complex is selected such that upon FC-MS interrogation of each individual particle of said stained polymeric particles, a distinct MS signal is obtained from said at least one staining element, wherein the intensity of said signal is proportional to the amount of said at least one element stain in said individual particle of said stained polymeric particles.

In one embodiment the element-containing complex is organic or inorganic metal complexes, or colloidally stable inorganic nanoparticles.

In another embodiment, the invention is related to preparing a series of said mixtures of at least one organic monomer having different concentrations of said at least one staining element-containing complex in order to produce different sets of polymeric particles.

In yet another embodiment, the invention is related to preparing a series of said mixtures having different ratios of at least two staining element-containing complexes in order to produce different sets of polymeric particles.

In another aspect the invention features a method of staining polymeric particles with one or more elements to facilitate determination of each individual particle of said particles by FC-MS, said method comprising: (a) combining at least one staining element-containing complex in a solvent mixture comprising at least one organic solvent in which the at least one element-containing complex is soluble and at least one other solvent in which the at least one element-containing complex is less soluble, to produce a solution of at least one element-containing complex, wherein said solution is further characterized as having the capacity to swell at least partially but not dissolve the polymeric particles; and (b) incubating the solution of step (a) with polymeric particles for a period of time sufficient to provide staining of said polymeric particles with the at least one staining element-containing complex, wherein said at least one staining element-containing complex is selected such that upon FC-MS interrogation of each individual particle of said stained polymeric particles, a distinct MS signal is obtained from at least one staining element, wherein the intensity of said signal is proportional to the amount of said at least one element stain in said individual particle of said stained polymeric particles.

In one embodiment, the invention is related to preparing a series of said solutions having different concentrations of said at least one staining element-containing complex in order to produce different sets of polymeric particles.

In another embodiment, the invention is related to incubating a separate set of polymeric particles with each solution of said series of said solutions to provide multiple distinct sets or subsets of polymeric particles, each distinct set or subset being characterized by similar particles that differ from the similar particles of the other distinct sets or subsets by having different concentrations of said at least one staining element-containing complex.

In yet another embodiment, the invention is related to preparing a series of said solutions having different ratios of said at least two staining element-containing complexes in order to produce different sets of polymeric particles.

In yet another embodiment, the invention teaches incubating separate sets of polymeric particles with said series of said solutions to provide multiple distinct sets or subsets of polymeric particles, each distinct set or subset having a different ratio of said at least two staining element-containing complexes.

In yet another aspect the invention features a method of producing core-shell polymeric particles, each core-shell polymeric particle comprising a core-shell and a stained core particle within said core-shell, wherein one or more staining elements are incorporated into said stained core particle to facilitate determination of said core-shell polymeric particles by FC-MS, said method comprising: (a) combining said stained core particles in a solvent mixture comprising at least one organic monomer which is further characterized as having the capacity to polymerize said organic monomer onto the surface of each of said core particles and at least one different solvent in which said organic monomer is less soluble, to provide a mixture of stained core particles with said monomer; and (b) adding, step wise or continuously, the organic monomer, initiator, and surfactant to the solvent mixture of step (a) for a period of time sufficient to obtain a latex suspension of core-shell polymeric particles with the at least one staining element-containing complex incorporated therein, wherein said at least one staining element incorporated within the core particle is selected such that upon FC-MS interrogation of each individual particle of said stained polymeric particles a distinct MS signal is obtained from the said at least one staining element, wherein the intensity of said signal is proportional to the amount of said at least one element stain in said individual particle of said stained polymeric particles.

In one embodiment, the invention teaches preparing a series of said solvent mixtures of at least one organic monomer with said core particles having differing concentrations of at least one staining element-containing complex incorporated therein in order to produce different sets of core-shell polymeric particles.

In another embodiment, the invention teaches preparing a series of said mixtures of at least one organic monomer with said core particles having different ratios of at least two staining element-containing complexes incorporated therein in order to produce different sets of core-shell polymeric particles.

In yet another aspect the invention features a method of detecting a plurality of antigens in a biological sample, each of said antigens being recognized by a corresponding affinity reagent, said method comprising: (a) contacting said sample with a plurality of distinct sets of the particles each distinct set of particles being characterized by having each particle within each said set having a similar MS readable elemental code but a differing MS readable elemental code from each particle of every other said distinct set, each distinct set of said particles having a distinct affinity reagent bound to its surface, wherein said reagent on each set of particles specifically interacts with one of said antigens in said biological sample; (b) further contacting said sample with a plurality of element-tagged affinity reagents or reporter tags that specifically binds to the analyte, and analyzing the particles to detect said element tag indicating binding of the antigen to said element-tagged affinity reagents or reporter tags; and (c) simultaneously detecting the MS readable elemental code of each particle and the element tag of the element-tagged affinity reagent or reporter tag by FC-MS.

BRIEF DESCRIPTION OF THE DRAWINGS

The invention is illustrated in the figures of the accompanying drawings, which are meant to be exemplary and not limiting, and in which like references are intended to refer to like or corresponding parts.

Table 1. Reactants for the second stage of the stage emulsion polymerization for all the examples.

Table 2. Characteristics of the latexes synthesized as described in Examples 2 to 17.

Table 3. Particle size of samples prepared to study the hydrophobe effect synthesized according to the recipe reported in the experimental section (Example 2 and 3). dn and dw are respectively the number and weight average particle diameter measured by the CHDF. d is the particle diameter and the standard deviation, the polydispersity index (PDI) measured by the BI90 particle sizer.

Table 4. Comparison of the diameter of polystyrene particles obtained by two miniemulsion polymerization run with the same surfactant proportion (SDS, 2.5% wt/monomer) and with an oil soluble initiators (AMBN) or a water soluble initiator (KPS).

Table 4a. The characteristics of the polystyrene particles synthesized by miniemulsion polymerization with various amount of europium complex. SDS (5% wt/wt styrene) was used as surfactant and KPS (1% wt/wt styrene) as the initiator.

Table 5. The characteristics of the polystyrene particles containing various amount of different mixtures of lanthanide complexes and synthesized by miniemulsion polymerization. SDS (2.5% wt/wt styrene) was used as surfactant and KPS (1% wt/wt styrene) as the initiator. The reactions were run for 6 hours at 70° C.

Table 6. ICP-MS results of assays of the serum (following particle precipitation with NaCl) for various latex containing lanthanide complexes. The elements detected were 159Tb, 153Eu, 139La, 165Ho and 141Pr, and amounts are reported in ppb based on the mass of the latex sample (polystyrene particles plus water) present in the original sample. A control experiment was performed on pure (Milli-Q) deionized water.

Table 7. Particle size of samples prepared with different shell functionality. The polystyrene particles containing praseodymium (12.5 mg), holmium (12.5 mg), terbium (12.5 mg) and europium (25 mg) complexes per g styrene were used as seed.

Table 8. The mean number of acid groups per particle at the particle surface of metal-free core/shell particles CV81 and CV83 and lanthanide-containing particles CV117, CV118 and CV119 determined by potentiometric and conductimetric titration.

Table 8a. ICP-MS results of experiment performed on different serum of latex containing lanthanide complexes. 159Tb, 153Eu, 139La, 165Ho and 141Pr isotopes were titrated in aqueous phase of latex sample composed of seed particles containing various lanthanide complexes and the corresponding core/shell particles with different shell thickness. A control experiment was performed on pure (Milli-Q) deionized water.

Figure 1:
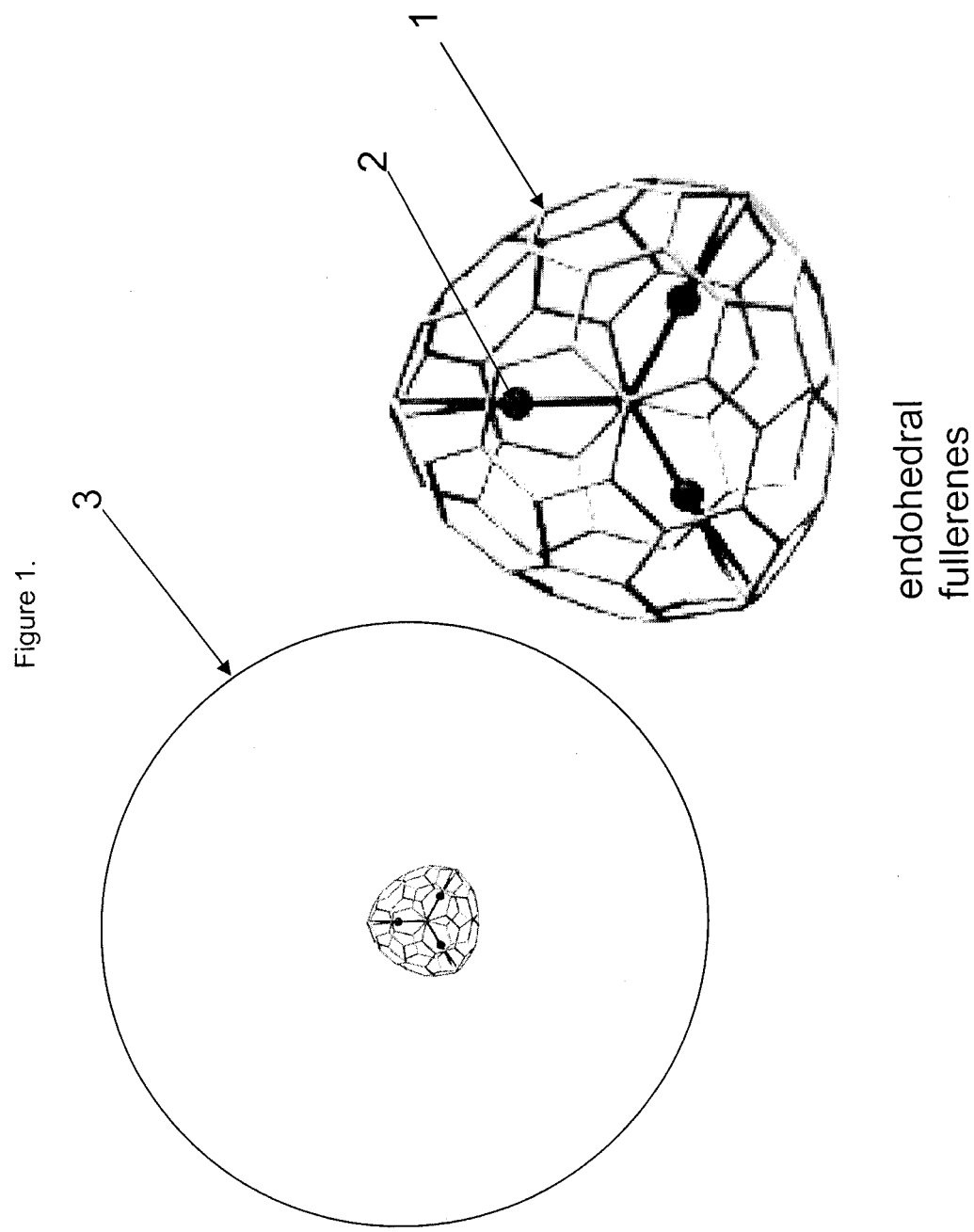

FIG. 1. Schematic views of endohedral fullerenes as element tags. 1—carbon cage; 2—metal. 3—nanospheres containing endohedral fullerenes. Functionalized endohedral fullerenes can be used as an element tag or as an encoding material for beads.

Figure 2:
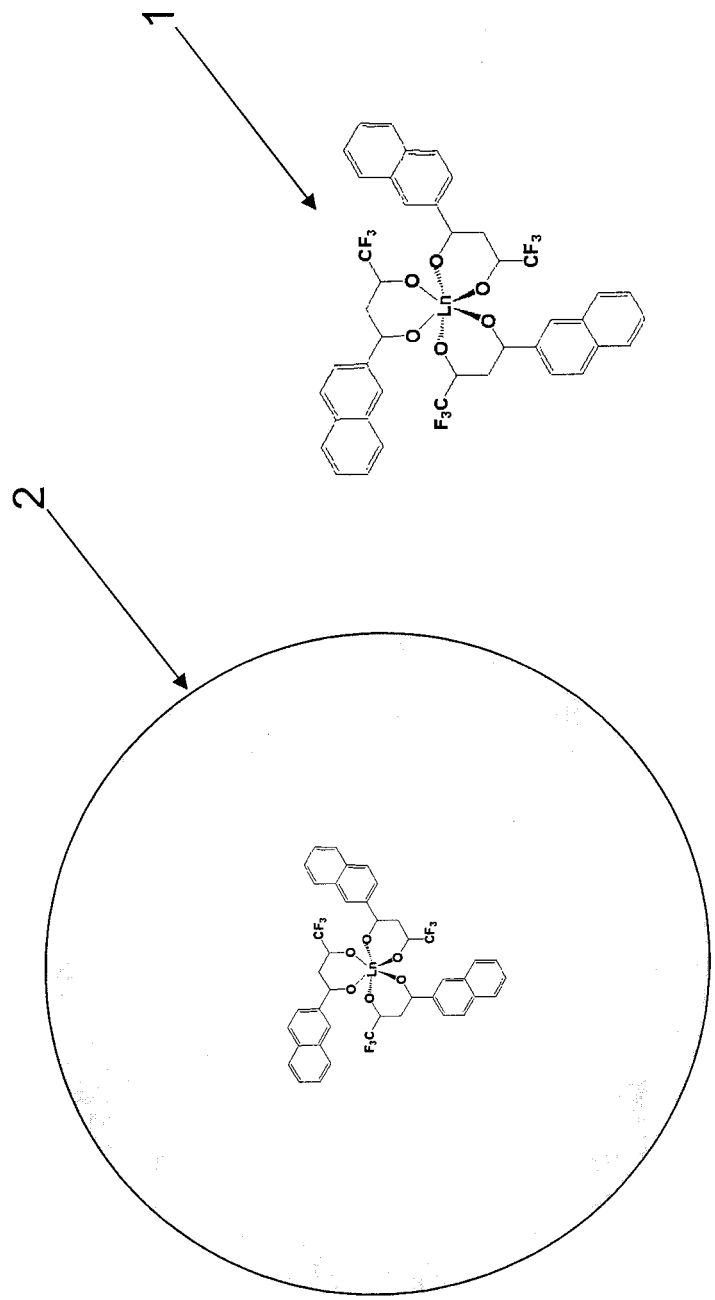

FIG. 2. Schematic views of a lanthanide complex as element tags. 1—lanthanide complex; 2—nanospheres containing lanthanide complex.

FIG. 3. Schematic views of a: Ligand, b: Lanthanide complex, according to the invention.

Figure 4A:
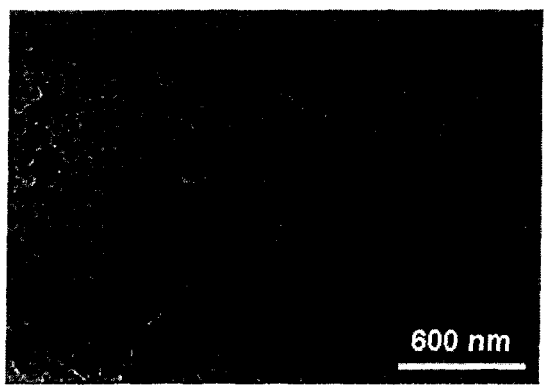

FIG. 4a. SEM image of CV65 synthesized according to the recipe of the example 3.

Figure 4B:
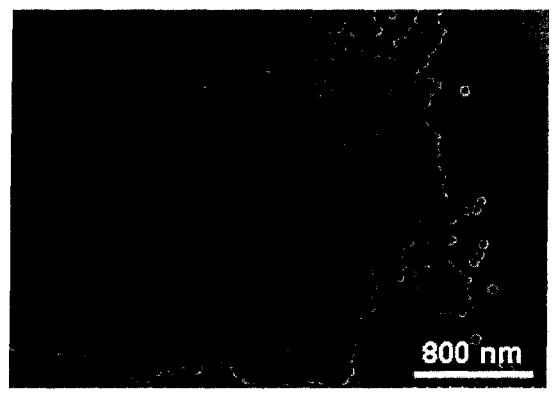

FIG. 4b. SEM image of CV80 synthesized according to the recipe of the example 3.

Figure 5:
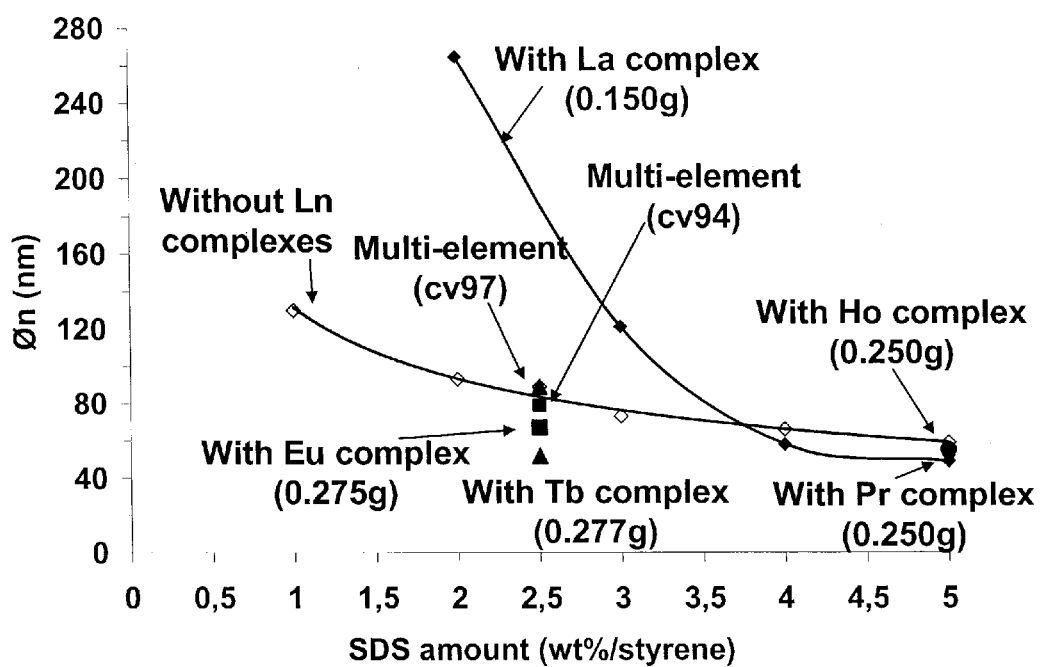

FIG. 5. Number average particle diameter measured by CHDF versus SDS amount introduced in the recipe (example 4) to synthesize different latexes. (single-element: CV38(SDS=2 wt %/styrene), CV39(SDS=5 wt %/styrene), CV42(SDS=3 wt %/styrene) and CV43(SDS=4 wt %/styrene) 0.25 g La complexes in 6 g polystyrene, CV40 0.25 g Ho complexes in 6 g polystyrene, CV41 0.25 g Pr complexes in 6 g polystyrene, CV60 0.275 g Eu complexes in 6 g polystyrene, CV61 0.277 g Tb complexes in 6 g polystyrene; Multi-element cv94: 0.15 g Eu, Tb, Ho, Pr and La complexes in 6 g polystyrene, cv97: 0.15 g Eu, 0.075 g Tb, Ho and Pr complexes in 6 g polystyrene).

Figure 6:
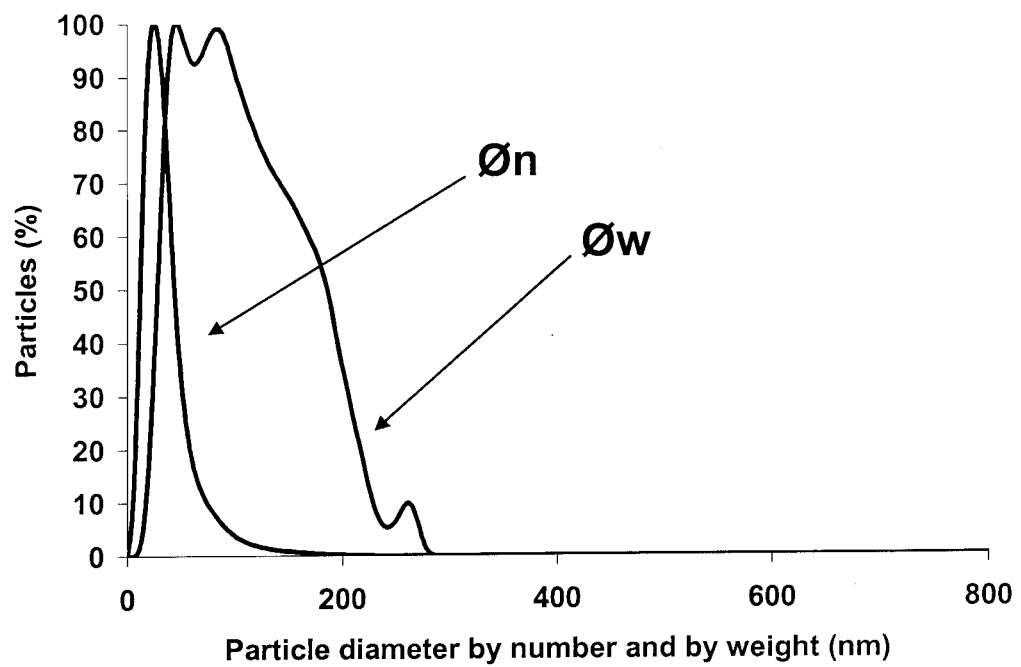

FIG. 6. CHDF analysis of the stable fraction of CV71 miniemulsion initiated by an oil soluble initiator.

Figure 7:
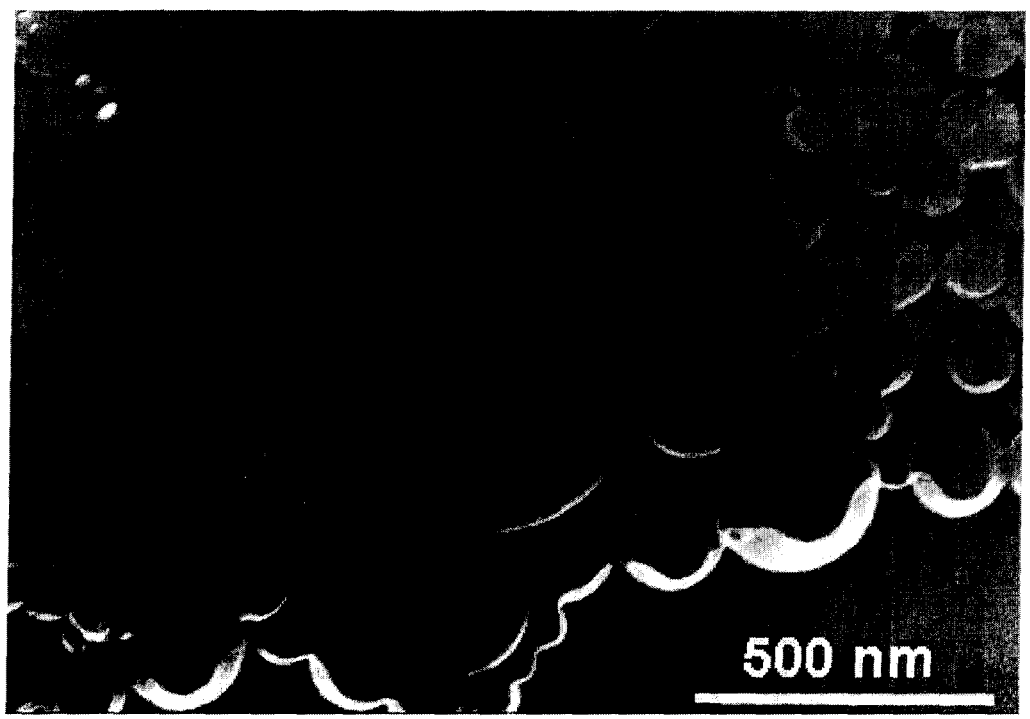

FIG. 7. SEM images of polystyrene particles containing europium complex (25 mg/g of styrene) of the stable fraction of the latex CV71 produced by miniemulsion polymerization stabilized by SDS (2.5% wt/styrene) and initiated by an oil soluble initiator (AMBN, 1% wt/wt styrene). The reactions were run for 6 hours at 70° C.

Figure 8:
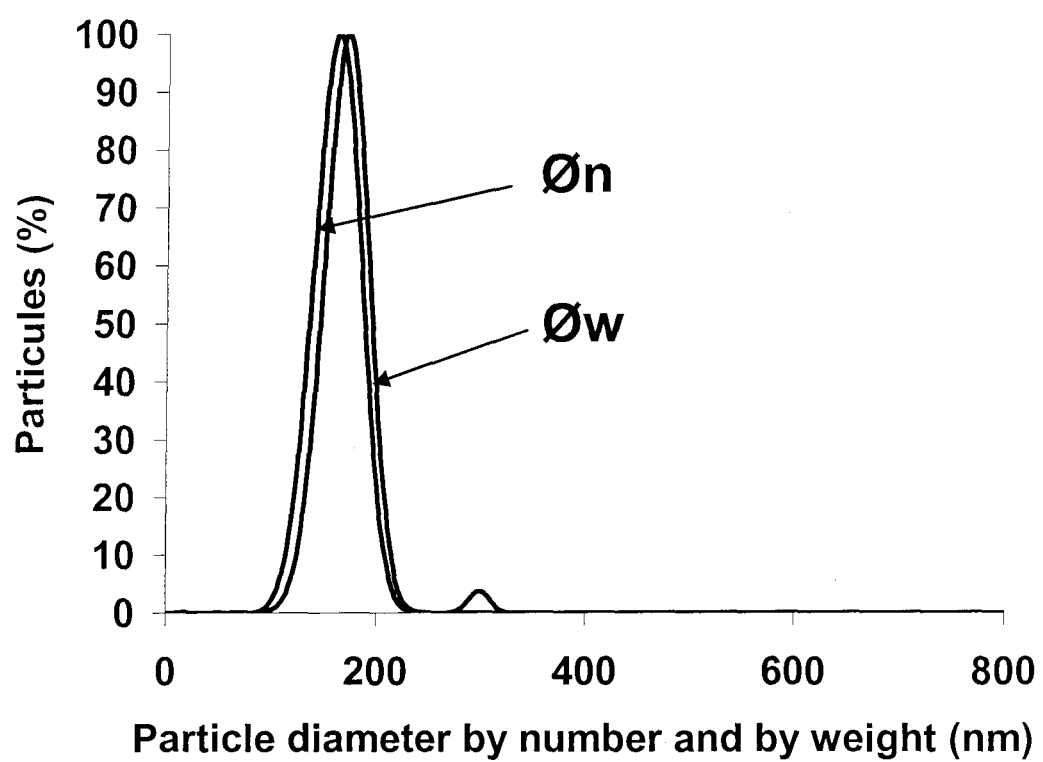

FIG. 8. CHDF analysis of CV74 miniemulsion initiated by an oil soluble initiator (AMBN,1% wt/wt styrene). These polystyrene particles containing europium complex (25 mg/g styrene) were stabilized with methacrylic acid (MAA, 5% wt/wt styrene). The reactions were run for 6 hours at 70° C.

Figure 9:
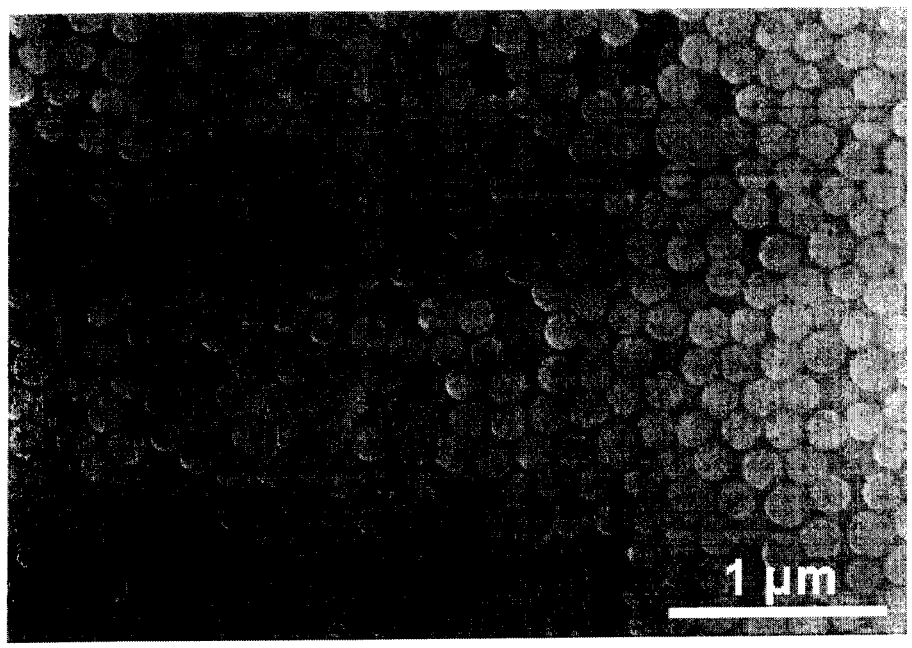

FIG. 9. SEM image of CV74 miniemulsion initiated by an oil soluble initiator (AMBN, 1% wt/wt styrene). These polystyrene particles containing europium complex (25 mg/g styrene) were stabilized with methacrylic acid (MAA, 5% wt/wt styrene). The reaction was run for 6 hours at 70° C.

Figure 10:
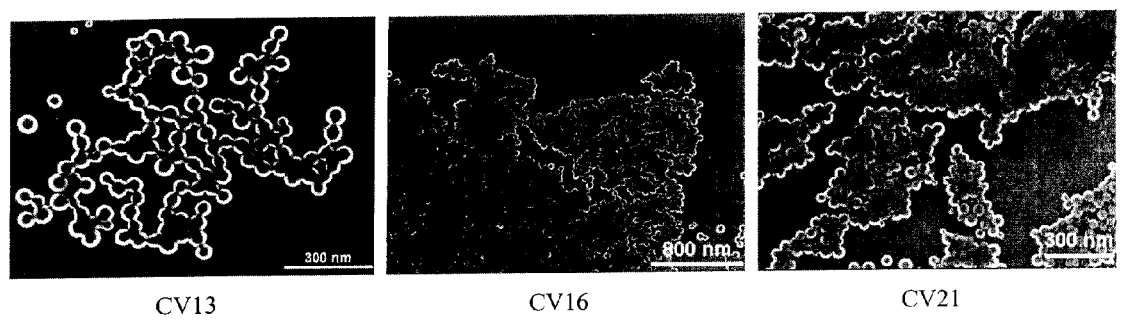

FIG. 10. SEM images of polystyrene particles loaded with various amount of europium complex (respectively 2.3, 45.8 and 166.7 mg/g of styrene for CV13, CV16 and CV21) and produced by miniemulsion polymerization stabilized by SDS (5% wt/styrene) and initiated by KPS (1% wt/wt styrene).

Figure 11:
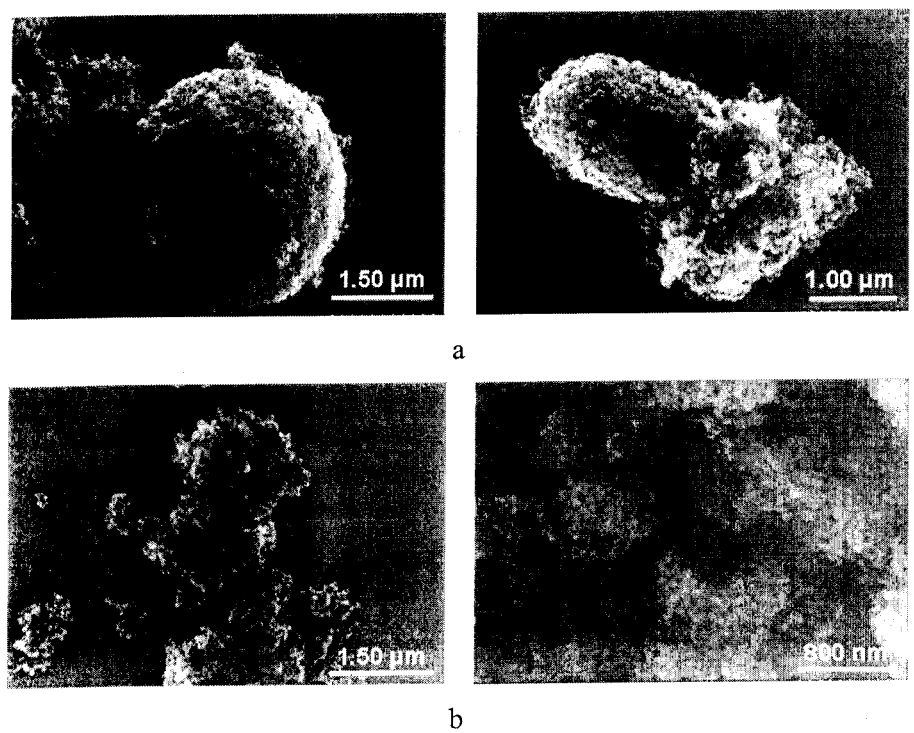

FIG. 11. SEM images of flocculated particles produced by miniemulsion polymerization. a: CV58 latex is composed of polystyrene particles loaded with various amount of europium complex (45.8 mg/g of styrene), stabilized by SDS (2% wt/styrene) and initiated by KPS (1% wt/wt styrene). b: CV20 latex is composed of polystyrene particles loaded with europium complex (205 mg/g of styrene) and produced by miniemulsion polymerization stabilized by SDS (3% wt/styrene) and initiated by KPS (1% wt/wt styrene).

Figure 12:
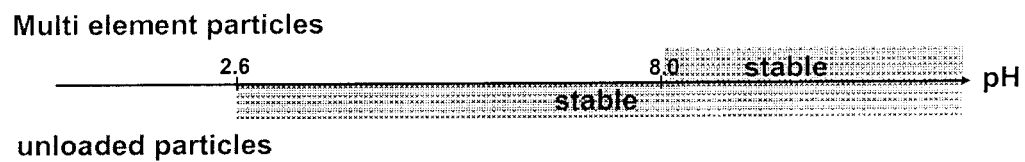

FIG. 12. Latex stability versus pH (top: multi element particles, bottom: metal-free particles). The filled pH domains represent the pH domains where the latexes keep their colloidal stability. Both latexes were produced by miniemulsion polymerization initiated by KPS (1% wt/wt styrene). The metal-containing polystyrene particles (europium, terbium, holmium, praseodymium and lanthanum complexes 25 mg of each/g of styrene) are stabilized by 2.5% wt/wt styrene of SDS and the metal-free polystyrene particles are stabilized by 2% wt/wt styrene of SDS.

Figure 13:
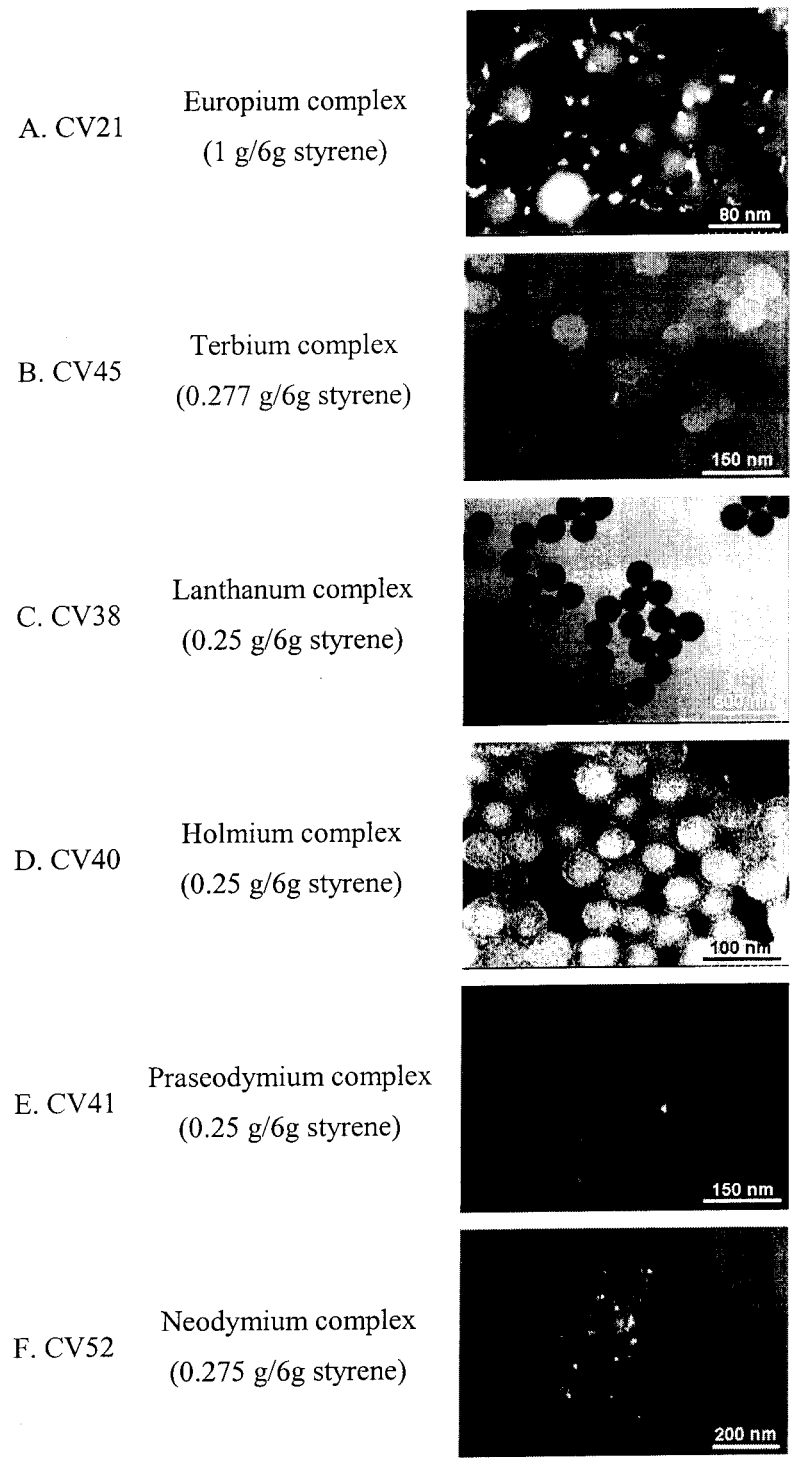

FIG. 13. TEM image of polystyrene particles containing one of each lanthanide complex and synthesized by miniemulsion polymerisazation. A: dark-field image of sample CV21 latex containing europium complex (0.17 g/g of styrene), B: dark-field image of sample CV45 latex containing terbium complex (46 mg/g of styrene), C: bright-field image of sample CV38 latex containing lanthanum complex (42 mg/g of styrene), D: dark-field image of sample CV40 latex containing holmium complex (42 mg/g of styrene), E: dark-field image of sample CV41 latex containing praseodymium complex (42 mg/g of styrene), F: dark-field image of sample CV52 latex containing neodymium complex (46 mg/g of styrene).

FIG. 14. SEM (A) and dark-field TEM (B and C) images of sample CV90 prepared with europium, terbium, holmium, praseodymium and lanthanum complexes 25 mg of each/g of styrene, C: area of the EDX line-scan, D: Elementary analysis by EDX.

Figure 15:
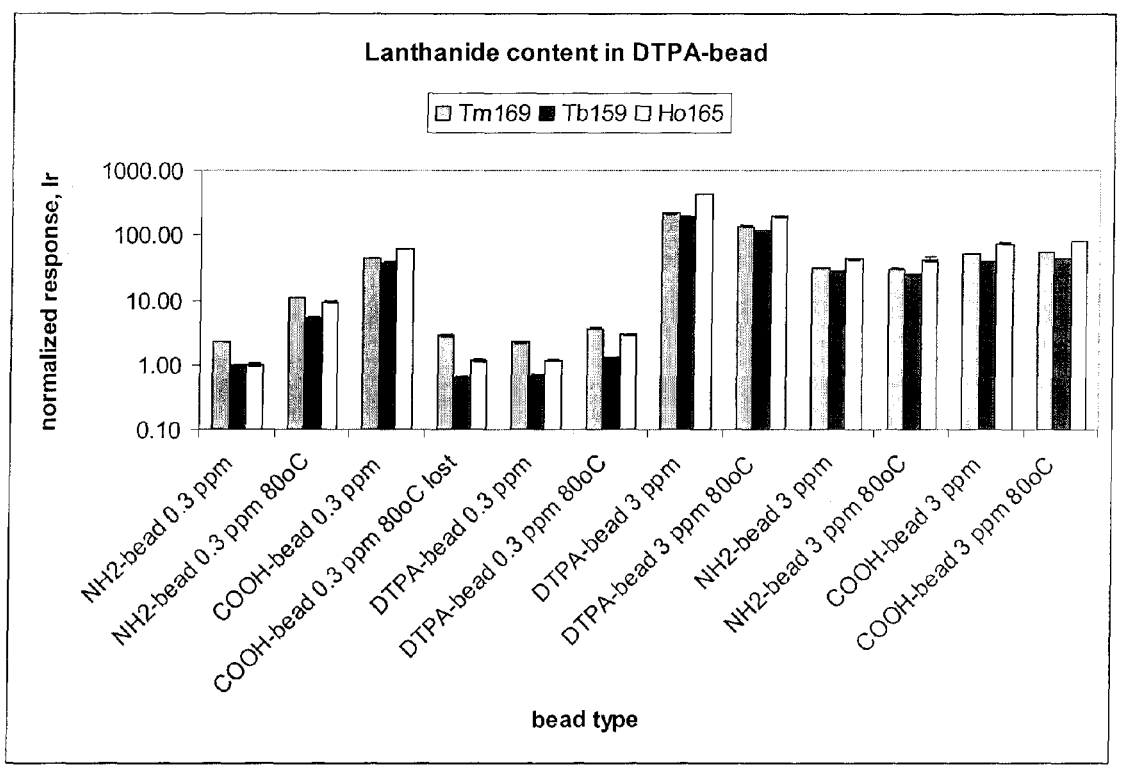

FIG. 15. Example of ICP-MS analysis of —$NH_2$, —COOH, and DTPA modified polystyrene beads encoded with Tm, Tb, and Ho.

Figure 16:
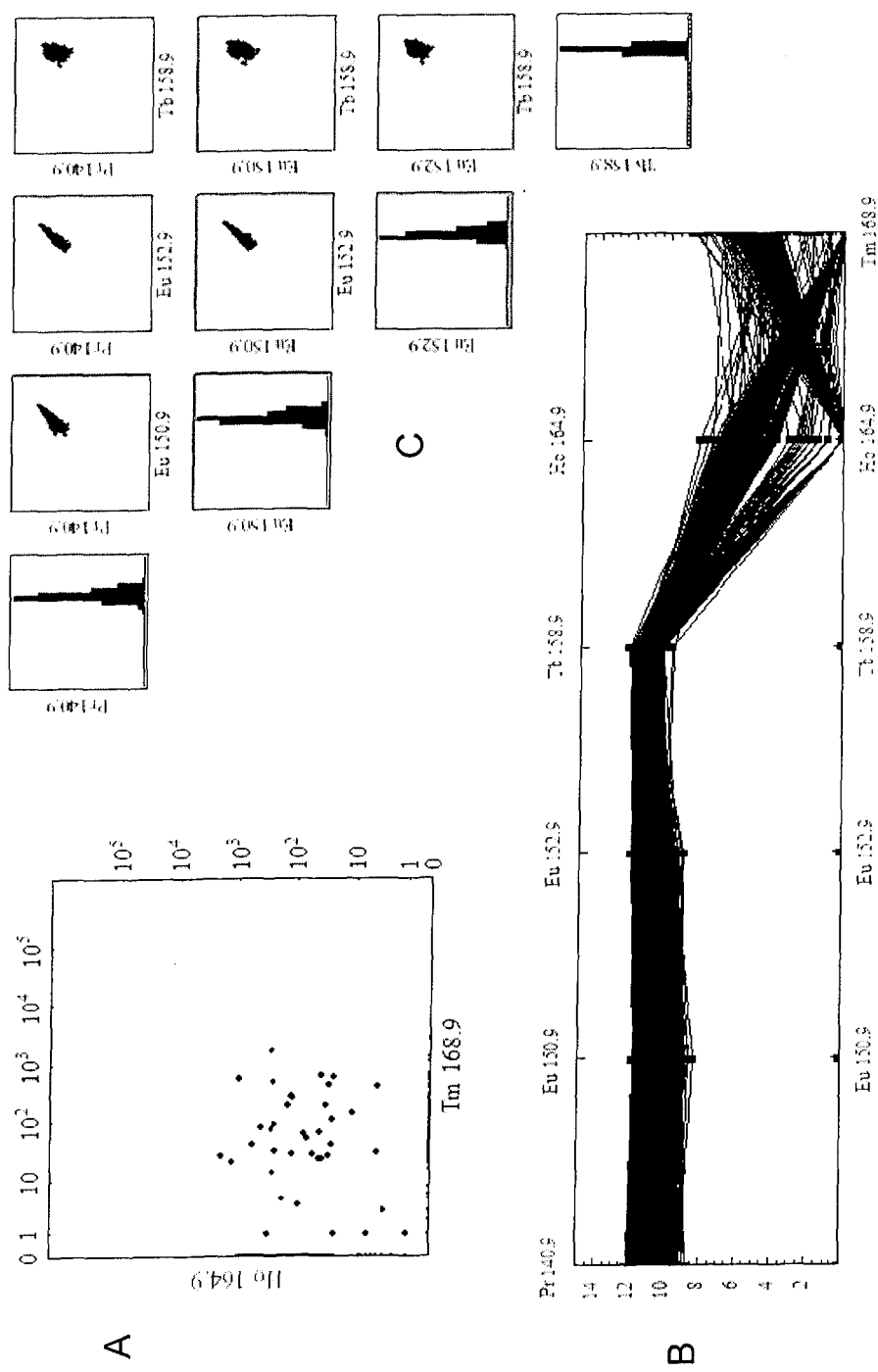

FIG. 16. A. Example of two dimensional Ho/Tm projection obtained as a result of cytometric analysis of Tb, Pr, Eu encoded beads. B. Results of cytometric analysis of Tb, Pr, Eu encoded beads presented in parallel coordinates. Every line represent individual bead. C. Set of two dimensional projections of Tb, Pr, Eu encoded beads analyzed by FC-MS in the multiplexed experiment. The projection scale is based on the inverse hyperbolic sine of the registered signal—modified logarithmic (mLn) scale with nearly linear function on [0,1] interval. The individual beads can be additionally selected according to a criterion which could be chosen on any of possible two dimensional projections or on parallel plot.

Figure 17A:
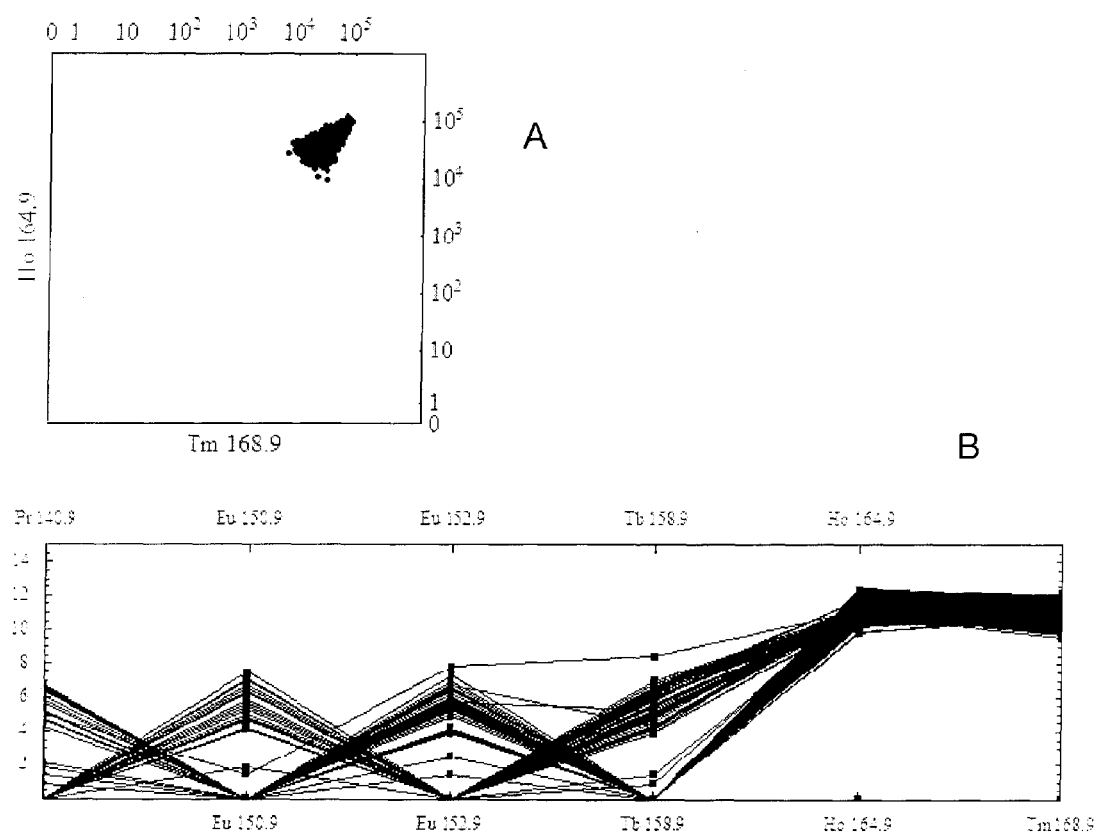

FIG. 17a. A. The two dimensional Ho/Tm projection obtained as a result of cytometric analysis of Tm, Ho encoded beads. B. Results of cytometric analysis of Tm, Ho encoded beads presented in parallel coordinates. Every line represents an individual bead.

Figure 17:
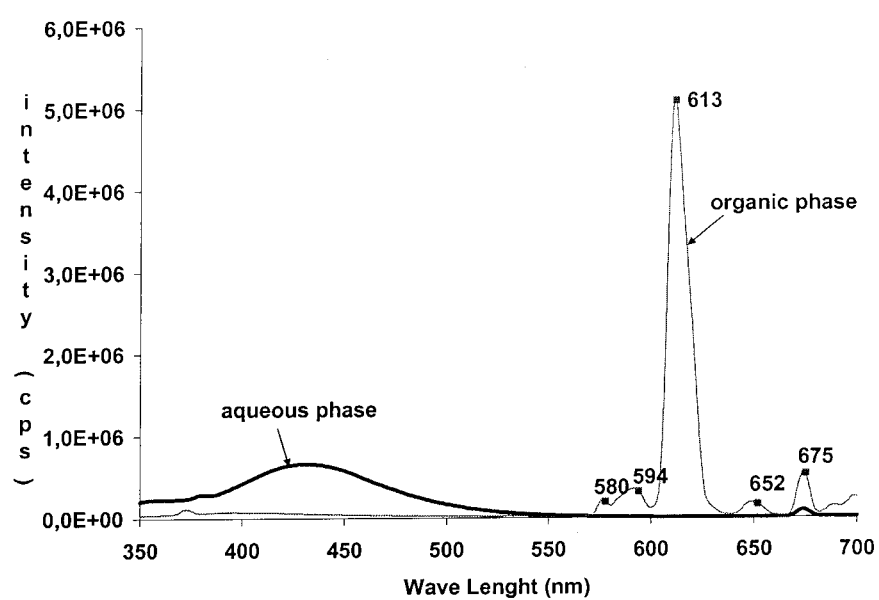

FIG. 17. Fluorescence spectrum of the serum (phase aqueous of CV16) and the THF solution (dissolved polystyrene particles of CV16). The CV16 latex sample contains 16.6% wt polystyrene particles loaded with europium complex (45.8 mg/g of styrene). It is produced by miniemulsion polymerization stabilized with SDS (5% wt/styrene) and initiated with KPS (1% wt/wt styrene).

Figure 18:
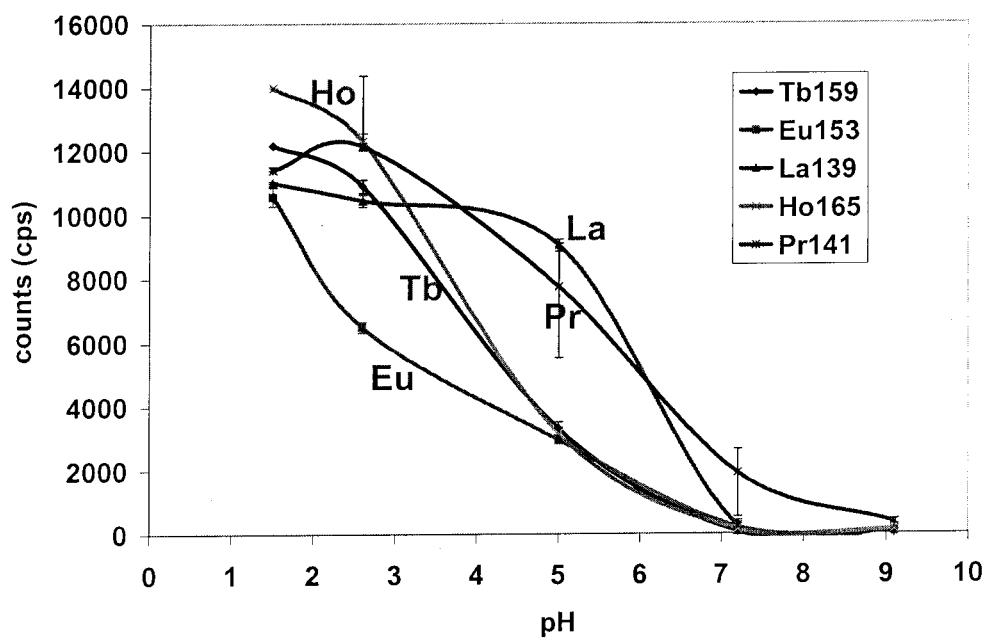

FIG. 18. Counts of lanthanides measured during ICP-MS measurements on CV90 serum versus pH. The CV90 latex sample was composed of non-crosslinked polystyrene particles containing 25 mg each/g styrene of Eu, Tb, Ho, Pr and La complexes. The particle dispersion was maintained at the pH indicated for 48 h before separating the serum from the particles.

Figure 19:
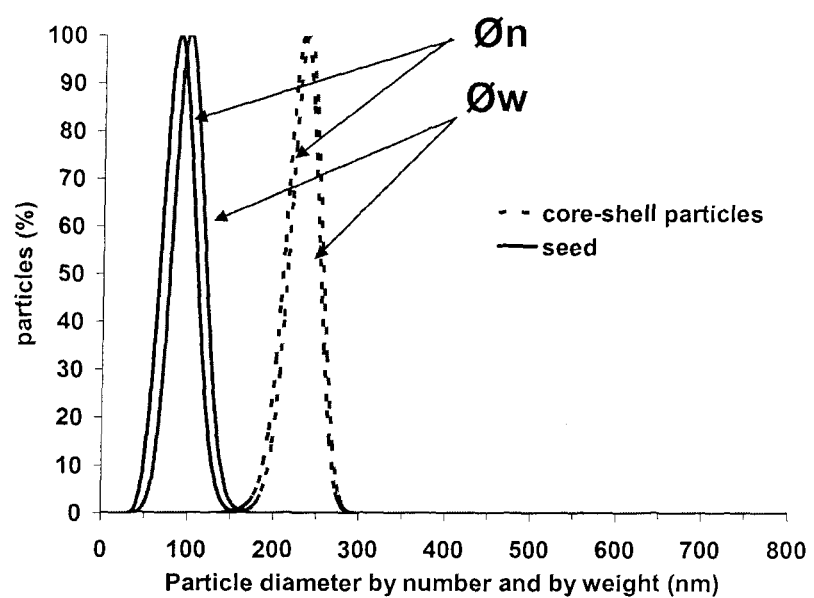

FIG. 19. CHDF spectra of the core (solid lines) and the core/shell particles (dash lines) synthesized by seeded emulsion with a reduced SDS concentration (1% wt/wt monomer).

Figure 20:
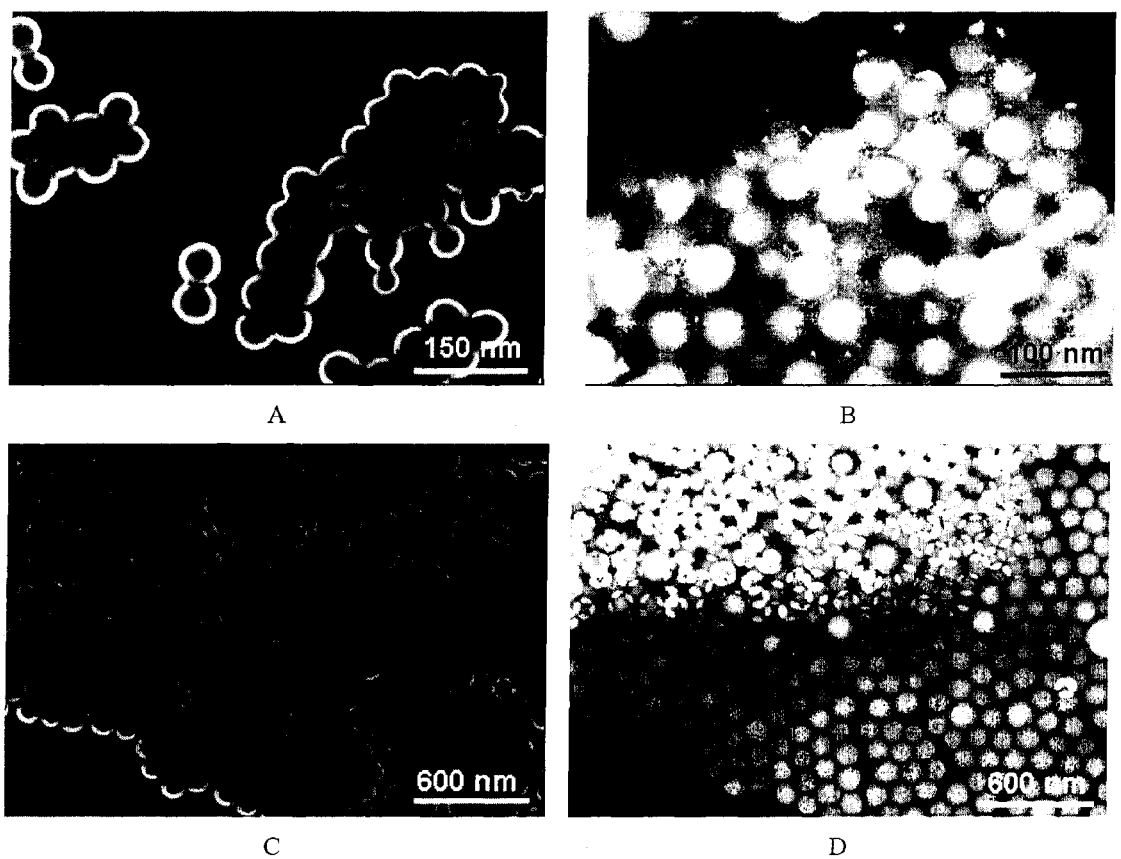

FIG. 20. SEM image of: A—the seed (cv21) and C—the core-shell particles (cv85). Dark-field TEM image of: B—the seed (cv21) and D—the core-shell particles (cv85). The CV21 seeds are polystyrene particles containing europium complex (167 mg/g of styrene) and the core-shell particles CV85 are synthesized by seeded emulsion with a reduced SDS concentration (1% wt/wt monomer).

Figure 20A:
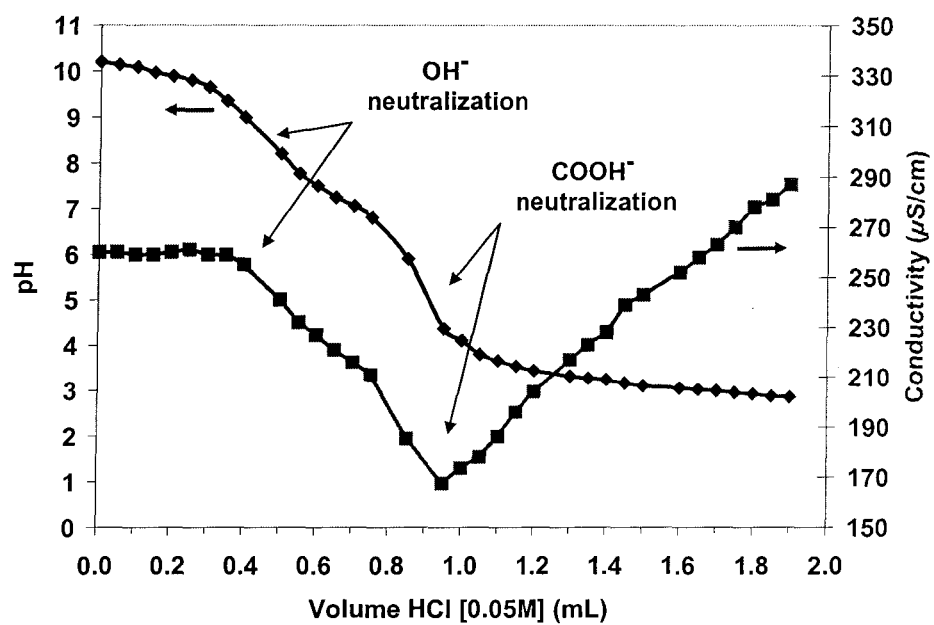

FIG. 20a. Potentiometric (♦) and conductimetric (■) back-titration of methacrylic acid groups at the surface of lanthanide-containing latex particles CV118 (Pr, Ho, La, Tb, Eu 25 mg/g styrene of each). A small excess of base (0.050 M NaOH was first added to the ion-exchanged dispersion, and then the solution was back-titrated with 0.050 M HCl solution.

FIG. 21. The Carboxyl and Amino functionalized shell of the particles.
The exact ratio of reactive functions present on surface of the particles have to be titrated by pHmetry, conductimetry and/or ζ-potential measurement. The biomolecules will be attached to the particle functional groups preferably in molar ratio 1:1; although different molar ratio up to several hundreds functional groups per single biomolecule is also possible and functional.

Figure 22:
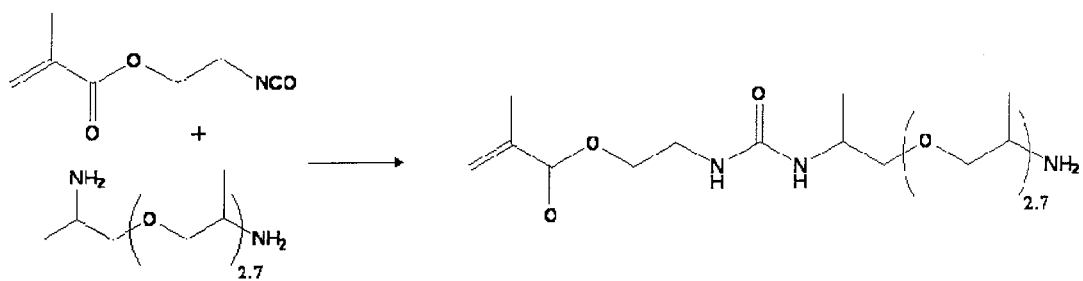

FIG. 22. Schematic representation of synthesis of the amino functional monomers with a water soluble spacer.

Figure 23:
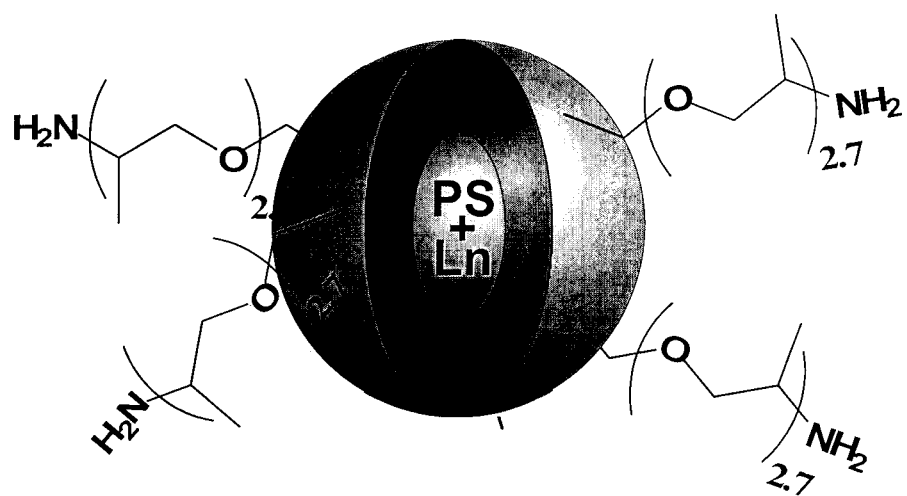

FIG. 23. Schematic representation of the Amino propylene oxide functionalized shell of the particles.

Figure 24:
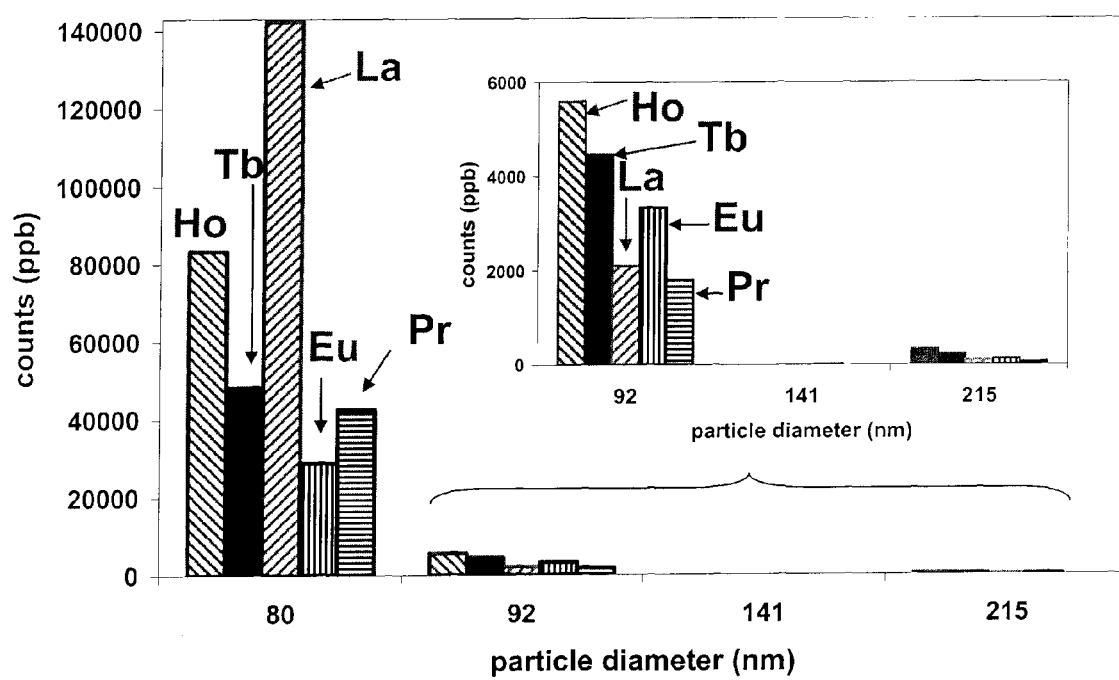

FIG. 24. Counts of lanthanides $^{153}$Eu, $^{165}$Ho, $^{141}$Pr, $^{159}$Tb and $^{139}$La measured during ICP-MS measurements on CV116, CV117, CV118 and CV119 serum at pH=±5 versus the diameter of the particles. These latex samples are composed of particles containing 25 mg each/g styrene of Eu, Tb, Ho, Pr and La complexes.

Figure 25:
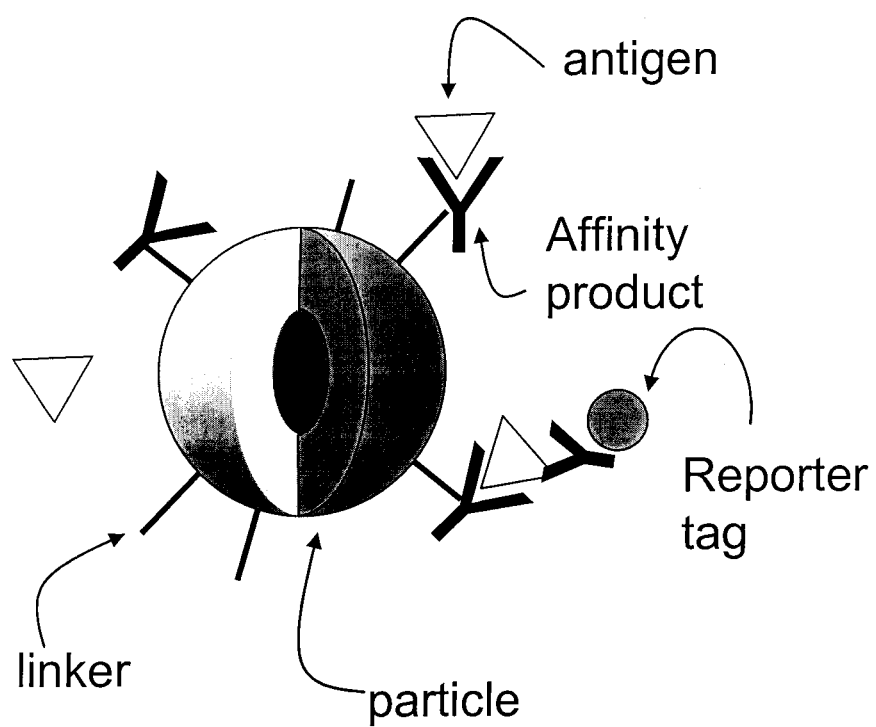

FIG. 25. Schematic representation of the relationship between the element encoded particle, the affinity product and the antigen molecule.

DETAILED DESCRIPTION OF INVENTION

Definitions

"Elemental analysis" is a process where a sample is analyzed for its elemental composition and sometimes isotopic composition. Elemental analysis can be accomplished by a number of methods, including but not limited to:

optical atomic spectroscopy, such as flame atomic absorption, graphite furnace atomic absorption, and inductively coupled plasma atomic emission, which probe the outer electronic structure of atoms;

mass spectrometric atomic spectroscopy, such as inductively coupled mass spectrometry, which probes the mass of atoms;

X-ray fluorescence, particle induced x-ray emission, x-ray photoelectron spectroscopy, and Auger electron spectroscopy which probes the inner electronic structure of atoms.

"Elemental analyzer" is an instrument for the quantitation of the atomic composition of a sample employing one of the methods of elemental analysis.

"Particle (or suspension) elemental analysis" is a process where an analyzed sample, composed of particles dispersed in a liquid (beads in buffer, for example), is interrogated in such manner that the elemental composition is recorded for individual particles (bead-by-bead, for example). An example of the analytical instrument is a mass spectrometer-based flow cytometer (FC-MS)[1].

"Volume (or homogeneous) elemental analysis" is a process where an analyzed sample is interrogated in such manner that the atomic composition is averaged over the entire volume of the sample.

"An internal standard" is defined as a known amount of a compound, different from analyte that is added to the unknown. Signal from analyte is compared with signal from the internal standard to determine how much analyte is present. An internal standard may be used when performing mass spectrometry quantitation. An internal standard can be also used by other means known to those skilled in the art.

"Biological sample" refers to any sample of a biological nature, or any sample suspected of comprising a biological sample, that requires analysis. For example, it may include biological molecules, tissue, fluid, and cells of an animal, plant, fungus, or bacteria. It also includes molecules of viral origin. Typical samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Another typical source of biological samples are viruses and cell cultures of animal, plant, bacteria, fungi where gene expression states can be manipulated to explore the relationship among genes. Biological samples may also include solutions of purified biological molecules such as proteins, peptides, antibodies, DNA, RNA, aptamer, polysaccharides, lipids, etc. Other examples are known to those skilled in the art.

"Antibodies" are immunoglobulin glycoprotein molecules. They can be found in serum of animals. Antibodies may be made in mammals such as rabbits, mice, rats, goats, etc., and chicken. Procedures for immunization and elicitation of a high antibody production response in an animal are well known to those skilled in the art and can be found, for example, in Antibodies, A Laboratory Manual, Cold Spring Harbor Laboratory, 1988, pages 92-115. Antibodies may also be made in cell cultures, for example by recombinant DNA methods, such as described in U.S. Pat. No. 4,816,567. Antibodies may be used as whole molecules, half molecules known as Fab' and Fab$^{2'}$ fragments, as monovalent antibodies (combining a light chain and a modified heavy chain), and other examples known in the art.

"Primary antibodies" are antibodies that bind specifically to an antigen. For example, a primary antibody would bind to an antigen after the antigen is injected into an animal capable of an immunogenic response.

"Secondary antibodies" or "secondary affinity reagents" are antibodies or affinity reagents that bind specifically to primary antibodies or affinity reagents or antigens. For example, primary antibodies may be used as the antigen injected into an animal of a different species than the species that produced the primary antibodies. For example, rabbit secondary anti-mouse antibodies were made by immunizing a rabbit with mouse antibodies.

"Antigen" is a substance that stimulates an immune response in the host organism, especially the production of antibodies. Antigens are usually proteins or polysaccharides, but can be any type of molecule, including small molecules (haptens) coupled to a carrier-protein.

"Bio-markers" are antigens or other molecules that are present in the cell volume of a cell and that distinguish that cell amongst a certain population of cells. Biomarkers present on the cell surface of a cell are called cell surface bio-markers that distinguish that cell from other cells.

"Immunoassay" as used herein means an assay in which a bound analyte, such as cellular antigen or bio-marker, is detected by a tagged affinity reagent such as a primary antibody conjugated to a metal tagged polymer.

"Affinity reagent" is a biomolecule capable of tightly binding to its target. The target may be but is not limited to an antigen. For example, an antibody is an affinity reagent that recognizes and binds with high affinity to a specific antigen.

"Tagged affinity reagent" is an affinity reagent (for example, a primary or secondary antibody) that is conjugated to a synthetic tag (moiety) usually, but not always, through a linker group. The tag can be, but is not limited to, a polymer carrier with covalently attached multiple chelating groups. Each chelating group chelate at least one atom of an element or isotope. The sequence and order of the chelation stage depends on the tagging protocol. The synthetic tag moiety can also be a "particle", "microsphere", "nanoparticle", etc (see definition below) that incorporates at least one element, preferably a metal element.

The term "detect" is used in the broadest sense to include both qualitative and quantitative measurements of a specific molecule, herein specific antigens are detected with the help of a tag (for example: labeled antibody).

"Element tag" is a chemical moiety which includes an element or multitude of elements having one or many isotopes attached to a supporting molecular structure. The element tag also comprises the means of attaching the tag to a molecule of interest. Different element tags may be distinguished on the basis of the elemental composition of the tags. A tag may contain many copies of a given isotope and may have a reproducible copy number of each isotope in each tag. An element tag is functionally distinguishable from a multitude of other element tags in the same sample because its elemental or isotopic composition is different from that of the other tags.

An "Element-tagged affinity reagent" is a tagged affinity reagent in which the tag is an element tag. Similary, an "element-tagged secondary affinity reagent" is a secondary affinity reagent that contains an element tag.

"A support" is a surface which has been functionalized by, for example, pyrrole-2,5-dione (maleimido), sulfonic acid anion, or p-(chloromethyl) styrene. A support, for example, may be but is not limited to, a synthetic membrane, bead (polystyrene, agarose, silica, etc), planar surface in plastic microwells, glass slides, reaction tubes, etc. as is known to those skilled in the art.

"ICP-MS" is the Inductively Coupled Plasma Mass Spectrometer a sensitive mass spectrometry based elemental analyzer. Primarily, the ICP-MS configurations are distinguished by mass selecting technique and can be the quadrupole based, time-of-flight (ICP-TOF), magnetic sector (high resolution ICP-MS), and others. There are many commercially available ICP-MS models having a wide spectrum of capabilities and modifications.

A "polymer" is a substance composed of molecules characterized by the multiple repetitions of one or more species of atoms or groups of atoms (constitutional units) linked to each other in amounts sufficient to provide a set of properties that do not vary markedly with the addition or removal of one or a few constitutional units. [IUPAC definition, see E. S. White, J. Chem. Inf. Comput. Sci. 1997, 37, 171-192]. A polymer molecule can be thought of in terms of its backbone, the connected link of atoms that span the length of the molecule, and the pendant groups, attached to the backbone portion of each constituent unit. The pendant groups are often chemically and functionally different from the backbone chain. Pendant groups that have a high affinity for metal ions can act as chelating groups or ligands for those ions.

"Copolymers" are polymers that consist of two or more chemically different constituent units. A "linear polymer" is a polymer characterized by a linear sequence of constituent units. A "block copolymer" is a linear polymer with sequences of constituent units of a common type, joined to sequences of constituent units of a different type. A "branched polymer" is a polymer in which additional polymer chains (the branches) issue from the backbone of the polymer. One commonly refers to the longest linear sequence as the "main chain". A branched polymer in which the chemical composition of the constituent units of the branch chains is different than those of the main chain is called a "graft copolymer".

"Star polymers" have multiple linear polymer chains emanating from a common constituent unit or core. "Hyperbranched polymers" are multiply branched polymers in which the backbone atoms are arranged in the shape of a tree. These polymers are related to "dendrimers", which have three distinguishing architectural features: an initiator core, interior layers (generations) composed of repeating units radially attached to the initiator core, and an exterior surface of terminal functionality attached to the outermost generation. "Dendrimers" differ from hyperbranched polymers by their extraordinary symmetry, high branching, and maximized (telechelic) terminal functionality.

"Particles" means substances, for example microparticles, microspheres, microbeads, nanobeads, nanoparticles, nanospheres, beads or other substances known to those skilled in the art, which can be labeled with a dye in one instance and when bound to the analyte, serve to distinguish one analyte from another in one of their utilities.

"Nanospheres containing detectable elemental code", or "element stained particles" or "element encoded particles" or "element encoded beads" (or in one particular embodiment lanthanide imbibed particles) contain a plurality of elements (or isotopes), which are used to mark a particle. The stain elements are either uniformly diffused throughout the body of said particle or are distributed inside said particle in a manner that results in the distinguishability of differently stained particles by measurement of the elemental composition of the particle in its entirety. Examples are presented in FIGS. 1 and 2.

"Functional groups" are specific groups of atoms within molecules that are responsible for the characteristic chemical reactions of those molecules. The same functional group will undergo the same or similar chemical reaction(s) regardless of the size of the molecule it is a part of.

"Reporter tag" is an elemental tag which is analyzed simultaneously with a multitude of other element tags or the element encoded particles to correlate to each other. The term "Reporter tag" is used in the broadest sense to include both qualitative and quantitative measurements of a specific molecule associated with the reporter tag in the ratio to other tags and elemental codes.

"$^1$H NMR spectra" (Nuclear Magnetic Resonance) were obtained using Varian Unity 400 MHz spectrometer and were referenced to tetramethylsilane (TMS, 0 ppm).

"IR spectra" (Infrared) were obtained using a Nicolet DX FT IR spectrometer as thin films on NaCl plates.

"High-resolution mass spectra" were obtained using a VG 70-250S (double focusing) mass spectrometer at 70 eV.

The "particle diameters and particle diameter dispersities" were measured both with a BI90 particle sizer (Brookhaven Instruments Corporation) at a fixed scattering angle of 90°, and by Capillary Hydrodynamic Fractionation (CHDF) on a CHDF 2000 from Matec instrument. Some samples were examined by variable angle dynamic light scattering.

"Multi angle dynamic light scattering" (DLS) measurements were performed using a wide angle light scattering photometer from ALV. The light source was a JDS Uniphase He—Ne laser ($\lambda$=632.8 nm, 35 mW) emitting vertically polarized light. The cells were placed into the ALV/DLS/SLS-5000 Compact Goniometer System and sat in a vat of thermostated cis-decahydronaphthalene, which matched the index of refraction of the glass cells. The scattered light was detected at a given angle of 90° C. The vat was connected to an F25-HE Jubalo heating circulator, allowing a temperature control of ±0.06° C.

Steady-state "fluorescence measurements" were carried out with a Spex Fluorolog 2 spectrometer. A sample cell with a 1 cm optical path length was used in the front-face configuration to minimize reabsorption of the sample fluorescence.

"Electron microscopy measurements" Scanning Electronic Microscopy (SEM) images and Transmission Electronic Microscopy (TEM) images were obtained with a Hitachi HD2000 microscope. The microscope was also equipped with Energy Dispersive X-ray (EDX) system to carry out direct element microanalysis. To prepare each sample, a small drop of the diluted latex (1 wt %) was placed onto a carbon-coated copper TEM grid (200 mesh, purchased from SPI supplies). Each sample was dried in air.

The "potentiometric titration" was carried out with a Model P25 pH meter (Rose scientific LTD) equipped with an electrode at 22±1° C. The solid content of the latex dispersion for the titration experiments was 1.14 wt %.

The "conductometric titration" on the latex was measured with a Fisher brand conductivity meter (Fisher Scientific) combined with an electrode with a cell constant of $1.0 \text{ cm}^{-1}$. The electrolyte concentration was fixed at 5 mmol NaCl to ensure a minimum conductivity.

"Readable elemental code" or "Mass Spectrometer readable elemental code" or "MS readable elemental code" is the elemental composition incorporated into or onto a particle that, upon elemental analysis of the particle, generates at least one signal that distinguishes that particle from other particles that contain different elemental composition.

"Transition element" means an element having one of the following atomic numbers 21-30, 39-48, 57-80 and 89-92. Transition elements include the rare earth metals, lanthanides and noble metals.

"Lanthanides" are the transition metals with atomic numbers from 57 to 71 including La, Ce, Pr, Nd, Pm, Sm, Eu, Gd, Tb, Dy, Ho, Er, Tm, Yb, Lu.

The phenomenon of "swelling" is observed when, for example, particles that are hydrophobic by nature are placed in a hydrophobic solvent, which may also contain hydrophobic element-containing complex. Swollen particles absorb element-containing complex in their interior or exterior. The phenomenon of swelling can be controlled by incubation time, the particle nature (presence or absence of cross-linking agent, and solvent).

"Organic or inorganic metal complexes" are chemical moeties which incorporate a metal atom or atoms or ion or ions bound to an organic or inorganic ligand or moetie. An example of an organic metal complex is praseodymium tris-4,4,4-trifluoro-1-(2-naphtyl-1,3-butanedione) and an example of an inorganic metal complex is LaF3 nanoparticle (which is an example of a colloidally stable inorganic nanoparticles). Metal containing endohedral fullerenes are another example, although these are generally considered to be intermediate between a pure organic metal complex and an inorganic metal complex.

EXAMPLES

While the foregoing invention has been described in some detail for purposes of clarity and understanding, it will be appreciated by those skilled in the relevant arts, once they have been made familiar with this disclosure that various changes in form and detail can be made without departing from the true scope of the invention in the appended claims. The invention is therefore not to be limited to the exact components or details of methodology or construction set forth above. Except to the extent necessary or inherent in the processes themselves, no particular order to steps or stages of methods or processes described in this disclosure, including the Figures, is intended or implied. In many cases the order of process steps may be varied without changing the purpose, effect, or import of the methods described.

In the examples below, the notation (x % wt/wt styrene) indicates the weight % of a reagent based on styrene in the recipe. The notation (x % wt/wt water) indicates the weight % of a reagent based on the amount of water in the recipe.

Example 1

Synthesis of the Lanthanide complexes (see FIG. 3). In this application the production and utilization of several lanthanide complexes has been demonstrated. The invention comprises these and other lanthanide and other transition metal/elemental complexes, as is known to those skilled in the art. The invention is not limited to the described complexes and includes other than lanthanide complexes. A skilled worker would be able to produce other lanthanide complexes and other transition metal/elemental complexes using the direction provided here and the general knowledge of one of skill in the art.

Europium (III) tris-(4,4,4-trifluoro-1-(2-naphtyl-1,3-butanedione)): 4,4,4-trifluoro-1-(2-naphtyl-1,3-butanedione) (0.8 g, 3 mmol) was dissolved in a mixture of ethanol (75 mL) and ammonium hydroxide (19 mL, 0.3 mol) under vigorous stirring at room temperature. As soon as a yellowish transparent solution was obtained, a solution of europium (III) chloride (0.366 g, 1 mmol) dissolved in deionized water (10 mL) was added drop-wise. The complex instantaneously precipitates. The mixture was kept under stirring for 12 hours. Then, the product was extracted in $CH_2Cl_2$ (50 mL). The organic phase was washed three times with deionized water (50 mL) and dried over $MgSO_4$. After filtration, the solvent was evaporated, and a yellow solid was obtained. It was dried in vacuum oven. (Weight: 2.75 g, Yield: 90-95%, LRMS (EI, m/z) calc. for $C_{42}H_{18}F_9O_6Eu$ ($M^+$) 947.62, found 947.57).

A similar procedure was used to synthesize lanthanum tris-4,4,4-trifluoro-1-(2-naphtyl-1,3-butanedione) (1.70 g, yield: 90%, LRMS (EI, m/z) calc. for $C_{42}H_{18}F_9O_6La$ ($M^+$) 934.56, found 934.54), praseodymium tris-4,4,4-trifluoro-1-(2-naphtyl-1,3-butanedione) (3.48 g, yield: 93%, LRMS (EI, m/z) calc. for $C_{42}H_{18}F_9O_6Pr$ ($M^+$) 936.57, found 936.54), neodymium tris-4,4,4-trifluoro-1-(2-naphtyl-1,3-butanedione) (1.46, yield: 78%, LRMS (EI, m/z) calc. for $C_{42}H_{18}F_9O_6Nd$ ($M^+$) 939.90, found 939.84), samarium tris-4,4,4-trifluoro-1-(2-naphtyl-1,3-butanedione) (3.71 g, yield: 98%, LRMS (EI, m/z) calc. for $C_{42}H_{18}F_9O_6Sm$ ($M^+$) 946.02, found 946.04), terbium tris-4,4,4-trifluoro-1-(2-naphtyl-1,3-butanedione) (3.56 g, yield: 93%, LRMS (EI, m/z) calc. for $C_{42}H_{18}F_9O_6Tb$ ($M^+$) 954.58, found 954.20), dysprosium tris-4,4,4-trifluoro-1-(2-naphtyl-1,3-butanedione) (1.83 g, yield: 96%, LRMS (EI, m/z) calc. for $C_{42}H_{18}F_9O_6Dy$ ($M^+$) 958.16, found 958.12) and holmium tris-4,4,4-trifluoro-1-(2-naphtyl-1,3-butanedione) (2.96 g, yield: 77%, LRMS (EI, m/z) calc. for $C_{42}H_{18}F_9O_6Ho$ ($M^+$) 960.59, found 960.56).

Example 2

A typical recipe to synthesize polystyrene particles loaded with lanthanide complexes is given. Some parameters were varied to assess their effects on particle size and properties.

Up to 1 g of a lanthanide complex or a mixtures of lanthanide complexes were dissolved in a mixture of styrene (6 g), divinylbenzene (DVB, 60 mg, $4.6 \times 10^{-4}$ mol) (1% wt/wt styrene), and lauryl methacrylate (120 mg, $4.6 \times 10^{-4}$ mol) (2% wt/wt styrene). The DVB serves as a cross-linker, and the lauryl methacrylate serves as a copolymerizable osmotic stabilizer. As soon as the complexes were dissolved, this homogeneous phase was mixed with the aqueous phase composed of deionized water (27 g), sodium dodecyl sulfate (SDS, 0.3 g, $1.04 \times 10^{-3}$ mol) (1% wt/wt water and 5% wt/wt styrene), which serves as a surfactant, and sodium bicarbonate ($NaHCO_3$, 0.15 g, $1.78 \times 10^{-3}$ mol). The mixture was emulsified under magnetic stirring for 15 minutes and then the miniemulsion was prepared by ultrasonication with a Branson Digital sonifier model 450 at 60% amplitude for 4 minutes (1 second pulse on, 2 seconds pulse off). During this step the mixture was cooled with ice. Then, the miniemulsion was transferred to a three neck-flask reactor equipped with a condenser and mechanical stirring. The reaction mixture was heated to 70° C., initiated by the addition of potassium persulfate (KPS) (60 mg, $2.22 \times 10^{-4}$ mol, 1% wt/wt styrene) in water (3 ml). The reaction mixture was heated with stirring for 6 hours at 70° C., and then allowed to cool to room temperature. A stable coagulum-free latex suspension (around 36 mL with 16.6% solid content) is obtained and stored at room temperature.

The particles obtained (CV60) containing the europium complex (46 mg/g of styrene) were coagulum free with a narrow size distribution of 0.05 and a mean diameter of 80 nm as described in Table 2 and 3.

Example 3

We teach a series of reactions containing different amounts of the europium or other lanthanide complexes and lauryl methacrylate as listed in Table 3.

The europium complex (150 mg for CV67 and CV68, and 275 mg CV65) or lanthanum complex (150 mg for CV80) were dissolved in a mixture of styrene (6 g) and divinylbenzene (DVB, 60 mg, $4.6 \times 10^{-4}$ mol) (1% wt/wt styrene). No lauryl methacrylate was added. As soon as the complexes were dissolved, this homogeneous phase was mixed with the aqueous phase composed of deionized water (27 g), sodium dodecyl sulfate (SDS, 0.3 g, $1.04 \times 10^{-3}$ mol) (1% wt/wt water and 5% wt/wt styrene) and sodium bicarbonate (NaHCO$_3$, 0.15 g, $1.78 \times 10^{-3}$ mol). The mixture was emulsified under magnetic stirring for 15 minutes and then the miniemulsion was prepared by ultrasonication with a Branson Digital sonifier model 450 at 60% amplitude for 4 minutes (1 second pulse on, 2 seconds pulse off). During this step the mixture was cooled with ice. Then, the miniemulsion was transferred to a three neck-flask reactor equipped with a condenser and mechanical stirring. The reaction mixture was heated to 70° C., initiated by the addition of potassium persulfate (KPS) (60 mg, $2.22 \times 10^{-4}$ mol, 1% wt/wt styrene) in water (3 ml). The reaction mixture was heated with stirring for 6 hours at 70° C., and then allowed to cool to room temperature. Stable coagulum-free latexes suspensions (around 36 mL with 16.6% solid content) were obtained and stored and room temperature. The results of these experiments are shown in Table 2 and 3.

Example 4

This Example is based on the recipe of Example 2, but here the amount of surfactant was varied to control the particle size. Up to 1 g of lanthanide complexes (single metal particles: CV 40 0.25 g Ho complex, CV41 0.25 g Pr complex, CV60 0.275 g Eu complex, CV61 0.277 g Tb complex or CV38, CV39, CV42 and CV43 0.25 g La complex; multi-element particles CV94: 0.15 g Eu, Tb, Ho, Pr and La complexes; and multi-element particles CV97: 0.15 g Eu, 0.075 g Tb, Ho and Pr complexes) were dissolved in a mixture of styrene (6 g), divinylbenzene (DVB, 60 mg, $4.6 \times 10^{-4}$ mol), and lauryl methacrylate (120 mg, $4.6 \times 10^{-4}$ mol) (2% wt/wt styrene). As soon as the complexes were dissolved, this homogeneous phase was mixed with the aqueous phase composed of deionized water (27 g), sodium bicarbonate (NaHCO$_3$, 0.15 g, $1.78 \times 10^{-3}$ mol), and sodium dodecyl sulfate, which was varied from 0.12 g to 0.3 g (from $0.56 \times 10^{-3}$ mol to $1.04 \times 10^{-3}$ mol; from 0.4% to 1% wt/wt water and from 2% to 5% wt/wt styrene). The mixture was emulsified under magnetic stirring for 15 minutes, and then the miniemulsion was prepared by ultrasonication with a Branson Digital sonifier model 450 at 60% amplitude for 4 minutes (1 second pulse on, 2 seconds pulse off). During this step the mixture was cooled with ice. Then, the miniemulsion was transferred to a three neck-flask reactor equipped with a condenser and mechanical stirring. The reaction mixture was heated to 70° C., initiated by the addition of potassium persulfate (KPS) (60 mg, $2.22 \times 10^{-4}$ mol, 1% wt/wt styrene) in water (3 ml). The reaction mixture was heated with stirring for 6 hours at 70° C., and then allowed to cool to room temperature. Stable coagulum-free latexes suspensions (around 36 mL with 16.6% solid content) were obtained and stored and room temperature. The particles obtained (CV38-43, CV60, CV61, CV94 and CV97) were coagulum free. Their mean diameters are reported versus the SDS content in their synthesis in FIG. 5. All the characteristic of those latexes are summarized in Table 2.

The following two examples are based on the recipe of the example 2, in which the water soluble initiator (KPS) is replaced with the 2,2'-azobis (2-methylbutyronitrile) (AMBN), an oil soluble initiator.

Example 5 (cv70)

A miniemulsion polymerization with an oil-soluble initiator without a lanthanide complex. A mixture was prepared of styrene (6 g), divinylbenzene (DVB, 60 mg, $4.6 \times 10^{-4}$ mol) (1% wt/wt styrene), and lauryl methacrylate (120 mg, $4.6 \times 10^{-4}$ mol) (2% wt/wt styrene). The initiator 2,2'-azobis-(2-methylbutyronitrile) (AMBN, 60 mg, $3.12 \times 10^{-4}$ mol, 1% wt/wt styrene) was dissolved in this phase. This solution was mixed with the aqueous phase composed of deionized water (30 g), sodium dodecyl sulfate (SDS, 0.3 g, $1.04 \times 10^{-3}$ mol)(1 wt %/wt water and 5 wt %/wt styrene) and of sodium bicarbonate (NaHCO$_3$, 0.15 g, $1.78 \times 10^{-3}$ mol). The mixture was emulsified under magnetic stirring for 15 minutes and then the miniemulsion was prepared by ultrasonication with a Branson Digital sonifier model 450 at 60% amplitude for 4 minutes (1 second pulse on, 2 seconds pulse off). During this step the mixture was cooled with ice. Then, the miniemulsion was transferred to a three neck-flask reactor equipped with a condenser and mechanical stirring. The reaction was initiated by immersing the reactor flask into an oil bath heated at 70° C. The reaction mixture was heated with stirring for 6 hours at 70° C., and then allowed to cool to room temperature. A stable coagulum-free latex suspension (around 36 mL with 16.6% solid content) is obtained and stored and room temperature.

The particles obtained (CV70) were coagulum free with a narrow size distribution and a mean diameter of 135 nm as described in Tables 2 and 4.

Example 6 (CV71)

Synthesis of europium-containing polystyrene particles by miniemulsion polymerization using an oil-soluble initiator. A mixture was prepared of styrene (6 g), divinylbenzene (DVB, 60 mg, $4.6 \times 10^{-4}$ mol) (1% wt/wt styrene), and lauryl methacrylate (120 mg, $4.6 \times 10^{-4}$ mol) (2% wt/wt styrene). The initiator 2,2'-azobis-(2-methylbutyronitrile) (AMBN, 60 mg, $3.12 \times 10^{-4}$ mol, 1% wt/wt styrene) and the europium complex (150 mg, $1.58 \times 10^{-4}$ mole) were dissolved in this phase. This solution was mixed with the aqueous phase composed of deionized water (30 g), sodium dodecyl sulfate (SDS, 0.3 g, $1.04 \times 10^{-3}$ mol)(1 wt %/wt water and 5 wt %/wt styrene) and sodium bicarbonate (NaHCO$_3$, 0.15 g, $1.78 \times 10^{-3}$ mol). The mixture was emulsified under magnetic stirring for 15 minutes and then the miniemulsion was prepared by ultrasonication with a Branson Digital sonifier model 450 at 60% amplitude for 4 minutes (1 second pulse on, 2 seconds pulse off). During this step the mixture was cooled with ice. Then, the miniemulsion was transferred to a three neck-flask reactor equipped with a condenser and mechanical stirring. The reaction was initiated by immersing the reactor flask into an oil bath heated at 70° C. The reaction mixture was heated with stirring for 6 hours at 70° C., and then allowed to cool to room temperature. A stable coagulum-free latex suspension (around 36 mL with 16.6% solid content) is obtained and stored and room temperature.

The reaction product contained a significant substantial amount of coagulum (ca.70% wt). The particles present in the serum exhibited a broad size distribution as shown in the CHDF trace in FIG. 6 and the SEM image in FIG. 7.

Example 7 (cv74)

Synthesis of europium-containing styrene-methacrylic acid copolymer particles by miniemulsion polymerization using an oil-soluble initiator. A mixture was prepared of styrene (6 g), divinylbenzene (DVB, 60 mg, $4.6 \times 10^{-4}$ mol) (1% wt/wt styrene), Methacrylic acid (MAA, 60 mg, $7.0 \times 10^{-4}$ mol) (1% wt/wt styrene) and lauryl methacrylate (120 mg, $4.6 \times 10^{-4}$ mol) (2% wt/wt styrene). To this was added 2,2'-azobis (2-methylbutyronitrile) (AMBN, 60 mg, $3.12 \times 10^{-4}$ mol, 1% wt/wt styrene) and the europium complex (150 mg, $1.58 \times 10^{-4}$ mole). As soon as the complex dissolved, this homogeneous phase was mixed with the aqueous phase composed of deionized water (27 g), sodium dodecyl sulfate (SDS, 0.3 g, $1.04 \times 10^{-3}$ mol) (1% wt/wt water and 5% wt/wt styrene) and sodium bicarbonate (NaHCO$_3$, 0.15 g, $1.78 \times 10^{-3}$ mol). The mixture was emulsified under magnetic stirring for 15 minutes, and then the miniemulsion was prepared by ultrasonication with a Branson Digital sonifier model 450 at 60% amplitude for 4 minutes (1 second pulse on, 2 seconds pulse off). During this step the mixture was cooled with ice. Then, the miniemulsion was transferred to a three neck-flask reactor equipped with a condenser and mechanical stirring. The reaction was initiated by immersing the reactor flask into an oil bath heated at 70° C. The reaction mixture was heated with stirring for 6 hours at 70° C., and then allowed to cool to room temperature. A stable coagulum-free latex suspension (around 36 mL with 16.6% solid content) is obtained and stored and room temperature. The particles obtained (CV74) were coagulum free with a narrow size distribution and a mean diameter of 185 nm as shown in the CHDF trace in FIG. 8 and the SEM image in FIG. 9. The characteristics of this sample are listed in Table 2.

Example 8

Influence of the complex concentration on the miniemulsion polymerization. These examples are based on the recipe of Example 2, but here the amount of the europium complex is varied from 14 mg to 1 g. This complex (14 mg for CV13, 275 mg for CV16 and 1 g for CV21) was dissolved in a mixture of styrene (6 g), divinylbenzene (DVB, 60 mg, $4.6 \times 10^{-4}$ mol, 1% wt/wt styrene) (not added in CV16), and lauryl methacrylate (120 mg, $4.6 \times 10^{-4}$ mol) (2% wt/wt styrene). As soon as the complexes were dissolved, each homogeneous phase was mixed with the aqueous phase composed of deionized water (27 g), sodium dodecyl sulfate (SDS, 0.3 g, $1.04 \times 10^{-3}$ mol) (1% wt/wt water and 5% wt/wt styrene) and sodium bicarbonate (NaHCO$_3$, 0.15 g, $1.78 \times 10^{-3}$ mol). The mixture was emulsified under magnetic stirring for 15 minutes and then the miniemulsion was prepared by ultrasonication with a Branson Digital sonifier model 450 at 60% amplitude for 4 minutes (1 second pulse on, 2 seconds pulse off). During this step the mixture was cooled with ice. Then, the miniemulsion was transferred to a three neck-flask reactor equipped with a condenser and mechanical stirring. The reaction mixture was heated to 70° C., initiated by the addition of potassium persulfate (KPS) (60 mg, $2.22 \times 10^{-4}$ mol, 1% wt/wt styrene) in water (3 ml). The reaction mixture was heated with stirring for 6 hours at 70° C., and then allowed to cool to room temperature. Stable coagulum-free latexes suspensions (around 36 mL with 16.6% solid content) were obtained and stored and room temperature. The dispersion of particles with the highest europium content has a yellowish color whereas the two other have the classic white latex appearance. The characteristics of these three samples (CV13, CV16 and CV21) are listed in Table 2.

Example 9

Latex particles containing mixtures of different lanthanide ions. These examples are based on the recipe of Example 2, but here mixtures of the lanthanide complexes were employed, and the amounts of these complexes were varied from 80 mg to 750 mg. A mixture of lanthanide complexes [Pr (20 mg), Ho (20 mg), La (20 mg) and Tb (20 mg) for CV82], [Pr (150 mg), Ho (150 mg), La (150 mg), Tb (150 mg) and Eu (150 mg) for CV90], [Pr (75 mg), Ho (75 mg), Tb (75 mg), Eu (150 mg) for CV97], and [Pr (150 mg), Ho (150 mg), La (150 mg), Tb (150 mg) and Eu (150 mg) for CV116)] were dissolved in a mixture of styrene (6 g), divinylbenzene (DVB, 60 mg, $4.6 \times 10^{-4}$ mol, 1% wt/wt styrene) (not added for CV90), and lauryl methacrylate (120 mg, $4.6 \times 10^{-4}$ mol) (2% wt/wt styrene). As soon as the complexes were dissolved, this homogeneous phase was mixed with the aqueous phase composed of deionized water (27 g), sodium dodecyl sulfate (SDS, 0.3 g, $1.04 \times 10^{-3}$ mol) (1% wt/wt water and 5% wt/wt styrene) and sodium bicarbonate (NaHCO$_3$, 0.15 g, $1.78 \times 10^{-3}$ mol). The mixture was emulsified under magnetic stirring for 15 minutes and then the miniemulsion was prepared by ultrasonication with a Branson Digital sonifier model 450 at 60% amplitude for 4 minutes (1 second pulse on, 2 seconds pulse off). During this step, the mixture was cooled with ice. Then, the miniemulsion was transferred to a three neck-flask reactor equipped with a condenser and mechanical stirring. The reaction mixture was heated to 70° C., initiated by the addition of potassium persulfate (KPS) (60 mg, $2.22 \times 10^{-4}$ mol, 1% wt/wt styrene) in water (3 ml). The reaction mixture was heated with stirring for 6 hours at 70° C., and then allowed to cool to room temperature. Stable coagulum-free latexes suspensions (around 36 mL with 16.6% solid content) were obtained and stored and room temperature. This recipe gave particles with a mean diameter of 91 nm (see sample CV82 in Table 2). The recipes for other reactions run in accord with this example (samples CV90, CV97 and CV116) and the properties of the particles obtained are described in Tables 2 and 5.

Example 10

A miniemulsion polymerization with the Europium complex but without a crosslinking agent (CV16). This example is based on the recipe of Example 2, but here no divinylbenzene cross-linker was employed. The europium complex (275 mg) was dissolved in dissolved in a mixture of styrene (6 g) and lauryl methacrylate (120 mg, $4.6 \times 10^{-4}$ mol) (2% wt/wt styrene). As soon as the complex dissolved, this homogeneous phase was mixed with the aqueous phase composed of deionized water (27 g), sodium dodecyl sulfate (SDS, 0.3 g, $1.04 \times 10^{-3}$ mol) (1% wt/wt water and 5% wt/wt styrene) and sodium bicarbonate (NaHCO$_3$, 0.15 g, $1.78 \times 10^{-3}$ mol). The mixture was emulsified under magnetic stirring for 15 minutes and then the miniemulsion was prepared by ultrasonication with a Branson Digital sonifier model 450 at 60% amplitude for 4 minutes (1 second pulse on, 2 seconds pulse off). During this step, the mixture was cooled with ice. Then, the miniemulsion was transferred to a three neck-flask reactor equipped with a condenser and mechanical stirring. The reaction mixture was heated to 70° C., initiated by the addition of potassium persulfate (KPS) (60 mg, $2.22 \times 10^{-4}$ mol, 1% wt/wt styrene) in water (3 ml). The reaction mixture was heated with stirring for 6 hours at 70° C., and then allowed to cool to room temperature. A stable coagulum-free latex suspension (around 36 mL with 16.6% solid content) is obtained and stored and room temperature. The particles obtained in this way had a mean diameter of 71 nm as indicated as sample CV16 in Table 2. Other characteristics of the particles are also listed in Table 2 as well as other examples run using this recipe and the products obtained.

Example 11

Synthesis of metal-free polystyrene particles by miniemulsion polymerization. This example reports the synthesis of metal-free polystyrene particles (CV64). The recipe was based on the recipe of Example 2, but no lanthanide complex was dissolved in the organic phase, which was composed of a mixture of styrene (6 g) and lauryl methacrylate (120 mg, $4.6 \times 10^{-4}$ mol) (2% wt/wt styrene). Then, this homogeneous phase was mixed with the aqueous phase composed of deionized water (27 g), sodium dodecyl sulfate (SDS, 0.15 g, $0.52 \times 10^{-3}$ mol) (0.5% wt/wt water and 2.5% wt/wt styrene) and sodium bicarbonate ($NaHCO_3$, 0.15 g, $1.78 \times 10^{-3}$ mol). The mixture was emulsified under magnetic stirring for 15 minutes and then the miniemulsion was prepared by ultrasonication with a Branson Digital sonifier model 450 at 60% amplitude for 4 minutes (1 second pulse on, 2 seconds pulse off). During this step, the mixture was cooled with ice. Then, the miniemulsion was transferred to a three neck-flask reactor equipped with a condenser and mechanical stirring. The reaction mixture was heated to 70° C., initiated by the addition of potassium persulfate (KPS) (60 mg, $2.22 \times 10^{-4}$ mol, 1% wt/wt styrene) in water (3 ml). The reaction mixture was heated with stirring for 6 hours at 70° C., and then allowed to cool to room temperature.

A stable coagulum-free latex suspension (around 36 mL with 16.6 wt % solids content) was obtained. This sample was stored at room temperature. The particles obtained in this way had a mean diameter of 104 nm. Other characteristics of the particles are also listed in Table 2.

These particles are used in this description of the invention for comparative purposes, as a auxiliary information in characterization of the matter of invention, and as an example of prior art well known for skilled practitioners.

Example 12

Comparison of the colloidal stability of lanthanide-containing polystyrene particles and metal-free polystyrene particles as a function of pH. The colloidal stability as a function of pH at room temperature of a multi-element lanthanide-loaded particles CV90 ($d_m$=134 nm, Eu, Tb, Ho, Pr and La complexes 25 mg of each/g of styrene) was compared with that of a metal-free particles CV64 ($d_m$=104 nm). These samples were first diluted 5-fold with water. The two diluted latex were stable at pH=9. Five samples were prepared in different vials. The pH of these latexes was slowly decreased by addition of HCl (0.1 M). The result of this experiment is reported in FIG. 12.

Example 13

Synthesis of carboxylated core-shell particles using the lanthanide-containing particles as a seed. The core particles produced by miniemulsion as described in Examples 2-11 were used as seeds for a second stage emulsion polymerization in which methacrylic acid was used as the source of surface carboxyl groups. Without further purification, the diluted latex (solids content: 3.8%) was placed under a nitrogen atmosphere in a three-neck flask reactor equipped with a condenser and mechanical stirring. The reactants for the second stage are listed in Table 1. They were combined in a 25 ml Erlenmeyer flask, emulsified under magnetic stirring, and then were introduced as an emulsion drop wise via a feeding pump (0.02 ml/min) into the solution of the seed particles heated to 70° C. A stable coagulum-free latex (around 25 mL with 22 wt % solids content) was obtained and stored and room temperature.

The particles of the sample CV81 obtained in this way had a diameter of 204 nm as shown in the CHDF trace in FIG. 19 and as described in Table 2. Other characteristics of the particles are also listed in Table 2. Other examples run using this recipe and the products obtained are listed in Table 2.

An important parameter that had to be adjusted was the surfactant concentration. To obtain stable product, the SDS concentration added in the second stage had to be at least 0.5% wt/wt monomer and no greater than 1% wt/wt monomer. Too little surfactant led to coagulation. Too much surfactant led to secondary nucleation. The same amount of surfactant worked well for lanthanide-containing particles and for metal-free particles. Reactions carried out with less than 1% wt/wt monomer of $NaHCO_3$ led to precipitated particles for lanthanide containing particles.

Example 14

Synthesis of amine-containing core-shell particles using the lanthanide-containing particles as a seed. The synthesis of the shell stage of these core-shell particles was similar to that described in Example 13. The core particles produced by miniemulsion were used as seeds for a second stage emulsion polymerization. Without further purification, the diluted latex (solids content: 3.8%) was placed under a nitrogen atmosphere in a three-neck flask reactor equipped with a condenser and mechanical stirring. The reactants for the second stage are listed in Table 1. They were combined in a 25 ml Erlenmeyer flask. One equivalent of ammonia was added based upon aminoethyl methacrylate hydrochloride, and the mixture was emulsified under magnetic stirring. It was then added as an emulsion drop wise via a feeding pump (0.02 ml/min) into the solution of the seed particles heated to 70° C. Heating and stirring were continued for 6 hours at 70° C. A stable coagulum-free latex suspension (around 35 mL with 7% solid content) is obtained and stored and room temperature. The particles obtained (cv105) were coagulum free with a narrow size distribution and a mean diameter of 133 nm as described in Table 2.

Example 15

Synthesis of a methacrylamide derivative of a bis-aminopolypRopylene glycol. This example describes preparation of a monomethacryate derivative of Jeffamine D-130 [Bis-(2-aminopropyl) polypropyleneglycol (Aldrich, estimated Mn=230 $g.mol^{-1}$)] by reaction with a limiting amount of 2-isocyanatoethyl methacrylate (IEM). A solution of 2-isocyanatoethyl methacrylate (2 g, 12.9 mmol) in $CHCl_3$ (3 ml) was addition drop wise into a solution of Jeffamine D-130 (2.96 g, 12.9 mmol) in $CHCl_3$ (3 ml) cooled in an ice bath during the addition. This reaction was carried out for 12 hours at room temperature. The resulting product evaporated in vacuo to give the transparent viscous oil (5.96 g). $^1$H NMR (400 MHz, CDCl$_3$) δ 6.12 (s, 1H, CH$_2$=C—), 5.557 (s, 1H, CH$_2$=C—), 5.29 (s, 2H, —NH—COR), 4.20 (t, 2H, —COO—CH$_2$), 3.49 (t, 2H, —CH2-NHCONH), 3.13 (m, CH$_2$), 1.93 (s, 3H, CH$_3$—C=C), 1.49 (s, 2H, NH$_2$—R), 1.14 (s, 3H, CH$_3$), 1 (s, CH$_3$). The ratio amine/methacrylate=0.96 was determined by $^1$H NMR.

Example 16

Synthesis of amino-functional particles using methacrylate derivative of a bis-amino-polypropylene glycol. This example employs the methacrylate derivative of Jeffamine D-130 described in Example 15. The core particles produced by miniemulsion (CV97) were used as seeds for a second stage emulsion polymerization. These particles contain praseodymium (6.25 mg), holmium (6.25 mg), terbium (6.25 mg) and europium (12.5 mg) complexes. A sample of CV97 (0.5 g polystyrene in 12.5 g H$_2$O, 3.8% solids), without further purification, were diluted to a solids content of 3.8% in a three-neck flask reactor equipped with a condenser and mechanical stirring. After purging the flask with nitrogen, the second stage monomers were added as an emulsion drop wise via a feeding pump (0.02 ml/min) into the reactor at 70° C. while maintaining a nitrogen atmosphere. This emulsion had an aqueous phase consisting of water (7.8 ml), SDS (50 mg, 1 wt %/wt monomer), NaHCO$_3$ (50 mg, 1 wt %/wt monomer) and KPS (68 mg, $3.2\times10^{-2}$ mol.l$^{-1}$). The organic phase contained styrene (4.9 g, 98 wt %/total monomer), methacrylic monomer based on Jeffamine D-130 (0.1 g, 2% wt/total monomer) and DVB as cross-linker (50 mg, 1 wt %/wt monomer). After introducing a nitrogen atmosphere and heating the mixture to 70° C., the second stage reactants (listed in table 1) were introduced drop-wise via a feeding pump (0.02 mL/min). Heating and stirring were continued for 6 h at 70° C. A stable coagulum-free latex suspension (around 35 mL with 7% solid content) is obtained and stored and room temperature. The particles obtained (CV114) were coagulum free with a narrow size distribution and a mean diameter of 138 nm as described in Table 2.

Example 17

Inductively Coupled Plasma mass spectrometry (ICP-MS) measurements on the latex serum. In order to determined if there was any lanthanide cation release from the polystyrene particles into the water phase (serum). This phase was analyzed by ICP-MS. We examined the aqueous phase following miniemulsion polymerization for two single-element particles (CV92, CV93 and three multi-element particles (CV90, CV94, CV96). CV92 is a cross-linked polystyrene sample prepared with 167 mg Eu complex/g styrene as cited in the example 2, and CV93 refers to a core-shell particle in which a CV92 seed was coated with a styrene-methacrylic acid copolymer as detailed in the example 13. CV90 is a non-crosslinked polystyrene sample prepared with 25 mg each/g styrene of Eu, Tb, Ho, Pr and La complexes as reported in the example 9. CV94 is a cross-linked polystyrene sample prepared with the same amounts of metal complexes as CV90 (example 2). CV96 is a crosslinked polystyrene sample prepared with 31 mg Eu, 13 mg Tb, 26 mg Ho, 12.5 mg Pr and 26 mg La complexes/g styrene (example 2). All these as-prepared samples were synthesized with an initial aqueous phase pH of around 9. Sample CV90 was divided into five portions. Small amounts of aqueous HCl (1 M) were added to four of the samples to adjust the pH to different values (1.5, 2.6, 5 and 7.2). The CV90 samples sit at their various pH values for 48 hours before treatment with NaCl. Aliquots (2 ml) of each as-prepared sample, and the 5 samples of CV90, were diluted by a factor of 5 and then the polystyrene particles were precipitated with NaCl (1 g). The colloidal-free serum were collected after filtration (inorganic membrane filter Anotop 25, 0.02 μm, Whatman) to be analyzed by ICP-MS.

It is well understood in miniemulsion polymerization that one gets smaller particles if one increases the amount of surfactant for the same amount of monomer. We teach that the type and amount of lanthanide present has an effect on particle size and it is unprecedented.

Example 18

Preparation and characterization of NH$_2$, COOH and DTPA functionalized beads. Surface encoding. In yet another instance of the invention a different method of element encoding was demonstarted on commercially available 1.8 μm functionalized polystyrene beads from Bangs Labs (amine- and carboxy-modified). As purchased, the functionalized beads had solid content of 10. wt. % in DIW+0.1% NaN$_3$ buffer (#beads/ml-3.134e10; density 1.050 (g/cm$^3$); surface area 3.17e12 μm$^2$/g). Amine-modified beads were additionally modified by conjugation to DTPA. The beads were suspended in carbonate buffer pH 9.6 and 6-fold excess of DTPA dianhydride was added at room temperature and reacted for 2 hours. Washed several times and re-suspended in carbonate buffer pH 9.6 yielding approximately 0.75e8 beads/100 μl. Lanthanide chloride stock solutions (Tm 169 ppm; Tb 159 ppm; Ho 165 ppm; Pr 141 ppm; Eu 151 ppm) were prepared in 100 mM Tris-HCl, 5 mM NH$_4$OAc pH 8.3 from 1M lanthanide chloride. The following protocol was found to be adequate for surface encoding of functionalized beads: Prepare 0.6 ppm and 6 ppm solutions of Tm, Tb, Ho in Tris-NH$_4$OAc buffer. NH2-beads and COOH-beads and DTPA beads: 4 μl of stock —NH2 and —COOH beads add to 2 ml buffer (~1e8 beads/500 μl); 400 μl DTPA-beads add to 1600 ml buffer (0.75e8beads/500 μl). Distribute bead suspensions into marked epp. tubes-500 ul per tube (1e8 beads). To each tube add 500 μl of 0.6 ppm or 6 ppm lanthanide solutions (final 0.3 ppm and 3 ppm). Place half of the tubes in 80° C. heating block, and keep the other half at RT. Using this protocol three types of encoding were prepared: with two (Tm, Ho) and three (Tb, Pr, Eu)/(Tm, Tb, Ho) elements. Unincorporated excess of lanthanides were washed out using 10 mM NH4OAc, 0.5 mM NaOH pH 7.8. To minimize the variability of surface concentration of encoding elements, beads were added to 0.5 ml of metal solution. Bead suspensions of each type in 100K filters with PBS, then wash with wash buffer (total 4 washes). Finally we added 100 μl HCL to filter top and incubated over night and span filters at 10000×g for 1 min, add 100 μl Ir 1 ppb solution to top (as an internal standard), re-suspend beads and combine with filtrate. Results of ICP-MS analysis are presented in FIG. 15. The DTPA-containing beads retain 3-4 times more elements than the NH2-parent beads as well as the COOH-modified beads when the staining solution contained 3 ppm of each element. Heating beads in lanthanide solution did not increase element binding. Thus, this method is a simple approach to generating classifier bead sets of different element composition. The use of DTPA-functionalized beads ensures that element leaching is at a minimum. We analyzed the same beads after 10 days in storage buffer and determined that the elemental composition of these beads was unchanged.

Example 19

Cytometric analysis of DTPA functionalized beads. In FC-MS analysis every beads is analyzed independently and simultaneously. Encoding elements as well as reporter tags are also analyzed simultaneously and correlate to each other. The direct mini-spray chamber (teflon) was used for sample nebulization employing concentric nebulizer at 0.58 L/min Ar, 30 microliter/min sample intake (syringe pump), 1 mm alumina injector, and 1300 W of plasma forward power. The Time-of-flight sampling rate was fixed at 55 kHz. The elementary sample introduction system used is harsh and encoded beads might be destroyed during nebulization. The sample introduction system used also exhibits large memory effects. Damaged beads and bead fragments were still registered as bead-like events. The same sample was also analyzed in a homogeneous assay as described above. Data presentation of a multi-parametric cytometric experiment presents a separate problem. In FIG. 16 we used two relatively novel data presentation methods: logical scaling and parallel coordinates.

In FIG. 16 C, the scale is analogous to FIG. 16 A but was omitted for graphical clarity. In parallel coordinates, the every bead is presented as its unique trace which goes through all elements measured. It is important to notice that having two almost equally abundant isotopes ($^{151}$Eu 47.8%; $^{153}$Eu 52.2%), europium demonstrates very good correlation between them. Comparable good correlation with Pr is also observed. This correlation is crucial for ensuring reproducibility of bead encoding methodology. The correlation with Tb is more diffuse and we do not have a clear understanding of this phenomenon. As can be seen in FIGS. 16A and 16B, the correlation between Ho and Tm (as well as between Ho/Tm and the encoding elements) is very poor. This observation is important, because background element signatures are very different from encoding/reporting elements and can be used as an additional distinguishing feature. When Ho and Tm are used as encoding elements (see FIG. 17a) the situation is reversed: Tb, Pr, Eu correlate very poorly as should be for background elements.

Synthesis of the Lanthanide complexes. This new labeling is based on stable and distinct isotopes such as those of the lanthanide family, which are inserted in polystyrene particles via miniemulsion polymerization process. For this purpose, the lanthanide must have a high solubility in organic solvents such as $CH_2Cl_2$, $CHCl_3$, toluene or styrene, and to be insoluble in water. For the aromatic derivatives chelation can afterwards be measured by fluorescence. The ligand behaves like an antenna that absorbs the energy and transfers it to the metal which can emit light. Non chelated lanthanide cations are not fluorescent. The invention does not need fluorescent capabilities of chelated metals simplifying recipes. In one instance of the invention, we used trivalent lanthanide cations to form neutral complexes with three ligands corresponding to the deprotonated 4,4,4-trifluoro-1-(2-naphthyl)-1,3-butanedione (pKa=6.1) (see FIG. 3-b).

The naphthalene and the trifluoromethyl groups make the resulting complexes sparingly soluble in water. The ligand and the lanthanide salt were dissolved in a basic solution of ethanol/water. Three equivalents of the deprotonated β-diketone bind to the metal cation. The complex formed is insoluble in the reaction mixture and precipitates. These complexes are soluble in non-polar organic solvents including styrene. It is well understood that miniemulsion polymerization includes the normal range of polymers (acrylates, methacrylates) which can be polymerized by miniemulsion polymerization to yield polymer nanoparticles (latex particles). Our current invention pertains to particles formed by free radical polymerization as a preferable embodiment of the invention. One can imagine using other types of polymerization (ie epoxy particles, polyurethane particles). The idea of this type of synthesis is obvious after our teaching, and we consider this type of accomplishment apparent.

Synthesis of lanthanide containing polystyrene particles. In one embodiment of the invention, the lanthanide-containing polystyrene particles will serve as the core particles in a surface-functional core-shell structure to be used as metal-containing tags for bioassays.

Miniemulsion polymerization is a type of polymerization in which kinetically stabilized colloidal monomer droplets of nanometer dimensions are created by subjecting the reaction mixture to strong shearing forces. The reaction mixture consists of a monomer with limited solubility of water, a surfactant, and monomer-soluble solutes. One such solute is a species of very low water solubility such as hexadecane, cetyl alcohol or lauryl methacrylate to act as an osmotic stabilizer. The surfactant provides protection for the droplets against coalescence. In free radical miniemulsion polymerization, the system contains either a water-soluble initiator such as potassium persulfate, or an oil-soluble initiator such as lauroyl peroxide or an oil-soluble azo initiator. One of the main advantages of miniemulsion polymerization over traditional emulsion polymerization is that problems associated with transport through the aqueous phase of reactants with limited water solubility are eliminated.

In a miniemulsion polymerization, under ideal circumstances, the monomer droplets are small, homogeneous in size and kinetically stable over the reaction time. As they are polymerized, they conserve their identity and yield latex particles whose diameter varies from 30 to 500 nm. The size obtained depends upon the choice of monomer, as well as the selection and amount of surfactant employed. This concept has been widely used to prepare polymer particles containing different kinds of hydrophobic species, such as dyes or inorganic nanoparticles.

For example, Erdem et al.[15] carried out studies of how best to encapsulate titanium oxide nanoparticles within polystyrene particles by miniemulsion polymerization. Their best results were obtained with Degussa P25 powder, consisting of $TiO_2$ particles with a mean diameter $d_m$=29 nm. To render these particles soluble in cyclohexane or styrene, they examined many dispersants. The most effective dispersant was a commercial product OLOA 370 from Chevron Chemical, a polybutene-succinimide pentamine. This dispersant bound much more effectively to Degussa P25 particles than to particles with a hydrophobized surface (Degussa T805) of similar particle dimensions.

Dispersant such as OLOA 370 may be effective in allowing the $LnF_3$ nanoparticles to be incorporated into colloidal polymer particles with sub-micrometer diameters. In the examples of the invention, we dissolve chelated lanthanide ions into styrene and then polymerize the styrene droplets into polystyrene particles. Most reactions were run with 2 wt % lauryl methacrylate (LM) as the osmotic co-stabilizer. The particles size obtained are compared with those produced with the addition of lauryl methacrylate in Table 3.

As one can see in Table 2, for reactions carried out with a minimum of 150 mg of lanthanide complex for 6.0 g styrene, the particle diameters and the polydispersity index remain low and are not very much effected if lauryl methacrylate is present or not. The particle sizes obtained are all smaller for reactions with the lanthanide derivative, both with (CV60) or without (CV65, 67, 68 and 80) lauryl methacrylate, than in the classic miniemulsion (CV28) without lanthanide. Scanning electron microscope (SEM) images of CV65 and CV80 are presented in FIGS. 4a and 4b, respectively. These illustrate the small particle size and uniform size distribution obtained in reactions without lauryl methacrylate.

Varying surfactant concentration in order to modify the particle size. If the concentration of lanthanide chelate in polystyrene is kept constant, then larger polystyrene particles will contain larger numbers of lanthanide ions. In this instance of the invention we modify polystyrene particle size through variation of the amount of SDS surfactant employed in the recipe. In traditional free radical miniemulsion polymerization, the particle size can be varied over a wide range by varying the amount of the surfactant used. Different size ranges can be achieved depending of the type of surfactant and type of monomer used. The surface coverage with SDS depends on the particle size because, during the polymerization, the smaller the droplets are and the more collision they undergo, the denser the coverage of the droplet with surfactant must be to keep the miniemulsion stable.

In the examples of the invention, miniemulsions were prepared with various SDS amounts ranging from 1% to 5% by weight with respect to styrene (i.e. from 0.2% to 1% by weight with respect to water). Only mixtures containing at least about 2 wt % by weight with respect to styrene formed stable miniemulsions. For these mixtures, no coagulum was observed and the resulting polymer particles were small and narrow in size distribution.

In FIG. 5 we plot measured particle diameter versus the amount of SDS, based upon styrene used in the reactions. The diameters were determined by dynamic light scattering using a BI 90 particle sizer. For the particles that do not contain any lanthanide complex, the diameters increased from 50 nm to 130 nm when the SDS amount is decreased from 5 wt % to 1 wt % (based upon styrene). A larger variation is seen for the particles containing the La complex (250 mg in 6 g of styrene) (CV38, CV39, CV42 and CV43). These particle diameters increased from 40 nm to 265 nm when the SDS amount was decreased from 5 wt % to 2 wt %.

Particles synthesized from miniemulsions containing either another lanthanide chelate (CV 40, CV41, CV60 and CV61) or several lanthanide chelates (CV94 and CV97) were much less sensitive to SDS concentration. When the amount of SDS employed was reduced from 5% to 2.5%, their diameters increased from 50 nm to a range of value between 50 nm to 90 nm. Their diameters are below or equal to the diameters of the unloaded particles.

We teach that the particle size can be modified by adjusting the amount of SDS surfactant in the recipe for some of the miniemulsion polymerizations. For miniemulsion droplets containing lanthanides other than La only, the variation in size is relatively small, form 50 to 90 nm (CV 40, CV41, CV60, CV61, CV94 and CV97). For metal-free particles, the size variation is comparable to that reported by Bechtold et al. who observed particle diameter increase from around 60 nm to 120 nm when SDS amount was decreased from 5 wt % to 1 wt %. For the La-chelate-containing particles (CV38, CV39, CV42 and CV43), a much larger range of particle sizes was obtained.

Usage of oil-soluble and water-soluble initiators. The oil-soluble initiators tend to produce larger particles in miniemulsion polymerization than persulfate initiator. In one instance of the present invention, we compared the effect of an oil soluble initiator 2,2'-azobis (2-methylbutyronitrile) (AMBN) on the particle diameter to that of a water-soluble initiator (KPS) in the polymerization of styrene miniemulsions without any lanthanide complex (cv70). In experiments with AMBN, this initiator was dissolved directly in the organic phase before emulsification. The polymerization started as soon as the reactor was heated at 70° C. As in the case of all of the miniemulsion polymerization reactions that we describe here, these reactions were run for 6 hours at 70° C. The initiator amount was kept at 1% by weight with respect to the monomer. Two miniemulsion polymerizations were run under the same conditions (styrene as monomer and SDS 2.5% wt/monomer), one with AMBN, the other with KPS as initiator. The particle diameters and size distributions measured by the BI 90 particle sizer are reported in Table 4. The particles whose polymerization was initiated by AMBN have a larger mean diameter (135 nm) than those initiated by KPS.

Yet in another instance of the invention, miniemulsion polymerizations were carried out in which the dispersed phase contained a europium complex (150 mg), AMBN (60 mg) and styrene (6.0 g) (CV71). This miniemulsion appeared to be unstable during the polymerization. The latex had a low fraction of dispersed particles and most of the polymer was in a coagulum. CHDF analysis of the dispersed fraction (FIG. 6) showed a broad size distribution, and an SEM image of this sample (FIG. 7) confirmed the broad size distribution. While one can imagine that the negative surface charges created by the reaction with sulfate radicals formed by decomposition of the persulfate initiator would help to stabilize the polymer particles, the difference in behavior between the Eu-containing particles and the metal-free particles synthesized with AMBN as the initiator is difficult to explain.

The presence of large particles seen in the SEM images in FIG. 7, with particle diameters ranging from 40 nm to 500 nm, makes it likely that droplet coalescence has occurred during the reaction.

We teach that the miniemulsion polymerizations with AMBN as the initiator which incorporate methacrylic acid (MAA) as a co-monomer and one of the ways to increase the particle surface charge density. In one example of the invention (CV74), methacrylic acid (5 wt % based on styrene) was added to the previous recipe. Upon emulsification, the droplets formed were stable and no coagulum formed during the polymerization reaction. The mean particle diameter measured by the particle sizer BI90 was 185 nm with a polydispersity of 0.096. The CHDF analysis (FIG. 8) shows only one narrow population of particles with a narrow size distribution, a result confirmed by the SEM image in FIG. 9. We infer that when we use AMBN as an oil soluble initiator, a small amount of methacrylic acid should be introduced into the reaction mixture (not exclusively, other stabilizers are also could be used).

The ability to vary and to control the lanthanide content of the polymer particles is an important requirement for particles intended to be used in highly multiplexed bioassays. For a given particle size, increasing this amount leads to a higher lanthanide local concentration. Miniemulsion polymerizations (CV13, CV16, and CV21) were carried out with different amounts of the europium complex, 14 mg, 275 mg, and 1.0 g, respectively, for 6.0 g styrene. These reactions employed KPS (1% wt/wt styrene) as the initiator, 5 wt % SDS based on styrene, and the three reactions produced stable dispersions of polymer particles. The characteristics of these particles are reported in Table 4.

Relatively large numbers of europium atoms can be incorporated into these 60 to 70 nm diameter polystyrene particles. SEM images of these samples are presented in FIG. 11. Although in the examples of the invention 12,400 europium atoms per particles have been demonstrated, it does not limit the invention and for persons skilled in the art, higher concentration of the encoding element is easily achievable according to the invention. This enables a significant dynamic range for detection of lanthanide elements in a multiplexed assay. Accordingly, the invention enables control of the range of numbers of lanthanide atoms incorporated into the particles.

We teach the reaction for producing particles containing different metal ions and preparation of series of particles containing mixture of different lanthanide complexes. These reactions employed KPS as the initiator and 2.5 wt % SDS based on styrene. All of these reactions produced stable dispersions of polymer particles with no coagulum. The characteristics of these particles are reported in Table 5. One can see that there is some variation in particle diameter, with larger particles being formed when the La complex was included in the recipe. Although it is not limiting for the invention, all the reactions gave narrow size distributions. The amount and nature of the lanthanide complexes that can be incorporated into polystyrene particles can be controlled over a significant range of latitude.

Long-term stability of the particles loaded with lanthanide complexes. Over a longer period of time (3 month approximately) some particle flocculation was observed for highly loaded particles. This phenomenon also appeared over a short time (some hours after polymerization) when only a small amount of SDS was employed. In this section, some examples are presented to illustrate this flocculation. An effective solution to this problem will be presented at the end of this section of the invention.

Experiment CV16, carried out with 6.0 g styrene, 275 mg of europium complex, and 30 mg SDS (5 wt %/wt styrene) appeared to give stable particles. Similar results were obtained in experiment CV60, carried out with similar amounts of styrene and europium complex, but in which less than half this amount of SDS was used. When the amount of SDS was reduced to 2 wt %/wt styrene (CV58), the particles flocculated after the polymerization. An SEM image of a flocculated region of the sample is shown in FIG. 11a. We also observed flocculation for the particles highly loaded with europium complex (1.23 g for 6.0 g styrene) which were stabilized by 3 wt %/wt styrene (see FIG. 11b: CV20).

Sufficient charge is necessary to ensure the colloidal stability of the particles. The lanthanide complex concentration in the particles influences this stability, and has its biggest effect at low surfactant concentration (below 2% wt/styrene).

Many parameters were modified to prevent the flocculation of the particles containing lanthanide complex such as introducing methacrylic acid as co-monomer to charge the particle surface or adding more SDS either between sonication and polymerization or after polymerization. The former modification promotes new particle nucleation and broader particle diameter dispersity. The second modification does not avoid particle flocculation.

In cases in which flocculation was a problem, we found that this problem could be overcome by diluting the particle dispersion by a factor of 10 (to ca 1.66% solids) with $NaHCO_3$ (1% wt/wt water) just after polymerization. Samples treated this way have remained colloidally stable for 4 months.

The pH sensitivity of the lanthanide-loaded particles is in accord with the observation that larger amounts of surfactant are needed to provide colloidal stability for these particles than for the metal-free particles. The origin of this effect is not completely clear, but is likely related to protonation of lanthanide complexes near the particle surfaces. The sulfate ($SO_4^-$) ions would be expected to remain dissociated over the pH range where the metal-containing particles lose their colloidal stability (see FIG. 12).

Transmission Electronic Microscopy (TEM) images of metal-complex-containing particles. These images are shown in FIG. 13. FIG. 13A shows a dark-field image of sample CV21 containing 0.17 g Eu complex/g styrene. The sample is somewhat polydisperse, with a few large particles and particles of similar size. A prominent feature of the image is that one can see localized regions of intense brightness inside or on the surface of many of the particles. FIG. 13B shows a dark-field image of sample CV45, containing a smaller amount (46 mg Tb complex/g styrene) of metal complex. The particle size distribution appears to be somewhat more uniform. In this image, there are fewer regions of intense brightness; only one spot can be observed. FIG. 13C shows a bright-field image of sample CV38 containing 42 mg La complex/g styrene. These particles are monodisperse in size with a mean diameter of 240 nm. A prominent characteristic of this image is that one can see localized regions of intense darkness inside most of the particles. In this bright-field image, the highest concentrations of heavy elements are localized in these dark spots. FIGS. 13D and 13E shows respectively a dark-field image of sample CV40 containing Ho complex (42 mg/g styrene) and a dark-field image of sample CV41 containing Pr complex (42 mg/g styrene). The particle size distribution appears to be uniform. In this image, there are very few regions of intense brightness; only one spot in each image can be observed. FIG. 13E shows a dark-field image of sample CV52 containing 46 mg Nd complex/g styrene. The particle size distribution appears uniform. In the image, one can see localized regions of intense brightness inside or on the surface of many of the particles. Whereas the lanthanide complex amount is almost the same as the two previous samples, these regions of intense brightness are more prominent in this image.

In four of the dark-field TEM images (FIGS. 13A, C, E, and F) intense bright spots appear. In corresponding bright-field images, dark spots can be found, but these are somewhat more difficult to see. These spots correspond to sites of high local concentration of heavy metals, and they are often located as patches, or what appear to be protrusions on the particle surfaces. Since the lanthanide complexes were completely soluble in the monomer prior to the reaction, we assume that these bright spots are an indication of demixing that occurred during the polymerization reaction. The extent of demixing is related both to the nature of the lanthanide and to the concentration of lanthanide complex in the particles. For example, sample CV21, which contains 16.7% wt complex/wt styrene, exhibits phase separation, but the fraction of the area due to these intense white spots seen in FIG. 13A is much less than 16.7%. Sample CV45, which contains only 46 mg Tb complex/g styrene does not exhibit these spots, and only traces of spots can be seen for CV38 with 42 mg La/g styrene. The same comments apply to CV40 (42 mg Ho/g styrene) and CV41 (42 mg Pr/g styrene), whereas CV52 (46 mg Nd/g styrene) shows more extensive signs of demixing.

In FIG. 14, we show an SEM image and a TEM image (dark-field) of sample CV90, a multi-element particle prepared with europium, terbium, holmium, praseodymium and lanthanum complexes 25 mg of each/g of styrene. Intense bright spots are visible in the particles on TEM image.

For the luminescence experiments, we examined the sample CV16 described in Example 10 above containing 46 mg Eu complex/g styrene. This sample was prepared in the absence of any cross-linking agent, so that the final polymer could be dissolved in organic solvents. It was prepared with the Eu because the Eu complex undergoes intense photoluminescence following excitation of the naphthalene chromophore in the ligand.

The particle dispersion (10 mL, solid content: 16.6%) was flocculated by addition of 1 g NaCl. The precipitated phase was washed with water, allowed to dry, and then dissolved in tetrahydrofuran (THF). Both the aqueous phase and the polymer in THF (ca. 20% wt/wt THF) were examined by fluorescence spectroscopy for excitation at 340 nm. The emission spectra recorded are presented in FIG. 17. The THF solution had an absorption band at 340 nm and emission bands in the 550 to 700 nm region typical of the Eu complex, including the strong band at 613 nm. In contrast, the fluorescence spectrum of the serum (i.e. the aqueous phase) exhibited no emission characteristic of the Eu complex. These results confirm that the complexes were present in the polystyrene phase but not in the aqueous phase.

The results shown in FIG. 17 would not detect free europium cation in the aqueous phase. To test for free lanthanide ions in the aqueous phase we turned to ICP-MS. Here we examined the aqueous phase following miniemulsion polymerization for two single-element particles (CV92, CV93 and three multi-element particles (CV90, CV94, CV96). CV92 is a cross-linked polystyrene sample prepared with 167 mg Eu complex/g styrene, and CV93 refers to a core-shell particle (see below) in which A CV92 seed was coated with a styrene-methacrylic acid copolymer. CV90 is a non-crosslinked polystyrene sample prepared with 25 mg each/g styrene of Eu, Tb, Ho, Pr and La complexes. CV94 is a cross-linked polystyrene sample prepared with the same amounts of metal complexes as CV90. CV96 is a cross-linked polystyrene sample prepared with 31 mg Eu, 13 mg Tb, 26 mg Ho, 12.5 mg Pr and 26 mg La complexes/g styrene. Sample CV90, with an initial aqueous phase pH of 9.1, was divided into five portions. Small amounts of aqueous HCl (1 M) were added to four of the samples to adjust the pH to the values shown in Table 6. The CV90 samples sat at their various pH values for 48 hours before treatment with NaCl.

Aliquots (2 ml) of each as-prepared sample, and the 5 samples of CV90, were diluted by a factor of 5 and then the polystyrene particles were precipitated with NaCl (1 g). The serum was then injected into the ICP-mass spectrometer. The results of the ICP-MS measurements are collected in Table 6.

The counts of lanthanide detected in the serum of each of the samples in Table 6 are reported in ppb based upon the mass of the latex sample prior to addition of NaCl. They indicate that only tiny fractions of the lanthanide content leak into the aqueous phase upon exposure to acidic pH. For example, the highest counts measured were 14000 ppb of $^{165}$Ho for CV90 exposed to pH 1.5 for 48 h. This value corresponds to a loss of only 0.06% of the total Ho complex introduced into the reaction and incorporated into the polystyrene particles.

These data in Table 9 show only tiny, essentially negligible, traces of lanthanide ions in the water phase for samples CV92 to CV96 (values below the values of the control experiment). Therefore, there is no significant release of lanthanide ions to the water phase during the miniemulsion polymerization reaction, and that these ions are retained entirely within the particles. We note that the counts for Eu found for CV92 is similar in magnitude to that found for the other lanthanides not introduced into this sample. We make a similar observation for the CV90 serum for the sample at basic pH, but the counts for the lanthanide elements increase at acid pH. For $^{141}$Pr, there seems to be an increased amount in the serum even for the sample at pH 7.2. The counts measured by ICP-MS on the CV90 serum are plotted versus pH in FIG. 18.

The increase in counts of lanthanide at low pH means that some lanthanide cations are released into the serum under acidic conditions. Ion release is significant only at pH below 7. This result is consistent with the reported pKa of the ligand of 6.1, and suggests that ion release is caused by protonation of the ligand. The ions that are most easily released into the serum are the largest lanthanide ions, lanthanum and praseodymium, which usually produce the weakest complexes. Examination of Table 6 indicates that even the highest number of counts (14 ppm for Ho at pH 1.5) in the serum, however, is tiny (0.06%) compared to what one would expect if all of the lanthanide ions present in the reaction leached into the serum. This result suggests that only the lanthanide complexes near the surface of the particles can be protonated over the time scale of our experiment and release ions into the aqueous phase.

Therefore, all the lanthanide complexes are well encapsulated into the polystyrene particles. To minimize lanthanide ion release to the serum, these polystyrene particles should be kept at basic pH.

Core-shell particles: encapsulating the metal-rich core

In one instance of the invention, the metal-containing particles required higher surface charge density for colloidal stability and appeared to flocculate at a higher pH than metal-free polystyrene particles. TEM images presented in FIGS. 13 and 14 indicated that phase-separated lanthanide complex could be found at the particle surface. Yet in another aspect of the invention, we teach how to overcome these problems by using the metal-containing particles as seeds in a seeded emulsion polymerization. Our intent is to encapsulate the metal-containing particles as the core in a core-shell structure. Functional groups introduced into the shell polymer will serve as sites for covalent attachment of antibodies or spacer groups to the particle surface.

There is substantial literature on seeded emulsion polymerization. A basic model for this process has been developed by Maxwell et al. [16]. A variety of factors affect the final particle morphology, which can be core-shell, raspberry-like, half-moon, acorn-like or inverted core-shell. The important variables include solubility of the second stage monomer in the seed, monomer feed rate, interfacial energy, and polymer mobility during the polymerization process. These issues are particularly important when the second stage monomer is different from the seed polymer, but are less important when the second stage polymer is very similar in structure to the seed polymer.

In the present invention, we teach a seeded emulsion polymerization, in which the base monomer is styrene, with a co-monomer chosen to provide functional groups for antibody attachment. Useful functionality for this purpose includes amine, aldehyde or carboxylic acid groups. The most straight forward choice is methacrylic acid as a co-monomer to introduce carboxylic acid groups. Other choices are possible to introduce primary amino groups. To maintain uniform composition of the second stage polymer, we feed the second stage monomer into the reactions at a low feed rate (0.02 ml/min), approximating monomer-starved conditions.

In one example of the invention, the CV64 particle as metal-free seed particles was used to optimize the concentration of surfactant to be used in the second-stage monomer addition. Use of too much SDS led to secondary nucleation, easily detected by CHDF as a bimodal particle size distribution, and too little SDS led to particle coagulation. Good results were obtained with 1% wt/wt monomer of SDS (CV81). The SDS was added along with the addition of second stage monomer mixture and this proportion only refers to the amount added during the second stage. The seed were used as-prepared by miniemulsion polymerization. So, the surfactant from the core particle remained during this second step of the synthesis. In FIG. 19 we present the CHDF traces for CV81 before second stage monomer addition and after the second stage polymerization in which was added H2O (5 mL), SDS (50 mg), sodium bicarbonate (NaHCO3, 50 mg), divinylbenezene (DVB, 50 mg), styrene (4.75 g) and methacrylic acid (0.25 g) to a diluted as-prepared miniemulsion (3.8% solid content).

The polystyrene particles used as seed have a diameter of 100 nm and a narrow particles size distribution. The latex of the core/shell particle is composed of only one monodispersed population. The theoretical diameter 230 nm, calculated from the amount of second stage monomer added, is in excellent agreement with the measured diameter (234 nm). The material added in this second stage effectively covers the seed.

The recipe used for this second stage seeded emulsion is valid to produce the functionalized shell of or particle. The amount of SDS was even decreased with success to 0.5% with respect to water in the later experiment.

The shell thickness and TEM images.

In the FIG. 20, we present SEM images and TEM images of metal containing seed particles and the carboxylated core-shell particles synthesized from them. In FIG. 20A we show an SEM image of the seed particles CV21, with a mean diameter of 60 nm used to synthesize the core-shell particles of sample CV85. A dark-field TEM image of these particles is shown in FIG. 20B. An SEM image of CV85 (d=130 nm) is shown in FIG. 20C. These particles exhibit a narrow size distribution. The diameter of the particles is more than doubled during this second step, which means that their volume is multiplied by 8. An indication of the core-shell nature of these particles is given by the dark-field TEM image in FIG. 20D. In FIG. 20B one can note the presence intense white spots in the metal-containing polystyrene seeds. Those spot are no longer visible in the image of the core-shell particles seen in FIG. 20D.

Titration of carboxylic acid on core/shell particles.

The conductimetric and the potentiometric titration were run on metal-free core/shell particles (CV81 and CV83) and on lanthanide-containing particles (CV117, CV118 and CV119) in order to determine the mean number of acid groups per particle at the particle surface. These latexes were purified (ion-exchange resin AG 501-X8 resin, 20-50 dry mesh, 300-1,180 μm wet bead, Bio-Rad) and diluted (1:21, solids content=1.14 wt %) as noted previously. The conductivity after purification was less than 25 μS/cm. A small amount of NaCl (5 mmol) was then added to each dispersion to ensure a minimum conductivity. The pH of these purified latex dispersions was around 4.6-4.9. The latex dispersions were then treated with a small excess of 0.050 M NaOH based upon the amount of methacrylic acid added in the particle synthesis. The dispersions were allowed to remain at basic pH for an hour and then back titrated with 0.050 M HCl. A typical titration curve (for sample CV118) is shown in FIG. 20a. The —COOH content at the particle surface was calculated based upon the end point determined in the back titration monitored by conductivity.

FIG. 20a presents typical potentiometric and conductometric back-titration curves for methacrylic acid-containing core-shell particles. The example shown is for sample CV118 which contains (Pr, Ho, La, Tb, Eu 25 mg/g styrene of each). In the potentiometric titration, the pH versus added volume of HCl curve exhibits two sharp decreases associated with two equivalence points. That at pH≈8.5 corresponds to the neutralization of excess OFF in the solution and that at pH 5 corresponds to neutralization of —COOH groups at the surface of the particles. In the conductivity titration, the conductivity versus added volume of HCl curve also shows these two equivalence points at similar volumes of added HCl. Because the changes in slope of the conductivity traces are sharper and easier to detect than those of the potentiometric titration, we take the equivalence points from the conductivity titrations to calculate the surface acid group content of the particles. Based on this value and the particle diameter and assuming a smooth particle surface, the number of acid groups per square nanometer was also calculated. Those values are reported in Table 8 for metal-free core/shell particles (CV81 and CV83) and lanthanide-containing particles (CV117, CV118 and CV119).

The first two samples CV81 and CV83 are two metal-free core/shell particles with a mean diameter respectively of 204 nm and 206 nm. The mean number of acid group at the surface of each particle was calculated to be around $6.4 \times 10^5$ for CV81 and $0.25 \times 10^5$ for CV83, which corresponds, respectively, to 4.7 and 1.5 —COOH groups per square nanometer. The three other samples composed of lanthanide-containing core/shell particles CV117, CV118 and CV119 have respectively a diameter of 92 nm, 141 nm and 215 nm. They are synthesized with the same seed CV116 (d=80 nm, polydispersity=0.03). The mean number of acid group at the surface of each particle was calculated to be around $0.24 \times 10^5$ for CV117, $1.4 \times 10^5$ for CV118 and $1.8 \times 10^5$ for CV119 which correspond respectively to 0.9, 2.2 and 1.2 —COOH groups per square nanometer. The coverage of carboxylic group at the surface of those particles appears to be independent to the presence of lanthanide complexes in the seed. The number of —COOH per $nm^2$ ranges from 0.9 to 4.7. Assuming that the area occupied by a carboxyl group at the surface of a latex particle of 9 $\text{Å}^2$ (11 —COOH/$nm^2$), the surface coverage with COOH groups ranges from 3% to 42%.

Determining the functional group content of the shell

In preparation of functional core-shell particles, seeded emulsion polymerization reactions were carried out with CV97 as seed. These particles contained praseodymium (12.5 mg), holmium (12.5 mg), terbium (12.5 mg) and europium (25 mg) complexes per g styrene. In CV98, the second stage monomer contained methacrylic acid (MAA, 5% wt/wt total monomer) in styrene, and in CV105, the second stage monomer consisted of 5 wt % 2-aminoethyl methacrylate (AEMA, 5% wt/wt total monomer) in styrene. A total of 5 g of second stage monomer was added to 44 ml of CV97 (1.66 g solids) under monomer starve conditions.

Both reactions gave particle dispersions with a narrow size distribution. The particle diameters measured by the BI90 particle sizer, are reported in Table 7. For the MAA system, the final particle diameter was in accord with that (140 nm) predicted based upon the amount of second stage monomer added. For CV105 (with AEMA), a somewhat smaller mean diameter (133 nm) was determined.

The copolymerization of these monomers with styrene should produce the particles depicted in FIG. 21.

The exact ratio of reactive functions present on surface of the particles have to be titrated by pHmetry, conductimetry and/or ζ-potential measurement. The biomolecules will be attached to the particle functional groups preferably in molar ratio 1:1; although different molar ratio up to several hundreds functional groups per single biomolecule is also possible and functional.

The shell functionality with spacer

Other amino functional monomers with a water soluble spacer are based on 2-Isocyanatoethyl methacrylate and Jeffamine D-130. They are synthesized according to the reaction depicted in FIG. 22 (Example 15).

The isocyanate groups react quickly with amine in chlorinated solvent at room temperature without catalyst. As the isocyanate starving condition is used, the amine is in excess all along the reaction. By this way, the isocyanates react statistically with one of the two amine of the jeffamine. The ratio amine/methacrylate function has been determined by proton NMR ($\delta$=5.6 ppm and $\delta$=5.2 ppm for $CH_2$=CRR' and $\delta$=1.0 ppm $CH_3$—$CH(NH_2)$) respectively equal to 0.96. So the monomer corresponds mainly to the formula of FIG. 22. The fraction of methacrylic monomer not terminated by an amine will not graft the antibody but will improve the particle colloidal stability due to its water solubility. The presence of dimethacrylic compound can not be excluded. It will act as a cross-linker for the shell of the particle.

This monomer, based on jeffamine D-130, was used in a seeded emulsion (example 16, CV114) to design a particle with a water soluble spacer. It was introduced at 2% by weight with respect to total monomer. The seed (CV97, Ø=100 nm) used for this seeded emulsion contain praseodymium (75 mg), holmium (75 mg), terbium (75 mg) and europium (150 mg) complexes.

The particles of the latex are stable and their diameter was measured by the particle sizer BI90 at 138 nm ($Ø_{th}$=140 nm) with a dispersity of 0.04. The titration of the amine function that covers the bead surface (FIG. 23) and the antibodies grafting was successful.

The shell and anti lanthanide-release efficiency.

The first ICP-MS experiments run on the aqueous phase following miniemulsion polymerization of lanthanide containing polystyrene particles show that all the lanthanide complexes are well encapsulated into the polystyrene particles, except that some lanthanide cations are released into the serum under acidic conditions. To test whether the shell of the core-shell particles can prevent the free lanthanide ions' release at acid pH in the aqueous phase we utilized ICP-MS. Here we examined the aqueous phase following miniemulsion polymerization for one multi-element particle CV116 (d=80 nm) prepared with Eu, Ho, Pr, Tb and La complexes (mg of each/g styrene) and the aqueous phase following seeded-emulsion polymerization for three multi-element particle CV117, CV118 and CV118 prepared with a common lanthanide-containing seed (CV116). These samples were produced with various amount of monomer fed in the second stage and their diameters were respectively 92 nm, 141 nm and 215 nm. They were divided into five portions. Small amounts of aqueous HCl (1 M) were added to four of the samples to adjust the pH to the values shown in Table 10. The samples were stored at their various pH values for 72 hours. Then the polystyrene particles were precipitated with NaCl (1 g). The serums were recovered after filtration (inorganic membrane filter, Anotop 25, 0.02 µm, Whatman). The results of the ICP-MS measurements are shown in Table 8.

The counts of lanthanide detected in the serum solution of these samples are reported in ppb, reflecting the low order of magnitude of concentration measured. For example, the highest count measured equal to 142270 ppb on $^{139}$La for CV116 at pH 5.2 corresponds only to 0.57% of the total lanthanum complex introduced prior polymerization. These low concentrations support the conclusion of the previous ICP-MS experiments that all the lanthanide complexes are well encapsulated into the polystyrene particles.

As for the ICP-MS experiments performed on CV90 samples stored at various pH, the lanthanide cations release into the serum is higher under acidic conditions (pH below 7) for the seed CV116: whatever the lanthanide, the counts of lanthanide increase (from 57 ppb to 28970 ppb for $^{153}$Eu). The same observation is available for CV117 with a diameter of 92 nm (from 12 ppb to 3330 ppb for $^{153}$Eu) whereas CV118 and CV119 with a respective diameter of 141 nm and 215 nm show only a weak increase of the lanthanide counts (CV118: from 4 ppb to 615 ppb for $^{153}$Eu, CV119: from 23 ppb to 837 ppb for $^{153}$Eu).

In order to underline the effectiveness of the shell protection effect against lanthanide cation release in the serum in acid condition, the lanthanide counts versus the particle diameter of the four samples at pH of around 5 (highest counts for the seed CV116 at pH=5.2) are reported in FIG. 24.

In the FIG. 24, the first set of bars for the five lanthanide complexes corresponds to the counts measured for each lanthanide, at pH around 5, for the seed. These counts range from around 29000 ppb for the europium cation to more then 142000 ppb for the lanthanum cation. The three following sets of bars correspond respectively to the counts measured for each lanthanide, at pH around 5, for the core/shell particles CV117, CV118 and CV119. All those counts are below 5600 ppb. Accordingly, less release is observed when the lanthanide-containing particles are covered with a shell, even at acid pH. The shell of the core/shell particles fulfills two purposes: (i) it limits the lanthanide cation release and (ii) brings reactive function at the surface of the particles to graft the antibodies.

Among the range of isotopes (167), a series of eight lanthanides, not naturally present in human body either separately or combined in various proportions, have been used to develop distinguishable particles. There is no limitation in the invention to use other elements for element encoding. In yes another instance, according to the invention the particles were covered with a functional shell during a second stage seeded emulsion polymerization. The functionality of this shell is either carboxylic group (MAA) or amine group with (methacrylic monomer based on jeffamine D-130) or without (AEMA) spacer. To be specific for antigen of interest, the element encoded particles have to be covalently linked to specific biomolecule, for example an antibody that corresponds to the bioactive part of particle (see FIG. 25).

REFERENCE LIST

[1] Bandura, D. R.; Baranov, V., I; Tanner, S. Elemental flow cytometer, e.g. mass spectrometer or optical emission spectrometer based cytometer used in, e.g. health science, food sciences, environmental sciences, and genomics and proteomics, has spectrometer. US2005218319-A1; WO2005093784-A1, 2006.

[2] Baranov, V.; Tanner, S.; Bandura, D.; Quinn, Z. Kit for detecting/measuring transition element, comprising tag having transition element for tagging biologically active material and instruction for tagging material, combining tagged material with analyte, detecting/measuring elements. US2004072250-A1; WO2005003767-A2, 2006.

[3] V. I. Baranov, D. R. Bandura, S. D. Tanner, ICP-MS as an elemental detector in immunoassays. Speciation without chromatography, European Winter Conference on Plasma Spectrochemistry, Hafjell, Norway 2001) Book of Abstracts, p. 85.—

[4] V. I. Baranov, Z. Quinn, D. R. Bandura, S. D. Tanner, A sensitive and quantitative element-tagged immunoassay with ICPMS detection, Anal. Chem. 74 (2002) 1629-1636.

[5] V. I. Baranov, Z. A. Quinn, D. R. Bandura, S. D. Tanner, The potential for elemental analysis in biotechnology, J. Anal. Atom. Spectrom. 17 (2002) 1148-1152.

[6] Z. A. Quinn, V. I. Baranov, S. D. Tanner, J. L. Wrana, Simultaneous determination of proteins using an element-tagged immunoassay coupled with ICP-MS detection, J. Anal. Atom. Spectrom. 17 (2002) 892-896.

[7] Chandler, D.; Chandler, V.; Lambert, B.; Reber, J.; Phipps, S.; Van, C. A.; Chandler, D. J.; Lambert, B. A.; Reber, J. J.; Phipps, S. L.; Chandler, V. S, New precision fluorescently dyed particles with two fluorescent dyes. WO9919515-A; EP1023464-A; WO9919515-A1; AU9910809-A; EP1023464-A1; HU200003986-A2; KR2001031140-A; JP2001520323-W; U.S. Pat. No. 6,514,295-B1; US2003028981-A1; U.S. Pat. Nos. 6,599,331-B2; 6,632,526-B1; US2004053052-A1; IL135593-A; U.S. Pat. No. 6,929,859-B2; US2005260676-A1.

[8] Cheung, S. W. Prodn. of fluorescent microspheres, useful as labels in fluorescence microscopy—by reacting acrylic! latex beads having surface ester! functions with amine!-terminated fluorescent dye and di:amine spacer mols. U.S. Pat. No. 5,194,300-A.

[9] Schwartz, A.; Repollet, E. F. Uniform micro-bead population—contg. one or more fluorescent dyes for alignment of flow cytometer or fluorescence microscope over range of wavelengths. EP511314-A; U.S. Pat. No. 5,073,498-A; JP94084969-B2; EP511314-A4.

[10] Fulwyler, M. J. Automatic sorting of cell sub-populations—using antibodies labelled with two different fluorochrome(s). DE3331017-A1; DE3331017-A; GB2126341-A; FR2532431-A; JP59060261-A; U.S. Pat. No. 4,499,052-A; GB2126341-B; DE3331017-C; U.S. Pat. No. 4,717,655-A; JP92047265-B.

[11] Kuhn, M.; Wells, K. S.; Zhang, Y. Z.; Kang, H. C.; Brinkley, J. M.; Haugland, R. P. Di:pyrro-methene-boron di:fluoride labelled fluorescent microparticles—useful for standardisation of instrumentation, as biological tracers and in detection and analysis of biomolecules. U.S. Pat. No. 5,723,218-A.

[12] Chandler, V. S.; Fulton, R. J.; Chandler, M. B.; Fulton, J. R.; Chandler, D. J. Bead-sets for simultaneous assay of multiple analytes by cytometric analysis—comprise many subsets carrying specific reagent and identifiable from all other subsets by fluorescence parameters, especially for clinical assays, and detecting gene mutation. WO9714028-A; WO9714028-A2; AU9673989-A; U.S. Pat. No. 5,736,330-A; EP852004-A2; U.S. Pat. Nos. 5,981,180-A; 6,057,107-A; 6,449,562-B1; 6,524,793-B1; US2004059519-A1; US2005118574-A1; U.S. Pat. No. 6,939,720-B2; US2005164261-A1; US2005202469-A1.

[13] Wang, C. G. Specific immunoassay method using labelled mobile reagent particles—esp. polystyrene latex, forming complex with analyte. U.S. Pat. No. 4,454,233-A.

[14] L. P. Ramirez, M. Antonietti, K. Landfester, Formation of novel layered nanostructures from lanthanide-complexes by secondary interactions with ligating monomers in miniemulsion droplets, Macromolecular Chemistry and Physics 207 (2006) 160-165.

[15] B. Erdem, E. D. Sudol, V. L. Dimonie, M. S. El-Aasser, Encapsulation of inorganic particles via miniemulsion polymerization. I. Dispersion of titanium dioxide particles in organic media using OLOA 370 as stabilizer, Journal of Polymer Science Part A-Polymer Chemistry 38 (2000) 4419-4430.

[16] I. A. Maxwell, B. R. Morrison, D. H. Napper, R. G. Gilbert, Entry of Free-Radicals Into Latex-Particles in Emulsion Polymerization, Macromolecules 24 (1991) 1629-1640.

TABLE 1

Reactants for the second stage of the stage emulsion polymerization for all the examples.

| Second-stage reactants | Example 13 amounts | Example 14 amounts | Example 16 Amounts |
|---|---|---|---|
| seed particles (0.5 g/12.5 g H2O, 3.8% solids) | 13 ml | 13 ml | 13 ml |
| Water | 5.0 ml | 5.0 ml | 5.0 mL |
| SDS | 25 mg | 25 mg | 50 mg |
| NaHCO3 | 50 mg | 50 mg | 50 mg |
| ammonia (aqueous, 30 wt %) | — | 0.30 g | — |
| potassium persulfate (KPS) | 68 mg | 68 mg | 68 mg |
| Styrene | 4.75 g | 4.75 g | 4.9 g |
| divinylbenzene (DVB) | 50 mg | 50 mg | 50 mg |
| methacrylic acid (MAA) | 0.25 g | — | — |
| 2-aminoethyl methacrylate hydrochloride (AEMA) | — | 0.25 g | — |
| methacrylic monomer based on Jeffamine D-130 | — | — | 0.1 g |

TABLE 2

Characteristics of the latexes synthesized as described in Examples 2 to 17.

| Example | Sample | Volume (mL) | Latex solids content (wt %) | Diameter (nm) $^a$ | PDI $^a$ | Ln complex (mg/g styrene) | Surface functionality |
|---|---|---|---|---|---|---|---|
| 2 | CV60 | 36 | 16.6 | 80 | 0.05 | Eu (46) | — |
| 3 | CV65 | 36 | 16.6 | 73 | 0.09 | Eu (46) | — |
|   | CV67 | 36 | 16.6 | 70 | 0.14 | Eu (25) | — |

TABLE 2-continued

Characteristics of the latexes synthesized as described in Examples 2 to 17.

| Example | Sample | Volume (mL) | Latex solids content (wt %) | Diameter (nm)$^a$ | PDI$^a$ | Ln complex (mg/g styrene) | Surface functionality |
|---|---|---|---|---|---|---|---|
| | CV68 | 36 | 16.6 | 74 | 0.14 | Eu (25) | — |
| | CV80 | 36 | 16.6 | 75 | 0.05 | La (25) | — |
| 4 | CV38 | 36 | 16.6 | 273 | 0.13 | La (42) | — |
| | CV39 | 36 | 16.6 | 65 | 0.02 | La (42) | — |
| | CV40 | 36 | 16.6 | 71 | 0.15 | Ho (42) | — |
| | CV41 | 36 | 16.6 | 84 | 0.02 | Pr (42) | — |
| | CV42 | 36 | 16.6 | 143 | 0.08 | La (42) | — |
| | CV43 | 36 | 16.6 | 86 | 0.12 | La (42) | — |
| | CV60 | 36 | 16.6 | 89 | 0.05 | Eu (46) | — |
| | CV61 | 36 | 16.6 | 66 | 0.1 | Tb (46) | — |
| | CV94 | 36 | 16.6 | 79 | 0.03 | Eu, Tb, Ho, La, Pr (25 of each) | — |
| | CV97 | 36 | 16.6 | 89 | 0.05 | Eu (25), Tb (12.5), Ho (12.5), Pr (25) | — |
| 5 | CV70 | 36 | 16.6 | 135 | 0.08 | — | — |
| 6 | CV71 | 36 | 16.6 | flocculated | | Eu (25) | — |
| 7 | CV74 | 36 | 16.6 | 185 | 0.09 | Eu (25) | —COOH |
| 8 | CV13 | 36 | 16.6 | 68 | 0.04 | Eu (2) | — |
| | CV16 | 36 | 16.6 | 71 | 0.06 | Eu (46) | — |
| | CV21 | 36 | 16.6 | 60 | 0.13 | Eu (167) | — |
| 9 | CV82 | 36 | 16.6 | 91 | 0.07 | Pr, Ho, La, Tb (3 of each) | — |
| | CV90 | 36 | 16.6 | 134 | 0.03 | Pr, Ho, La, Tb, Eu (25 of each) | — |
| | CV 97 | 36 | 16.6 | 91 | 0.04 | Pr (12.5), Ho (12.5), Tb (12.5), Eu (25) | — |
| | CV116 | 36 | 16.6 | 80 | 0.03 | Pr, Ho, La, Tb, Eu (25 of each) | — |
| 10 | CV16 | 36 | 16.6 | 71 | 0.06 | Eu (46) | — |
| | CV90 | 36 | 16.6 | 134 | 0.03 | Pr, Ho, La, Tb, Eu (25 of each) | — |
| 11 | CV64 | 36 | 16.6 | 104 | 0.02 | — | — |
| | CV28 | 36 | 16.6 | 102 | 0.07 | — | — |
| 13 | CV81 | 25 | 22 | 204 | 0.03 | — | —COOH |
| | CV85 | 25 | 22 | 129 | 0.05 | Eu (167) | —COOH |
| | CV98 | 35 | 7 | 140 | 0.09 | Pr (12.5), Ho (12.5), Tb (12.5), Eu (25) | —COOH |
| 14 | CV105 | 35 | 7 | 133 | 0.05 | Pr (12.5), Ho (12.5), Tb (12.5), Eu (25) | amine |
| 16 | CV114 | 35 | 7 | 138 | 0.04 | Pr (12.5), Ho (12.5), Tb (12.5), Eu (25) | amine |

$^a$ particle diameter (d) and the polydispersity index (PDI) were measured with the BI90

TABLE 3

Particle size of samples prepared to study the hydrophobe effect.

| Samples | Example | CHDF | BI90 |
|---|---|---|---|
| CV28 (no complex) with LM | 11 | dn = 89 nm<br>dw = 100 nm | d = 102 nm<br>PDI = 0.07 |
| CV60 (Eu complex 275 mg) with LM | 2 | dn = 67 nm<br>dw = 84 nm | d = 89 nm<br>PDI = 0.05 |
| CV65 (Eu complex 275 mg) without LM | 3 | dn = 51 nm<br>dw = 61 nm | d = 73 nm<br>PDI = 0.09 |
| CV 67 and 68 (Eu complex 150 mg) without LM | 3 | dn = 41 nm<br>dw = 51 nm | d = 74 nm<br>PDI = 0.14 |
| CV80 (La complex 150 mg) without LM | 3 | dn = 65 nm<br>dw = 75 nm | d = 75 nm<br>PDI = 0.05 |

TABLE 4

Comparison of the diameter of polystyrene particles.

| Experiment | Initiator [a] | Particle diameter (nm) [b] | Polydispersitiy [b] |
|---|---|---|---|
| cv28 | KPS | 102 | 0.07 |
| cv70 | AMBN | 135 | 0.08 |

[a] Initiator amount is 1% wt/wt styrene. The reactions were run for 6 hours at 70° C.
[b] Measured by the BI90 particle sizer

TABLE 4a

The characteristics of the polystyrene particles.

| Samples | Amount of Eu complex (mg for 6 g styrene) | Mean number of Eu atoms/ particle [a] | Particle diameter (nm) [b] | polydispersity [b] |
|---|---|---|---|---|
| CV13 | 14 | 400 | 68 | 0.04 |
| CV16 | 275 | 5,600 | 71 | 0.06 |
| CV21 | 1000 | 12,400 | 60 | 0.13 |

[a] calculated from the miniemulsion recipe based on 6 g of styrene
[b] measured by the BI90 particle sizer

TABLE 5

The characteristics of the polystyrene particles.

| Samples | SDS (% w/w styrene) | Particle diameter (nm) [a] | Polydispersity [a] | Lanthanide complex (mg for 6 g styrene) | Number of lanthanide atoms/particle [b] |
|---|---|---|---|---|---|
| CV82 | 2.5 | 91 | 0.07 | Pr (20), Ho (20), La (20), Tb (20) | 3500 |
| CV90 | 2.5 | 134 | 0.03 | Pr(150), Ho(150), La(150), Tb(150), Eu(150) | 105,000 |
| CV97 | 2.5 | 91 | 0.04 | Pr (75), Ho (75), Tb (75), Eu (150) | 15,400 |
| CV116 | 2.5 | 80 | 0.03 | Pr(150), Ho(150), La(150), Tb(150), Eu(150) | 22,400 |

[a] measured by particle sizer BI90
[b] calculated values based on 6.0 g styrene used for the reactions.

TABLE 6

ICP-MS results of assays.

| samples | pH | $^{159}$Tb | $^{153}$Eu | $^{139}$La | $^{165}$Ho | $^{141}$Pr |
|---|---|---|---|---|---|---|
| control | | 12 ± 3 [a] | 609 ± 289 | 72 ± 28 | 14 ± 3 | 175 ± 14 |
| | 1.5 | 12200 ± 210 | 10580 ± 160 | 11020 ± 190 | 13990 ± 250 | 11400 ± 120 |
| | 2.6 | 10900 ± 202 | 6490 ± 121 | 10450 ± 184 | 12310 ± 195 | 12200 ± 2200 |
| CV90 [b] | 5.0 | 3300 ± 105 | 2951 ± 153 | 9040 ± 147 | 1350 ± 150 | 7750 ± 1360 |
| | 7.2 | 74 ± 27 | 206 ± 19 | 270 ± 219 | 142 ± 22 | 1900 ± 760 |
| | 9.1 | 105 ± 67 | 90 ± 41 | 71 ± 42 | 118 ± 72 | 360 ± 90 |
| CV92 [c] | 9 | 111 ± 71 | 159 ± 30 | 75 ± 39 | 122 ± 82 | 169 ± 52 |
| CV93 [d] | 9 | 89 ± 26 | 194 ± 23 | 64 ± 19 | 100 ± 24 | 136 ± 20 |
| CV94 [e] | 9 | 91 ± 39 | 66 ± 15 | 60 ± 21 | 99 ± 38 | 120 ± 32 |
| CV96 [f] | 9 | 96 ± 35 | 95 ± 17 | 80 ± 27 | 111 ± 41 | 207 ± 99 |

[a] Values reported are in ppb and are the mean of triplicate measurements
[b] 25 mg each/g styrene of Eu, Tb, Ho, Pr and La complexes
[c] 167 mg Eu complex/g styrene
[d] 167 mg Eu complex/g styrene
[e] 25 mg each/g styrene of Eu, Tb, Ho, Pr and La complexes
[f] 31 mg Eu, 13 mg Tb, 26 mg Ho, 12.5 mg Pr and 26 mg La complexes/g styrene

TABLE 7

Particle size of samples prepared with different shell functionality.

| Samples | Particle diameter (nm) [a] | Particle diameter dispersitiy [a] |
|---|---|---|
| Seed (CV97) | 91 | 0.04 |
| Core/shell with MAA (CV98) | 140 | 0.09 |
| Core/shell with AEMA (CV105) | 133 | 0.05 |

[a] Measured by the BI90 particle sizer

TABLE 8

The mean number of acid groups per particle.

| samples | Diameter (nm) [a] | Ln complex (mg/g styrene) | Mean number of —COOH/ particle | Mean number of —COOH/ nm$^2$ |
|---|---|---|---|---|
| CV81 | 204 | — | 640000 | 4.7 |
| CV83 | 206 | — | 25000 | 1.5 |
| CV117 | 92 | Pr, Ho, La, Tb, Eu (25 of each) | 24000 | 0.9 |
| CV118 | 141 | Pr, Ho, La, Tb, Eu (25 of each) | 140000 | 2.2 |
| CV119 | 215 | Pr, Ho, La, Tb, Eu (25 of each) | 180000 | 1.2 |

[a] measured by the BI90 particle sizer

TABLE 8a

ICP-MS results of experiment performed on different serum of latex containing lanthanide complexes.

| Samples [a] | pH | Measured elements | | | | |
|---|---|---|---|---|---|---|
| | | $^{153}$Eu | $^{165}$Ho | $^{141}$Pr | $^{159}$Tb | $^{139}$La |
| control | | 3 [b] ± 0.6 | 0.7 ± 0.1 | 1.6 ± 0.3 | 0.3 ± 0.1 | 30 ± 1.5 |
| CV116 | 8.9 | 57 ± 1.7 | 1742 ± 89 | 3.5 ± 0.1 | 62.6 ± 5 | 6.8 ± 1.1 |
| | 7.6 | 7.0 ± 2.7 | 1707 ± 100 | 2.3 ± 0.1 | 80 ± 3 | 3.1 ± 0.1 |
| | 5.2 | 28970 ± 1150 | 83280 ± 4740 | 42560 ± 2180 | 48260 ± 1950 | 142270 ± 7460 |
| | 2.9 | 5252 ± 217 | 13291 ± 645 | 4721 ± 186 | 6790 ± 234 | 5475 ± 114 |
| | 2.1 | 4923 ± 183 | 12860 ± 440 | 4295 ± 157 | 6285 ± 182 | 4712 ± 190 |
| CV117 | 9.9 | 12 ± 2.0 | 2.3 ± 0.6 | 2.5 ± 0.3 | 1.6 ± 0.2 | 7.0 ± 2.1 |
| | 7.4 | 12 ± 0.4 | 1.8 ± 0.0 | 0.5 ± 0.3 | 0.3 ± 0.1 | 2.0 ± 0.1 |
| | 5.5 | 3335 ± 125 | 5579 ± 281 | 1802 ± 32 | 4473 ± 110 | 2100 ± 70 |
| | 3.4 | 1862 ± 28.6 | 4241 ± 112 | 640 ± 5 | 2912 ± 73 | 588 ± 1 |
| | 2.7 | 1862 ± 24 | 4024 ± 86 | 654 ± 17 | 2774 ± 42 | 596 ± 23 |
| CV118 | 9.0 | 4 ± 0.1 | 1 ± 0.4 | 1.5 ± 0.2 | 1.4 ± 0.5 | 3.8 ± 0.8 |
| | 7.0 | 18 ± 1.5 | 2 ± 0.6 | 1.5 ± 0.3 | 1.0 ± 0.3 | 3.1 ± 1.1 |
| | 5.3 | 13 ± 1.4 | 0.5 ± 0.2 | 1.0 ± 0.4 | 0.5 ± 0.4 | 5.1 ± 0.8 |
| | 3.4 | 295 ± 2 | 854 ± 16 | 50 ± 0.2 | 541 ± 6 | 39 ± 2.6 |
| | 2.4 | 615 ± 20 | 1692 ± 55 | 102 ± 4 | 1130 ± 17 | 74 ± 7 |
| CV119 | 5.7 | 23 ± 5.1 | 76 ± 2.5 | 7.5 ± 0.9 | 39.8 ± 0.4 | 14.2 ± 0.9 |
| | 4.9 | 117 ± 5 | 332 ± 10 | 47 ± 0.8 | 218 ± 5 | 90 ± 1.4 |
| | 4.1 | 821 ± 9 | 2218 ± 30 | 229 ± 3 | 1522 ± 29 | 234 ± 5 |
| | 2.7 | 823 ± 2 | 2186 ± 55 | 185 ± 1 | 1504 ± 21 | 175 ± 10 |
| | 2.2 | 837 ± 22 | 2207 ± 57 | 191 ± 9 | 1497 ± 12 | 165 ± 0.4 |

[a] lanthanide-containing particles Eu, Tb, Ho, Pr and La complexes 25 mg each/g styrene
[b] Values reported are in ppb and are the mean of triplicate measurements

What is claimed is:

1. A method of producing polymeric particles incorporating in the particles two or more staining elements to facilitate determination of said particles by FC-MS, said method comprising:
    (a) combining two or more staining element-containing complexes with a solvent mixture comprising at least one organic monomer in which the two or more staining element-containing complexes are soluble and at least one different solvent in which said at least one organic monomer and said two or more staining element-containing complexes are less soluble, wherein at least one of said two or more staining element-containing complexes comprises a tris-4,4,4-trifluoro-1-(2-naphthyl-1,3-butanedione) ligand,
    (b) emulsifying the mixture of step (a) for a period of time sufficient to provide a uniform emulsion;
    (c) initiating polymerization and continuing reaction until a substantial portion of monomer is converted to polymer; and
    (d) incubating the product of step (c) for a period of time sufficient to obtain a latex suspension of stained polymeric particles with the two or more staining element-containing complexes incorporated in the particles therein, wherein said two or more staining element-containing complexes are selected such that upon FC-MS interrogation of each individual particle of said stained polymeric particles, a distinct MS signal is obtained from said two or more staining element-containing complexes, wherein the intensity of said distinct MS signal is proportional to the amount of said two or more staining element-containing complexes in said individual particle of said stained polymeric particles.

2. The method of claim 1, wherein the staining element-containing complexes comprise organic or inorganic metal complexes, or colloidally stable inorganic nanoparticles.

3. The method of claim 1, further comprising preparing a series of said mixtures of the at least one organic monomer having different concentrations of one or more staining elements of said two or more staining element-containing complexes in order to produce different sets of stained polymeric particles.

4. The method of claim 1, wherein said at least one organic monomer is styrene and/or methyl methacrylate.

5. The method of claim 1, wherein said different solvent in which the at least one organic monomer and said two or more staining element-containing complexes are less soluble comprises water, sodium dodecyl sulfate, and sodium bicarbonate.

6. The method of claim 1, wherein the step of initiating polymerization comprises the addition of 2,2'-azobis-(2-methylbutyronitrile) to said solvent mixture comprising at least one organic monomer in which said at least one staining element-containing complex is soluble.

7. The method of claim 1, wherein said solvent mixture comprising at least one organic monomer further comprises methacrylic acid.

8. The method of claim 1, wherein the latex suspension of polymeric particles obtained has a polydispersity index of no greater than 0.15.

* * * * *